United States Patent [19]

Zepp et al.

[11] Patent Number: 5,198,568

[45] Date of Patent: Mar. 30, 1993

[54] COMPOUNDS USEFUL IN ENZYMATIC RESOLUTION SYSTEMS AND THEIR PREPARATION

[75] Inventors: Charles M. Zepp, Berlin; Stephen A. Wald, Wayland; David R. Dodds, Millis, all of Mass.

[73] Assignee: Sepracor, Inc., Marlborough, Mass.

[21] Appl. No.: 756,950

[22] Filed: Sep. 9, 1991

Related U.S. Application Data

[62] Division of Ser. No. 178,735, Apr. 7, 1988, abandoned.

[51] Int. Cl.⁵ ............................................ C07C 69/76
[52] U.S. Cl. .................................. 560/60; 560/55; 560/61; 560/100; 560/105; 560/106; 560/130; 560/147; 560/152; 560/179
[58] Field of Search ............... 560/179, 60, 55, 61, 560/100, 105, 106, 130, 147, 152, 179

[56] References Cited

PUBLICATIONS

Bodor et al., "Soft Drugs, 1. Labile Quaternary Ammonium Salts as Soft Antimicrobials", *J. Med. Chem.*, 23, No. 5 pp. 469–474 (1980).

Bodor et al., "Soft Drugs. 2. Soft Alkylating Compounds as Potential Antitumor Agents", *J. Med. Chem.*, 23, No. 5, pp. 566–569 (1980).

Bodor et al., "Soft Drugs. 3. A New Class of Anticholinergic Agents", *J. Med. Chem.*, 23, No. 5, pp. 474–480 (1980).

Sastry, et al., "Dissociation Constants of D- and L-Lactoylcholines and Related Compounds at Cholinergic Receptors", *J. Pharmocol. Exp. Ther.*, 180(2) pp. 326–339 (1972).

Rosenfield, et al., "Analysis of the Atomic Environment of Quaternary Ammonium Groups in Crystal Structures, Using Computerized Data Retrieval and Interactive Graphics Modeling Acetylcholine-Receptor Interactions", *J. Am. Chem. Soc.*, 104(20) pp. 5427–5430 (1972).

*Primary Examiner*—Paul J. Killos
*Attorney, Agent, or Firm*—Pennie & Edmonds

[57] ABSTRACT

This invention relates to novel compositions of matter which are esters with enhanced water solubility, for use in aqueous enzymatic resolution reactions of racemic mixtures of these esters for producing the separate chiral isomers of the racemic mixture. The invention also relates to novel methods for preparing these esters. The importance of the production of the separate chiral isomers of the racemic mixtures resides in the isolation of the isomers which frequently have different biological activities. Of particular significance regarding the water soluble esters of this invention is that they are derivatized with groups which enhance their aqueous solubility and their reactivity with enzymatic resolving methods which are mediated in an aqueous environment.

101 Claims, 13 Drawing Sheets

: Denotes Hydrophobic Environment

: Denotes Hydrophilic Environment (Enzyme R-selective)

COMPOUNDS USEFUL IN ENZYMATIC RESOLUTION SYSTEMS AND THEIR PREPARATION

This is a division of copending application Ser. No. 07/178,735 filed on Apr. 7, 1988, abandoned.

TABLE OF CONTENTS 1.0 INTRODUCTION
2.0 BACKGROUND OF THE INVENTION
  2.1 SIGNIFICANCE OF OPTICAL PURITY
  2.2 CONVENTIONAL MEANS OF OBTAINING OPTICALLY PURE COMPOUNDS
  2.3 ENZYME—CATALYZED BIOCONVERSION OF LIPOPHILIC COMPOUNDS IN A HETEROGENEOUS MIXTURE
    2.3.1 NON-STEREOSPECIFIC RESOLUTIONS
    2.3.2 STEREOSPECIFIC RESOLUTIONS
3.0 SUMMARY OF THE INVENTION
4.0 BRIEF DESCRIPTION OF THE FIGURES
5.0 DETAILED DESCRIPTION OF THE INVENTION
  5.1 ESTERS FOR USE IN ENZYME-MEDIATED STEREOCHEMICAL RESOLUTION SYSTEMS AND THEIR PREPARATIONS
  5.2 ESTER RESOLUTION REACTIONS
    5.2.1 HOMOGENEOUS AQUEOUS REACTION SYSTEM
    5.2.2 EXTRACTIVE REACTION SYSTEMS
      5.2.2.1. MULTIPHASE DISPERSION EXTRACTIVE REACTION
      5.2.2.2. EXTRACTIVE MEMBRANE REACTORS
    5.2.3, REACTION AND RESOLUTION PROCESS PARAMETERS
6.0 EXAMPLES
  6.1 SYNTHESIS OF WATER-SOLUBLE AND WATER INSOLUBLE ESTERS
    6.1.1: Method A1 Preparation of the Sodium Salt of 4-Sulfomethyl Ester of 2-(4-Isobutylphenyl)-propanoic Acid (Compound 1)
    6.1.2: Method B1 Preparation of the Sodium Salt of 4-Sulfomethyl Ester of 2-(4-Isobutylphenyl)propanoic Acid (Compound 1)
    6.1.3: Method A2 Preparation of the Sodium Salt of 2-Sulfoethyl Ester of 2-(4-Isobutylphenyl)-propanoic Acid (Compound 2)
    6.1.4: Method C1 Preparation of the Potassium Salt of 3-Sulfopropyl Ester of 2-(4-Isobutylphenyl)propanoic Acid (Compound 3)
    6.1.5: Method C2 Preparation of the Potassium Salt of 4-Sulfobutyl Ester of 2-(4-Isobutylphenyl)propanoic Acid (Compound 4)
    6.1.6: Method D Preparation of the Disodium Salt of the Phosphoric Acid Ester of the 2-Hydroxyethyl Ester of 2-(4-Isobutylphenyl)-propanoic Acid (Compound 5)
    6.1.7: Method E Preparation of the Potassium Salt of the Sulfuric Acid Ester of 3-Hydroxypropyl Ester of 2-(4-Isobutylphenyl)propanoic Acid (Compound 6)
    6.1.8: Method C3 Preparation of the Potassium Salt of the 3-Sulfopropyl Ester of 2-(6-Methoxy-2-naphthyl)propanoic Acid (Compound 7)
    6.1.9: Method B2 Preparation of the Potassium Salt of 2-Sulfoethyl Ester of 2-(6-Methoxy-2-naphthyl)propanoic Acid (Compound 8)
    6.1.10: Method A3 Preparation of the Sodium Salt of Sulfomethyl Ester of 2-(6-Methoxy-2-naphthyl)propanoic Acid (Compound 9)
    6.1.11: Method F1 Preparation of the Iodide Salt of 2-(N,N,N-Trimethylammonium)ethyl Ester of 2-(4-Isobutylphenyl)propanoic Acid (Compound 10)
    6.1.12: Method Preparation of the Methyl Sulfate Salt of 2-(N,N,N-Trimethylammonium)ethyl Ester of 2-(6-Methoxy-2-naphthyl)-propanoic Acid (Compound 11)
    6.1.13: Method F2 Preparation of the Methyl Sulfate Salt of 2-(N,N,N-Trimethylammonium)propyl Ester of 2-(6-Methoxy-2-naphthyl)propanoic Acid (Compound 12)
    6.1.14: Method F3 Preparation of the Potassium Salt of 3-Sulfopropyl Ester of 2-Chloropropanoic Acid (Compound 13)
    6.1.15: Method C4 Preparation of the Potassium Salt of 3-Sulfopropyl Ester of 2-Chloropropanoic Acid (Compound 13)
    6.1.16: Method B4 Preparation of the Potassium Salt of the Sulfomethyl Ester of L-(+)-S-3-Acetylthio-2-methylpropanoic Acid (Compound 15)
    6.1.17: Method B5 Preparation of the Potassium Salt of the Sulfomethyl Ester of (±)-S-3-Benzoylthio-2-methylpropanoic Acid (Compound 16)
    6.1.18: Method B6 Preparation of the Sodium Salt of the Sulfomethyl Ester of 2-(4-Chlorophenoxy)propanoic Acid (Compound 17)
    6.1.19: Method B7 Preparation of Methyl Ester of 2-(6-Methoxy-2-naphthyl)propanoic Acid (Compound 18)
    6.1.20: Method B8 Preparation of 2,2,2-Trifluoroethyl Ester of 2-(4-Isobutylphenyl)-propanoic Acid (Compound 19)
    6.1.21: Method G Preparation of Octyl Ester of 2-Chloropropanoic Acid (Compound 20)
  6.2 SPECIFICITY AND ACTIVITY OF ENZYMATIC RESOLUTION REACTIONS OF RACEMIC MIXTURES OF WATER-SOLUBLE AND WATER-INSOLUBLE ESTERS
    6.2.1 ENZYMATIC RESOLUTIONS BY HOMOGENEOUS AQUEOUS REACTIONS
      6.2.1.1: Homogeneous Aqueous Resolution of Sodium Salt of 4-Sulfomethyl Ester of 2-(4-Isobutylphenyl)propanoic Acid Using 100 mg of Enzyme A at pH 7.0
      6.2.1.2: Homogeneous Aqueous Resolution of Sodium Salt of 2-Sulfoethyl Ester of 2-(4-Isobutylphenyl)propanoic Acid Using 100 mg of Enzyme A at pH 7.0
      6.2.1.3: Homogeneous Aqueous Resolution of Potassium Salt of 3-Sulfopropyl Ester of 2-(4-Isobutylphenyl)propanoic Acid Using 100 mg of Enzyme A at pH 7.0
      6.2.1.4: Homogeneous Aqueous Resolution of Potassium Salt of 4-Sulfobutyl Ester of 2-(4-Isobutylphenyl)propanoic Acid Using 100 mg of Enzyme A at pH 7.0
      6.2.1.5: Homogeneous Aqueous Resolution of Sodium Salt of 4-Sulfomethyl Ester of 2-(4-

Isobutylphenyl)propanoic Acid Using 100 mg of Enzyme B at pH 7.0

6.2.1.6: Homogeneous Aqueous Resolution of Sodium Salt of 4-Sulfomethyl Ester of 2-(4-Isobutylphenyl)propanoic Acid Using 100 mg of Enzyme C at pH 7.0

6.2.1.7: Homogeneous Aqueous Resolution of Sodium Salt of 4-Sulfomethyl Ester of 2-(4-Isobutylphenyl)propanoic Acid Using 100 mg of Enzyme D at pH 7.0

6.2.1.8: Homogeneous Aqueous Resolution of Potassium Salt of 3-Sulfopropyl Ester of 2-(4-Isobutylphenyl)propanoic Acid Using 150 mg of Enzyme A at pH 7.8

6.2.1.9: Homogeneous Aqueous Resolution of Potassium Salt of 3-Sulfopropyl Ester of 2-(4-Isobutylphenyl)propanoic Acid Using 150 mg of Enzyme B at pH 7.8

6.2.1.10: Homogeneous Aqueous Resolution of Potassium Salt of 3-Sulfopropyl Ester of 2-(4-Isobutylphenyl)propanoic Acid Using 150 mg of Enzyme B at pH 7.8

6.2.1.11: Homogeneous Aqueous Resolution of Potassium Salt of 3-Sulfopropyl Ester of 2-(4-Isobutylphenyl)propanoic Acid Using 30 mg of Enzyme E at pH 7.0

6.2.1.12: Homogeneous Aqueous Resolution of Sodium Salt of 2-Sulfoethyl Ester of 2-(4-Isobutylphenyl)propanoic Acid Using 150 mg of Enzyme A at pH 7.0

6.2.1.13: Homogeneous Aqueous Resolution of Sodium Salt of 2-Sulfoethyl Ester of 2-(4-Isobutylphenyl)propanoic Acid Using 150 mg of Enzyme B at pH 7.0

6.2.1.14: Homogeneous Aqueous Resolution of Potassium Salt of 4-Sulfobutyl Ester of 2-(4-Isobutylphenyl)propanoic Acid Using 100 mg of Enzyme B at pH 7.0

6.2.1.15: Homogeneous Aqueous Resolution of Potassium Salt of 4-Sulfobutyl Ester of 2-(4-Isobutylphenyl)propanoic Acid Using 100 mg of Enzyme C at pH 7.0

6.2.1.16: Homogeneous Aqueous Resolution of disodium Salt of the Phosphoric Acid Ester of the 2-Hydroxyethyl Ester of 2-(4-Isobutylphenyl)propanoic Acid Using 100 mg of Enzyme C at pH 7.0

6.2.1.17: Homogeneous Aqueous Resolution of Iodide Salt of 2-(N,N,N-Trimethylammonium)ethyl Ester of 2-(4-Isobutylphenyl)propanoic Acid Using 100 mg of Enzyme A at pH 7.0

6.2.1.18: Homogeneous Aqueous Resolution of Methyl Sulfate Salt of 2-(N,N,N-Trimethylammonium)ethyl Ester of 2-(6-Methoxy-2-naphthyl)propanoic Acid Using 100 mg of Enzyme F at pH 7.0

6.2.1.19: Homogeneous Aqueous Resolution of Methyl Sulfate Salt of 3-(N,N,N-Trimethylammonium)propyl Ester of 2-(6-Methoxy-2-naphthyl)propanoic Acid Using 100 mg of Enzyme F at pH 7.0

6.2.1.20: Homogeneous Aqueous Resolution of Potassium Salt of the 3-Sulfopropyl Ester of 2-(6-Methoxy-2-naphthyl)propanoic Acid Using 150 mg of Enzyme A at pH 7.8

6.2.1.21: Homogeneous Aqueous Resolution of Potassium Salt of 3-Sulfopropyl Ester of 2-(4-Isobutylphenyl)propanoic Acid Using 1000 mg of Enzyme A at pH 7.0

6.2.1.22: Homogeneous Aqueous Resolution of Sodium Salt of 4-Sulfomethyl Ester of 2-(4-Isobutylphenyl)propanoic Acid Using 100 mg of Enzyme F at pH 7.0

6.2.1.23: Homogeneous Aqueous Resolution of Potassium Salt of 2-Sulfoethyl Ester of 2-(6-Methoxy-2-naphthyl) propanoic Acid Using 150 mg of Enzyme A at pH 7.8

6.2.1.24: Homogeneous Aqueous Resolution of Potassium Salt of the Sulfuric Acid Ester of the 3-Hydroxypropyl Ester of 2-(4-Isobutylphenyl)propanoic Acid Using 100 mg of Enzyme A at pH 7.0

6.2.1.25: Homogeneous Aqueous Resolution of Sodium Salt of Sulfomethyl Ester of 2-(6-Methoxy-2-naphthyl)propanoic Acid Using 100 mg of Enzyme A at pH 7.5

6.2.1.26: Homogeneous Aqueous Resolution of Potassium Salt of 3-Sulfopropyl Ester of 2-Chloropropanoic Acid Using 20 mg of Enzyme B at pH 7.0

6.2.1.27: Homogeneous Aqueous Resolution of Potassium Salt of the Sulfomethyl Ester of ($\pm$)-S-3-Benzoylthio-2-methylpropanoic Acid Using 100 mg of Enzyme B at pH 7.0

6.2.1.28: Homogeneous Aqueous Resolution of Potassium Salt of the Sulfomethyl Ester of ($\pm$)-S-3-Benzoylthio-2-methylpropanoic Acid Using 100 mg of Enzyme A at pH 7.0

6.2.1.29: Homogeneous Aqueous Resolution of Sodium Salt of the Sulfomethyl Ester of 2-(4-Chlorophenoxy)propanoic Acid Using 35 mg of Enzyme F at pH 7.0

6.2.1.30: Homogeneous Aqueous Resolution of Sodium Salt of 4-Sulfomethyl Ester of 2-(4-Isobutylphenyl)propanoic Acid Over Time Using 3 gm of Enzyme F at pH 7.0

6.2.2 ENZYMATIC RESOLUTIONS IN EXTRACTIVE DISPERSION OR MEMBRANE REACTORS 6.2.2.1: Resolution of Sodium Salt of 4-sulfomethyl Ester of 2-(4-Isobutylphenyl)-propanoic Acid via Asymmetric Hydrolysis in an Extractive Dispersion Reactor 6.2.2.2: Resolution of Sodium Salt of 4-sulfomethyl Ester of 2-(4-Isobutylphenyl)-propanoic Acid via Asymmetric Hydrolysis Not Associated with the Membrane in an Extractive Membrane Reactor 6.2.2.3: Resolution of Sodium Salt of 4-sulfomethyl Ester of 2-(4-Isobutylphenyl)-propanoic Acid via Asymmetric Hydrolysis Associated with the Membrane in an Extractive Membrane Reactor with an Enzyme Activated Membrane 6.2.2.4: Resolution of Sodium Salt of 4-sulfomethyl Ester of 2-(4-Isobutylphenyl)-propanoic Acid via Asymmetric Hydrolysis Associated and Not Associated with the Membrane in an Extractive Membrane reactor 6.2.2.5: Resolution of Methyl Ester of 2-(6-Methoxy-2-naphthyl)propanoic Acid via Asymmetric Hydrolysis in a Multiphasic Bioreactor 6.2.2.6: Resolution of 2,2,2-Trifluoroethyl Ester of 2-(4-Isobutylphenyl)propanoic Acid via Asymmetric Hydrolysis in a Multiphasic Bioreactor 6.2.2.7: Resolution of Octyl Ester of 2-Chloropropanoic Acid via Asymmetric Hydrolysis in a Multiphasic Bioreactor 6.2.3 DETERMINATION OF ENZYME RESOLUTION ACTIVITY AND SPECIFICITY 6.2.3.1: Determination of Activity and Specificity of Enzyme B with Respect to the Two Enantiomers of S-3-Acetylthio-2-methylpropanoic Acid Sulfomethyl Ester 6.2.3.2: Determination of Activity and Specificity of Enzyme I with Respect to the Two Enantiomers of S-3-Acetylthio-2-methylpropanoic Acid Sulfomethyl Ester 6.2.3.3: Determination of Activity and Specificity of Enzyme A with Respect to the Two Enantiomers of S-3-Acetylthio-2-methylpropanoic Acid Sulfomethyl Ester 6.2.3.4: Determination of Activity and Specificity of Enzyme J with Respect to the Two Enantiomers of S-3-Acetylthio-2-methylpropanoic Acid Sulfomethyl Ester 6.2.3.5: Determination of Activity and Specificity of Enzyme D with Respect to the Two Enantiomers of S-3-Acethylthio-2-methylpropanoic Acid Sulfomethyl Ester

1.0 INTRODUCTION

This invention relates to novel compositions of matter which are esters with enhanced water solubility, for use in aqueous enzymatic resolution reactions of racemic mixtures of these esters. Of particular significance regarding the water soluble esters of this invention is that they are derivatized with groups which enhance their aqueous solubility and their reactivity with enzymatic resolving methods which are mediated in an aqueous environment.

The invention also relates to novel methods for preparing these esters, for use in novel methods for enzymatically resolving the racemic mixtures of the esters, for producing the separate chiral isomers of the racemic mixture. The importance of the production of the separate chiral isomers of the racemic mixtures resides in the isolation of the isomers which frequently have different biological activities.

The importance of these compounds resides in their being useful in novel methods for facilitating the enzymatic resolution reactions of racemic mixtures of esters, which are derivatized with groups which enhance the esters' aqueous solubility, in a homogeneous aqueous reaction system where an extractive phase is not present and in a multiphase dispersion extractive reaction where an extractive phase is present. The extractive phase serves to remove the resolving reaction product.

Additionally, the importance of these compounds resides in their being useful in novel methods for facilitating the homogeneous enzymatic resolving of racemic mixtures of esters, which are derivatized with groups which enhance the esters, aqueous solubility, in an extractive membrane reactor where the enzyme is placed alternatively either (1) in the aqueous phase, (2) in association with the membrane, or (3) in the aqueous phase and in association with the membrane, wherein the aqueous ester phase is contacted with one side of the membrane, and where an organic extractive phase is contacted with the other side of the membrane. The extractive phase serves to remove the resolving reaction product.

2.0 BACKGROUND OF THE INVENTION

Enzymatic resolution procedures have long been known and exploited, especially for the separation of racemic mixtures on the preparative scale. Unfortunately, many chiral compounds of commercial significance are hydrophobic and thus exhibit very low water solubilities. Since enzymes generally operate in aqueous solutions and not organic solvents, it has proven difficult to facilitate the enzyme-catalyzed bioconversion and subsequent separation of selected poorly water-soluble optical isomers.

2.1 SIGNIFICANCE OF OPTICAL PURITY

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

The property of optical activity is due to molecular asymmetry about carbon atoms that are linked to four different atoms. Where there is only one asymmetric carbon atom, or chiral center as it is sometimes called, there are two possible stereoisomers. Where there are n asymmetric carbons or chiral centers, the number of potential stereoisomers increases to $2^n$. Thus, a molecule with three chiral centers would have eight possible stereoisomers.

While the structural differences between stereoisomers are subtle and of little consequence in ordinary chemical reactions, they may be profound where biological systems are concerned, i.e., if the compounds are utilized in enzyme-catalyzed reactions. Thus, the L-amino acids are metabolized in humans but the corresponding D-analogs are not, and only D-glucose can be phosphorylated and processed into glycogen or degraded by the glycolytic and oxidative pathways of intermediary metabolism. Similarly, beta blockers, pheromones, prostaglandins, steroids, flavoring and fragrance agents, pharmaceuticals, pesticides, herbicides and many other compounds exhibit critical stereospecificity. In the field of pesticides, Tessier [Chemistry and Industry, Mar. 19, 1984, p. 199] has shown that only two of the eight stereoisomers of deltamethrin, a pyrethroid insecticide, have any biological activity. The same statement concerning the concentration of bioactivity in a single isomer can be made about many other pesticides, including the phenoxypropionates and halopropionate derivatives, each containing one chiral center and existing in the form of two optical isomers.

Stereochemical purity is of equal importance in the field of pharmaceuticals, where 12 of the 20 most prescribed drugs exhibit chirality. A case in point is provided by naproxen, or (+)-S-2-(6-methoxy-2-naphthyl)- propanoic acid, which is one of the two most important members of a class of 2-arylpropanoic acids with nonsteroidal anti-inflammatory activity used, for instance, in the management of arthritis. In this case, the S(+) enantiomer of the drug is known to be 28 times more therapeutically potent than its R(−) counterpart. Still another example of chiral pharmaceuticals is provided by the family of beta-blockers; the L-form of propranolol is known to be 100 times more potent than the D-enantiomer.

Synthesis of compounds with asymmetric centers by standard organic synthetic techniques generally leads to a racemic mixture which, in the aggregate, may have a relatively low specific bioactivity since certain of the stereoisomers in the mixture are likely to be biologically or functionally inactive. As a result, larger quantities of the material must be used to obtain an effective dose, and manufacturing costs are increased due to the coproduction of stereochemically "incorrect" and hence, inactive ingredients.

In some instances, certain isomers may actually be deleterious rather than simply inert. For example, the D-enantiomer of thalidomide was a safe and effective sedative when prescribed for the control of morning sickness during pregnancy However, its L-thalidomide counterpart was discovered to be a potent teratogen.

2.2 CONVENTIONAL MEANS OF OBTAINING OPTICALLY PURE COMPOUNDS

Methods are available for stereoselective synthesis. For example, a synthetic pathway to optically pure deltamethrin [(1R,3R)-3-(2,2-dibromovinyl)-2,2-dimethyl cyclopropane carboxylic acid] has been developed, but the process is lengthy, complex and costly [Tessier, J., Chem. and Ind., Mar. 9, 1984, p.199]. Moreover, a synthetic scheme capable of producing one specific enantiomer cannot be applied in a general way to obtain other optically active compounds. What is needed is a generalized approach to the resolution of racemic mixtures produced by ordinary chemical reactions, and a number of approaches have been used.

The term "racemic mixture" as used herein, refers to a mixture of a first and a second stereoisomer in any proportions, such that the first and second stereoisomers are enantiomers that do not possess any element of reflective symmetry. Further, it is intended that the term "resolution" as used herein will refer to the transformation of a racemic mixture, as defined above, into two product mixtures, in each of which the proportions of the two above defined stereoisomers may be different from both the starting racemic mixture and from each other, the proportion being greater in one and necessarily smaller in the other. Additionally, in each of these product mixtures there may also be one or more new compounds, each of which possesses a first and a second stereoisomer such that these stereoisomers are enantiomers, and such that the proportion of one stereoisomer of such new compounds is greater in one product mixture than in the other product mixture. The term "resolved" is intended to refer to a quantity of any compound, capable of resolution, and which has undergone the process of resolution defined above to yield an optically active product material Finally, the terms "stereospecific" and "stereoselective" as used herein are synonymous.

A widely used approach has been the selective precipitation of desired compounds from racemic mixtures For example, Yoshioka et al. [U.S. Pat. No. 3,879,451] treated a mixture of (±)-cis- and (±)-trans-chrysanthemic acids with an optically active aromatic amine and recovered the amine salts of (±)-cis- and (±)-trans-chrysanthemic acids by crystallization Paven et al. [U.S. Pat. No. 4,257,976] resolved D,L-cis-chrysanthemic acid and D,L-transchrysanthemic acid by treating the mixtures with L or D N-methyl-ephedrine to form the corresponding salts, which were then hydrolyzed after isolation to produce the resolved acids. Halmos [U.S. Pat. No. 4,151,198] treated a mixture of N-acyl-D,L(±)-phenylalanine isomers with D(−)-2-(2,5-dimethylbenzylamino)-1-butanol to obtain a crystalline salt, from which N-acyl-L(+)-phenylalanine could be recovered. Kameswaran [U.S. Pat. No. 4,454,344] isolated (+) 2-(p-difluoromethoxyphenyl)-3-methylbutanoic acid by treating the racemic acid with an optically active amine. The S(+)-enantiomer of naproxen can be obtained by stereoselective crystallization of a diastereomeric salt formed with an amine resolving agent such as cinchonidine, glucamine, or N-methylglucamine [Harrison, I. T. et al., J. Med. Chem., 13:203 (1970); Felder, E. et al., U.K. Patent Appl. GB2025968A (1980)].

In some cases, a two-step method has been used, as when Dannenberg et al. [U.S. Pat. No. 4,285,884] resolved racemic D,L-alpha-aminocarboxylic acids by first treating the mixture with an aromatic o-hydroxy aldehyde to obtain an azomethine derivative. This derivative was then immediately treated with an optically active amine base to produce a salt which was isolated. By subjecting the salt to acid hydrolysis, the desired alpha-aminocarboxylic acid isomer was obtained.

The above procedures successfully resolved racemic mixtures because treatment of the mixtures with optically pure reagents produced diastereomers which, unlike the initial racemic compounds, have different physical properties. Thus, fractional crystallization or other physical means may be employed to separate diastereomeric compounds.

Separation of diastereomers can also be carried out by chromatography. For example, Pollock et al. [J. Gas Chromatogr. 3:174 (1965)] have resolved diastereomeric amino acids by gas chromatography. Mikes et al. [J. Chromatogr. 112:205 (1976)] have used liquid chromatography to resolve diastereomeric dipeptides. In most cases, the optically pure reagents have been in the stationary phase during chromatographic separation, but they may also be used in elutants. Hare et al. [U.S. Pat. No. 4,290,893] have used liquid chromatography to resolve racemic mixtures that were treated with aqueous elutants containing optically pure reagents and metal cations; resolution occurred because the resulting diastereomeric complexes had different partition coefficients in the chromatographic system.

2.3 ENZYME—CATALYZED BIOCONVERSION OF LIPOPHILIC COMPOUNDS IN A HETEROGENEOUS MIXTURE

Various enzymes have been used for bioconversions of assorted classes of lipophilic organic compounds, including alcohols, carboxylic acids, esters, amides and amines, in heterogeneous reaction systems. In particular, the enzymatic bioconversions have been shown to be useful in catalyzing stereoselective synthesis of the noted compounds.

2.3.1 Non-Stereospecific Reactions

For the most part, attempts by biochemical engineers to exploit enzymatic catalysis in large-scale industrial biotransformations have focused on the use of enzymes in aqueous reaction systems containing water-soluble substrates. The conversion of glucose to fructose by glucose isomerase affords one such example. However, enzymes are also used in the bioconversion of lipophilic (i.e., sparingly water-soluble) substrates. For example, many of the structurally complex pharmaceutical compounds and agricultural chemicals are prime candidates for enzymatic bioconversions. In particular, such complex molecules are often chiral. Unfortunately, many of these complex molecules exhibit very low water solubilities, and it is generally impractical to feed such poorly water-soluble substrates to conventional immobilized enzyme bioreactors in homogeneous, aqueous solution for several reasons. On the one hand, enzyme reactors sized to deal with such dilute reaction systems would be inordinately large, and recovery and concentration of bioproducts from such dilute aqueous process streams would often prove prohibitively expensive. Several prior-art approaches have been explored for making enzyme-catalyzed conversions of water-insoluble substrates more efficient, including the use of water-miscible cosolvent [Tanaka, A. and S. Fukui, "Bioconversion of Lipophilic Compounds by Immobilized Biocatalysis in the Presence of Organic Solvents," pp. 149–176 in *Enzymes and Immobilized Cells in Biotechnology*, A. I. Laskin, ed., Benjamin/Cummings Publishing Co., Menlo Park, CA (1985); Klibanov, A. M. et al., Biotechnol. Bioeng., 19:1351 (1977)] and the conduct of enzyme-catalyzed bioconversions of sparingly water-soluble substrates in multiphase systems [Lilly, M., J. Chem. Tech. Biotechnol., 32:162 (1982); Carrea, G., Trends in Biotechnol., 2:102 (1984)](FIG. 6). Both of these approaches are problematic, however, as discussed in copending application Ser. No. 033,962.

Other examples of multiphase, biocatalytic reactions include the enzymatic hydrolysis of triglycerides (e.g., olive oil) to fatty acids [Linfield, W. M. et al., JAOCS, 61:191 (1984)] and the microbial production of optically active epoxides (e.g., 1,2-epoxyoctane) from alkenes [van der Meer, Chem. Eng. Sci., 41:607 (1986)].

2.3.2 Stereospecific Resolutions

All of the methods described to this point have relied upon the availability of suitable optically pure reagents, but such reagents are often not available or else their use is prohibitively expensive. In an alternative approach, enzymatic resolution techniques have been developed. Many different classes of enzymes have been used for the resolution of stereoisomers on a preparative scale, including hydrolases (especially the lipases, proteases and esterases such as chymotrypsin), lyases and oxidoreductases (e.g., amino acid oxidases and alcohol reductases). Generally speaking, enzymes for use in resolutions should ideally exhibit broad substrate specificity, so that they will be capable of catalyzing reactions of a wide range of "unnatural" substrates, and they should exhibit a high degree of stereoselectivity for catalyzing the reaction of one isomer to the exclusion of others.

The hydrolases (e.g., lipases, proteases and esterases) are among the more attractive enzymes for use in resolutions, because they are commercially available at reasonable cost, they do not require expensive cofactors, and some of them exhibit reasonable tolerance to organic solvents. Additionally, chiral chemistry often involves alcohols, carboxylic acids, esters, amides and amines with chiral carbons, and carboxyl hydrolases are preferred choices as stereoselective catalysts for reactions of such species [Cambou, B. and A. M. Klibanov, Biotechnol. Bioeng., 26:1449 (1984)].

Many pharmaceuticals and agricultural chemicals exhibit very low solubilities in water, and accordingly a number of the enzyme-mediated optical resolutions of such compounds as cited above were conducted under multiphasic reaction conditions. In one such example, Cambou and Klibanov [Biotechnol. Bioeng., 26:1449 (1984)] investigated the lipase-mediated resolution of 2-(p-chlorophenoxy)propanoic acid, derivatives of which are herbicides. They found yeast lipase (*Candida cylindracea*) to be highly stereospecific in the resolution of (R,S)-2-(p-chlorophenoxy)propanoic acid when used to catalyze hydrolysis of simple esters (e.g., the methyl ester) of the racemic acid. Because these esters are substantially water-insoluble, the resolution procedure was necessarily conducted in a multiphase reaction system wherein three separate phases were present: namely, an organic phase containing the racemic reactant ester, an aqueous buffer, and the immobilized enzyme. Typically, the lipase was immobilized by entrapment and adsorption on high-surface-area Chromosorb or titania beads, and this solid-phase enzyme and the organic phase containing the reactant were dispersed within the aqueous phase by vigorous shaking to produce an emulsion. By this means, Cambou and Klibanov produced the desired R-acid in hundred gram quantities in 85% yield and at 97% chemical purity; the enantiomeric excess of R-acid over S-ester was found to be 96%.

In addition, enzymatic treatment has been applied to the resolution of racemic mixtures of amino acid esters. Stauffer [U.S. Pat/ No. 3,963,573] produced optically pure N-acyl-L-methionine by treating N-acyl-D,L-methionine ester with microbial proteases and separating the product acid from the reaction mixture. Similarly, Bauer [U.S. Pat No. 4,262,092] prepared optically pure D-phenylalanine ester by subjecting a racemic mixture of an N-acyl-D,L-phenylalanine ester to the action of a serine protease, separating the unaffected N-acyl-D-phenylalanine ester, and removing the N-acyl and ester groups. Clement and Potter [*J. Chem. Ed.*, 48:695 (1971)] employed chymotrypsin to resolve phenylalanine, and Matta et al. [*J. Org. Chem.*, 39:2291 (1974)] used the same enzyme in the resolution of precursors of the drug 3-(3,4-dihydroxyphenyl)alanine or dopa.

Amino acid resolution with chymotrypsin involves first forming the acyl and ester derivatives by standard procedures and then subjecting the racemic mixture to enzymatic hydrolysis. The inert, poorly water-soluble D-ester is generally separated from the much more water-soluble N-acylated L-amino acid product by selective extraction with an organic solvent. The free L- and D-amino acids can be recovered (e.g., by acid hydrolysis) if desired, and the unwanted isomer racemized and recycled. Alternatively, separation of reaction products from enzymes has been facilitated by attaching the enzyme to a solid support which could be removed by centrifugation or packed into a column through which the racemic mixtures were passed. Matson [Membrane Reactors, Doctoral Dissertation, University of Pennsylvania (1979)] used chymotrypsin immobilized on a membrane to selectively cleave the L-amino acid ester linkage in a racemic aqueous mixture of N-acetyl-D,L-tyrosine ethyl ester. Scollar et al. [*Biotech. Bioeng.*, 27:247 (1985)] employed acid phosphatases in the preparative-scale resolution of D,L-threonine.

Enzymes have also been explored for the resolution of classes of compounds other than the amino acids discussed above. In particular, Cambou and Klibanov [*Biotech. Bioeng.*, 26;1449 (1984)] examined the use of lipase immobilized in porous beads for the enzymatic resolution of mixtures of (R,S)-2-(p-chlorophenoxy)-propanoic acid (whose R isomer is an herbicide) and various esters thereof. Their studies showed that the immobilized lipase could in principle resolve the mixtures by enzymatic hydrolysis or transesterification. In the case of the biphasic hydrolysis reaction, the differing solubility properties of the acids and esters involved required the dispersion and agitation of mixtures containing the immobilized solid-phase enzyme, an aqueous buffer, and the water-immiscible organic phase containing solvent and reactant—a relatively inefficient process.

Enzymes have been applied to the resolution of optical isomers of insecticides. For instance, Mitsuda et al. [Eur. Patent Appl'n. Publ. No. 0 080 827 A2] contacted the racemic acetic acid ester derivative of (R,S)-alpha-cyano-3-phenoxybenzyl alcohol with stereoselective esterases of microbial and animal origin in biphasic systems (i.e., aqueous/organic dispersions). The S-ester was selectively hydrolyzed, thereby producing (S)-(−)-alpha-cyano-3-phenoxybenzyl alcohol, an alcohol moiety of the pyrethroid family of insecticides. In related work on optically purified pyrethroids, Mitsuda et al. [U.S. Pat. No. 4,607,013] employed microbial esterases for the optical resolution of racemic (±)-4-hydroxy-3-methyl-2,2,-propynyl-2-cyclopentenone; the ester derivative of the (□:)-isomer of this compound has several times the pesticidal activity of its (−)-isomer counterpart. Klibanov et al. [U.S. Pat. No. 4,601,987] resolved racemic 2-halopropanoic acids by means of lipase-catalyzed esterification reactions conducted in organic media. The resolved 2-halopropanoic acids so prepared can be employed in the synthesis of 2-phenoxypropanoic acids and their esters; these are widely used as herbicides, with only the R optical isomers exhibiting biological activity.

Additional examples can also be provided of the state-of-the-art of enzyme-mediated resolution as applied to the production of optically purified pharmaceuticals. Sih [U.S. Pat. No. 4,584,270] has disclosed enzymatic means for the production of optically pure (R)-4-amino-3-hydroxybutanoic acid, a key intermediate in the preparation of L-carnitine. Other microbial- or enzyme-mediated approaches to L-carnitine manufacture have been disclosed by Aragozzini et al. [Biotechnol. Letters, 8:95 (1986)] and by Yokozeki et al. [Eur. Patent Appl'n. Publ. No. 0 122 794 A2]. Finally, certain optically pure D-amino acids (in particular, the D-arylglycines such as phenylglycine and 4-hydroxyphenylglycine) are used as side chains in the manufacture of semisynthetic penicillins and cephalosporins. Schutt et al. [Biotechnol. Bioeng., 27:420 (1985)] have subjected racemic mixtures of such nonpolar N-acyl-D,L-amino acid esters to the hydrolytic action of subtilisin in two-phase systems for the purpose of obtaining optically purified D-amino acids.

More specifically, microbial- or enzyme-mediated resolutions of ibuprofen and naproxen are also provided. However, these examples employ enzyme reactants which are aqueous-immiscible. Consequently, the reactants, susceptibility for resolution with the aqueous soluble enzyme is less than desired.

S. Iriuchijima and A. Keiyu in *Agri. Bio. Chem.*, 45, 1389 (1981) partially resolved the methyl ester of (±)-2-(6-methoxy-2-naphthyl) propanoic acid using an intact microorganism. Unfortunately, the rate of conversion was very slow (16.3% of the substrate was converted), because the intracellular enzyme concentration was low, and the amount of dried cells (400 mg) exceeded the (±)-substrate (160 mg). Consequently, this process failed to achieve the desired objective.

In other references, enzymes derived from microorganisms were utilized to resolve esters of naproxen and ibuprofen. C. J. Sih et al., in Tetrahedron Letters, 27(16), 1763-1766 (1986), describes that esters of ibuprofen and naproxen are capable of being stereospecifically resolved using a microorganism derived lipase. The specific esters which are utilized are methyl, ethyl, n-butyl, n-pentyl, n-hexyl, n-heptyl, n-octyl, 2-chloroethyl, cyanomethyl and 2-nitropropyl. In European Patent 0,227,078 A1 by C. J. Sih, ibuprofen and naproxen esters are resolved with lipases from assorted microorganisms. Although Sih discloses that the ester group is "preferably a straight, branched, or cyclic alkyl group having from 1 to 12 carbon atoms, optionally substituted with phenyl or one or more electron-withdrawing substitutents, for example halo, nitro, cyano, hydroxy, $C_{1-4}$ alkoxy, $C_{1-4}$ alkylthio, or $—C(O)R^1$ wherein $R^1$ is $C_{1-4}$ alkyl, $C_{3-6}$ cycloalkyl, hydroxy, $C_{1-4}$ alkoxy, $C_{3-6}$ cycloalkoxy, phenoxy, benzyloxy, $NR^2R^3$ [in which $R^2$ and $R^3$ are independently $H_1$, $C_{1-4}$ alkyl, $C_{3-6}$ cycloalkyl, or jointly form a 5- or 6-membered ring together with the nitrogen, the ring optionally including a hetero group selected from O, NH, or N-($C_{1-4}$ alkyl)], or -OM wherein M is an alkali metal . . . . [(p. 3)]," however, Sih only describes the use of methyl, n-butyl, n-hexyl, n-octyl, n-dodecyl, benzyl, 2-chloroethyl, 2,2,2-trichloroethyl, cyanomethyl, 2-nitropropyl, 2-bromoethyl, carboethoxymethyl, methoxymethyl, 2-fluoroethyl and 2,2,2-trifluoroethyl esters. J. Maier et al., in German Patent DE 3,345,660 Al, describes stereospecific resolutions of "lower alkyl" esters of naproxen using enzymatic preparations. The "lower akyl" term referred to alkyl groups from $C_1$ to $C_4$. In common among these references is their utilization of esters, which exhibit aqueous insolubility, for resolutions by enzymatic preparations in an aqueous medium. Therefore, the enzymatic conversions were heterogeneous in nature.

Phillips et al., in European Patent 0,205,215 A2, describes an alternative preparation of ibuprofen and naproxen using an enzyme derived from a microoganism for the stereoselective oxidation of 2-substituted propane, wherein one of the terminal methyl groups of the propane is oxidized to the corresponding carboxyl group. The stereospecific oxidation facilitates the production of the S-configuration at the 2-position of the oxidized propane. However, this stereospecific oxidation is consequently distinguished from the prior noted enzymatic stereospecific resolution of aqueous-immiscible esters of ibuprofen or naproxen.

Unfortunately, the prior noted multiphasic/heterogeneous reaction systems suffer from a number of drawbacks, particularly on the industrial scale. For example, scale-up and reliability problems are frequently associated with the processing of dispersions and emulsions, and continuous operation and pH control (especially in hydrolytic reactions) are difficult to achieve. Additionally, the phases must be separated before product can be recovered, and excessive interphase mass transfer resistances are often encountered, associated with diffusion of the poorly soluble substrate in the aqueous phase.

Clearly, what is needed is a better reactor design and process for the efficient conduct of enzyme-catalyzed conversions. Additionally, many of these disadvantages associated with the enzymatic resolution of water-insoluble esters of chiral carboxylic esters in heterogeneous reaction systems could be minimized or eliminated if the water-solubility of the ester derivative could be substantially increased.

3.0 SUMMARY OF THE INVENTION

This invention relates to novel compositions of matter and their novel methods of preparation. The importance of these compounds resides in their being useful in effecting aqueous enzymatic and homogeneous resolutions of novel racemic esters that are derivatized with substituents that enhance the aqueous solubility of the esters. The novelly prepared racemic esters of this invention are derivatized with sulfate, sulfonate, phosphate and quaternary amine substituents to enhance their aqueous solubility. The novel methods of effecting aqueous enzymatic resolutions of these racemic esters are effected in five ways. In one method the resolutions are effected by placing the enzyme and racemic esters in an aqueous phase wherein one of the ester enantiomers is preferentially and stereospecifically de-esterified. In another method the resolutions are effected by placing the enzyme and racemic esters in an aqueous phase, and contacting this aqueous phase with an organic phase. The preferential and stereospecific de-esterification of one of the ester enantiomers is effected, and the chiral acid product of the deesterification reaction is extracted into the organic phase. In the other three methods the racemic esters are placed in an aqueous phase in contact with one side of a membrane which is contacted with an organic phase on the other side of the membrane, and the preferential and stereospecific resolutions are effected using this membrane apparatus by alternatively placing the enzyme either (1) in the aqueous phase, (2) in association with the membrane, or (3) in the aqueous phase and in association with the membrane; wherein the chiral acid product of the de-esterification reaction is extracted into the organic phase on the other side of the membrane.

4.0 BRIEF DESCRIPTION OF THE FIGURES

This invention may be more readily understood by reference to the following detailed description of the invention and figures, in which FIG. 1 is a schematic representation of a method for the resolution of a racemic mixture of esters, with enhanced aqueous-solubility, in which the mixture fed in an aqueous stream onto one side of a membrane is stereospecifically hydrolyzed by an enzyme that is either 1) in the aqueous phase, 2) associated with the membrane, or 3) in the aqueous phase and associated with the membrane, and the optically enriched organic acid thereby produced is removed by a cocurrent organic process stream fed onto the other side of the membrane; and the unhydrolyzed optically enriched ester is retained in the aqueous stream.

FIG. 2 is a schematic representation of a method for the resolution of a racemic mixture of esters, with enhanced aqueous-solubility, in which the mixture fed in an aqueous stream onto one side of a membrane is stereospecifically hydrolyzed by an enzyme that is either 1) in the aqueous phase, 2) associated with the membrane, or 3) in the aqueous phase and associated with the membrane, and the optically enriched organic acid thereby produced is removed by a countercurrent organic process stream fed onto the other side of the membrane; and the unhydrolyzed optically enriched ester is retained in the aqueous stream.

FIG. 3 is a schematic, cross-sectional view of the membrane in an extractive membrane reactor process described in FIG. 1 and FIG. 2, along with the organic and aqueous process streams in contact with it, for the purpose of illustrating the diffusion and reaction fluxes, as well as the phase partitioning behavior, of the various organic- and water-soluble participants in the reaction process wherein the enzyme is associated with the membrane;

FIG. 4 is a schematic, cross-sectional view of the membrane in an extractive membrane reactor process described in FIG. 1 and FIG. 2, along with the organic and aqueous process streams in contact with it, for the purpose of illustrating the diffusion and reaction fluxes, as well as the phase partitioning behavior, of the various organic- and water-soluble participants in the reaction process wherein the enzyme is in the aqueous phase and associated with the membrane;

FIG. 5 is a schematic, cross-sectional view of the membrane in an extractive membrane reactor process described in FIG. 1 and FIG. 2, along with the organic and aqueous process streams in contact with it, for the purpose of illustrating the diffusion and reaction fluxes, as well as the phase partitioning behavior, of the various organic- and water-soluble participants in the reaction process wherein the enzyme is in the aqueous phase;

Figure 9:
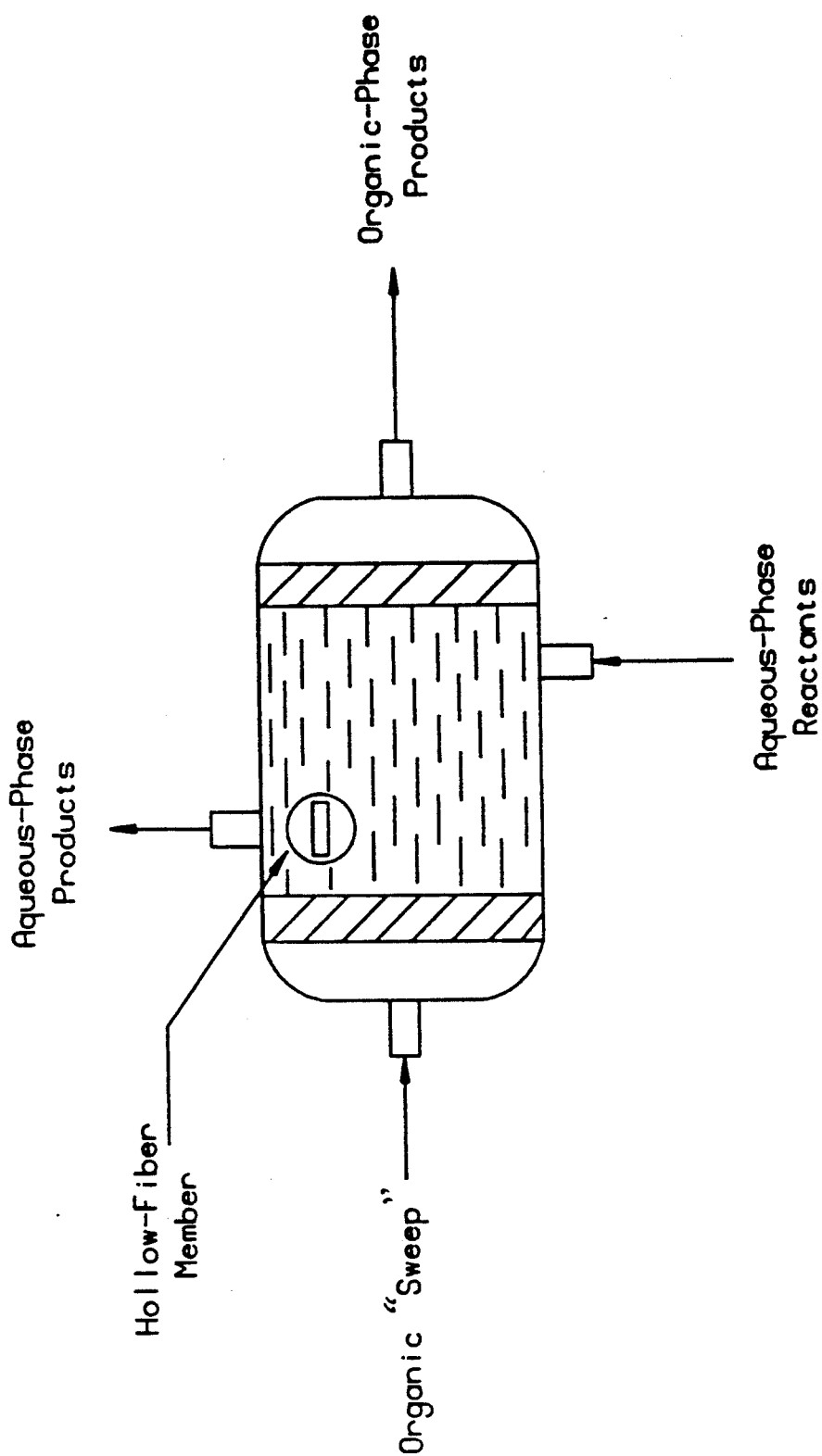
FIG. 9 is a schematic representation of a hollow-fiber extractive enzyme membrane reactor with organic-phase and aqueous-phase feed and product streams being supplied to and removed from the device.
Figure 10:
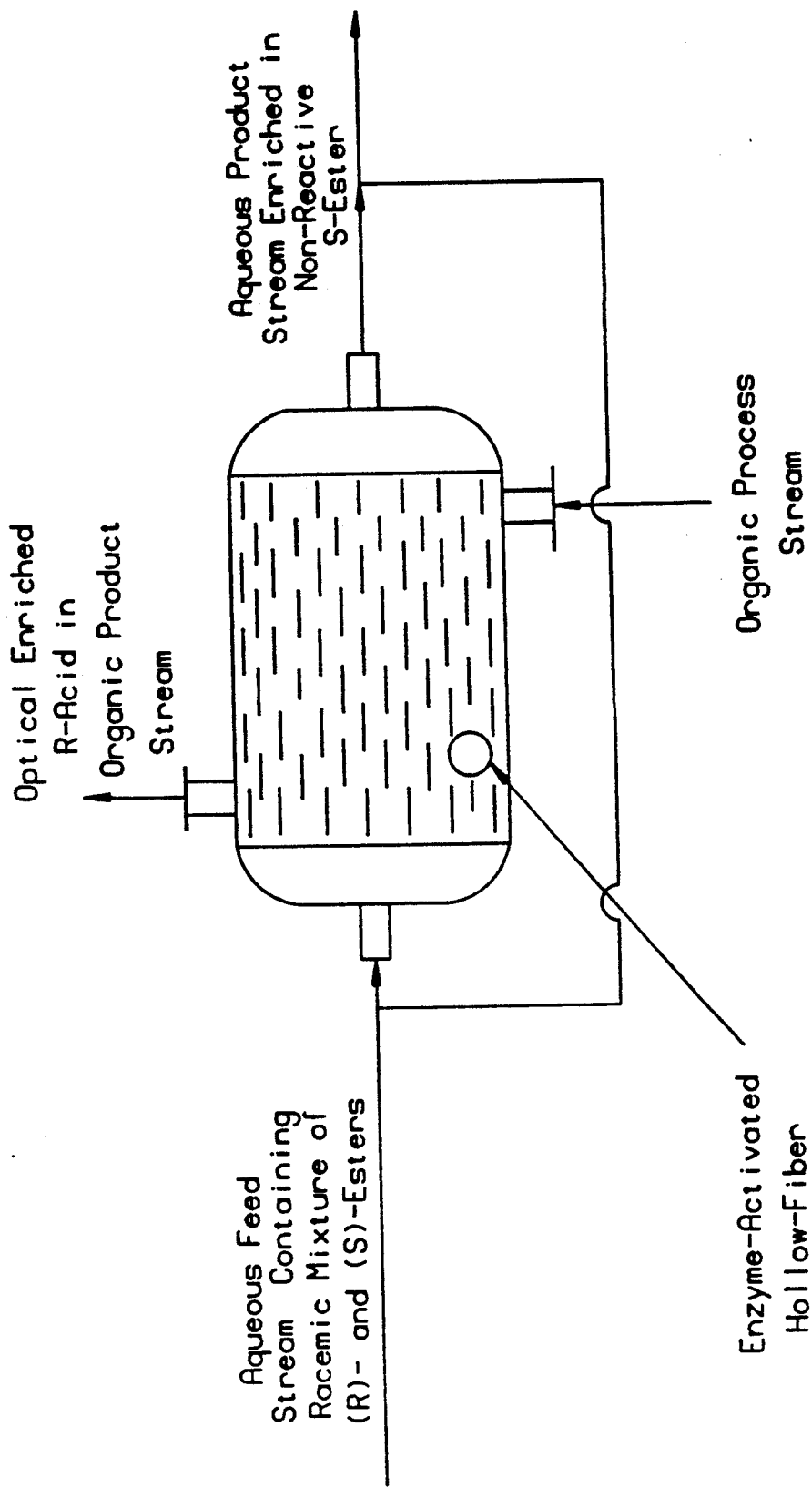
Figure 11:
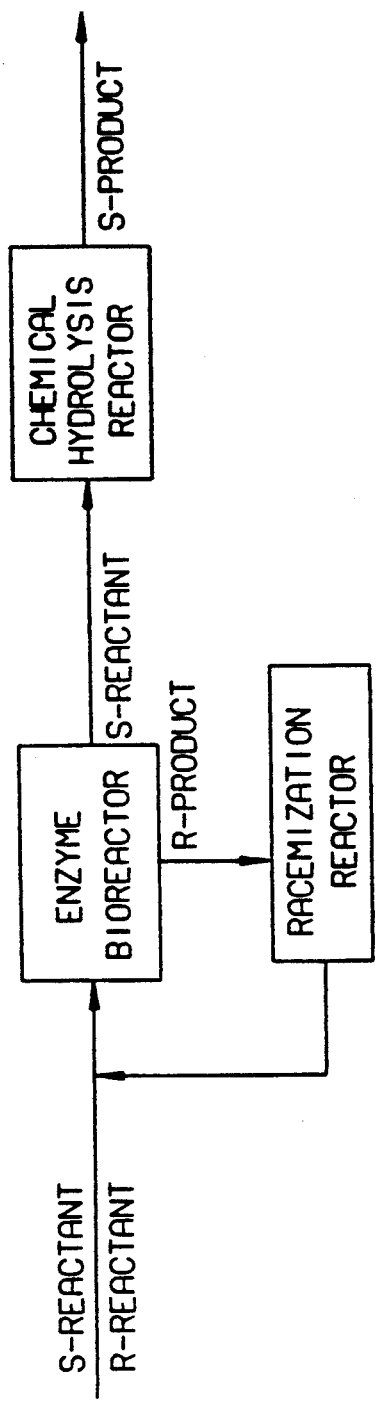
Figure 12:
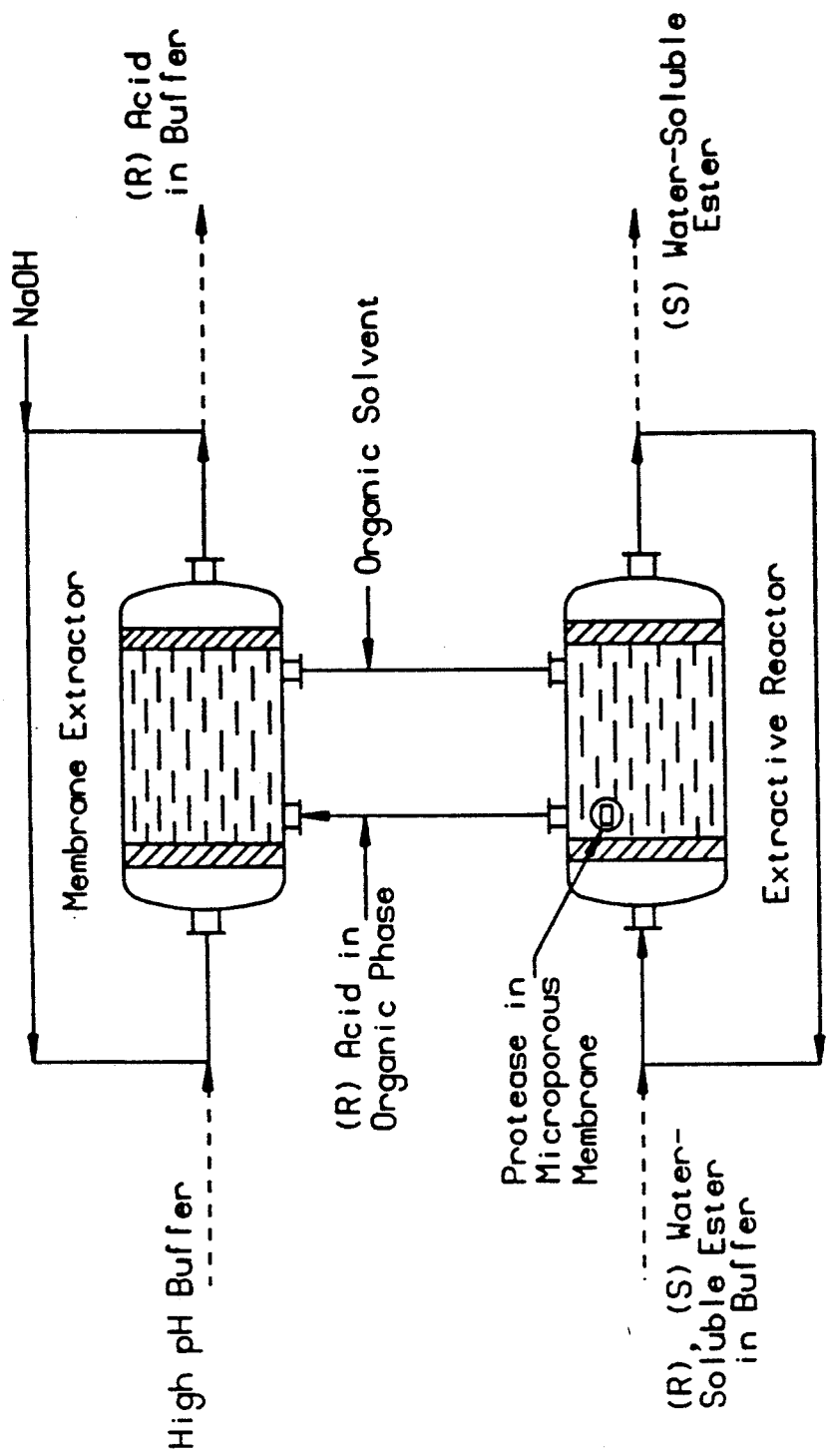

FIG. 10 illustrates how optical resolution of a chiral R-acid is accomplished in the reactor of FIG. 9 by the supply of a racemic mixture of aqueous-soluble esters in the aqueous-phase feed stream and by the removal of aqueous-and organic-phase product streams, enriched respectively in the relatively non-reactive S-ester and in the R-acid, for product inhibited reactions, wherein the materials contained in the organic and aqueous streams are optically purified and exhibit opposite stereochemical configurations; and FIG. 11 shows an example of an integrated enzymatic resolution/reaction/recycle reactor process for the production of singly optically purified products, wherein the resolution is effected to separate the less reactive S-reactant from the reactive isomer R-product whereupon the less reactive isomer can be reacted in a separate reactor to obtain the less reactive isomer product. In addition, the product stream from the enzyme reactor can be recycled after racemization;

FIG. 12 shows an extractive membrane reactor coupled to a membrane extractor. The organic-phase product stream, shown in FIG. 10, is enriched in R-acid. This stream is contacted with an aqueous stream at higher pH than the reactor aqueous stream. The R-acid is extracted into this aqueous solution, and the acid-free organic stream is recycled to the extractive membrane reactor.

Figure 13:
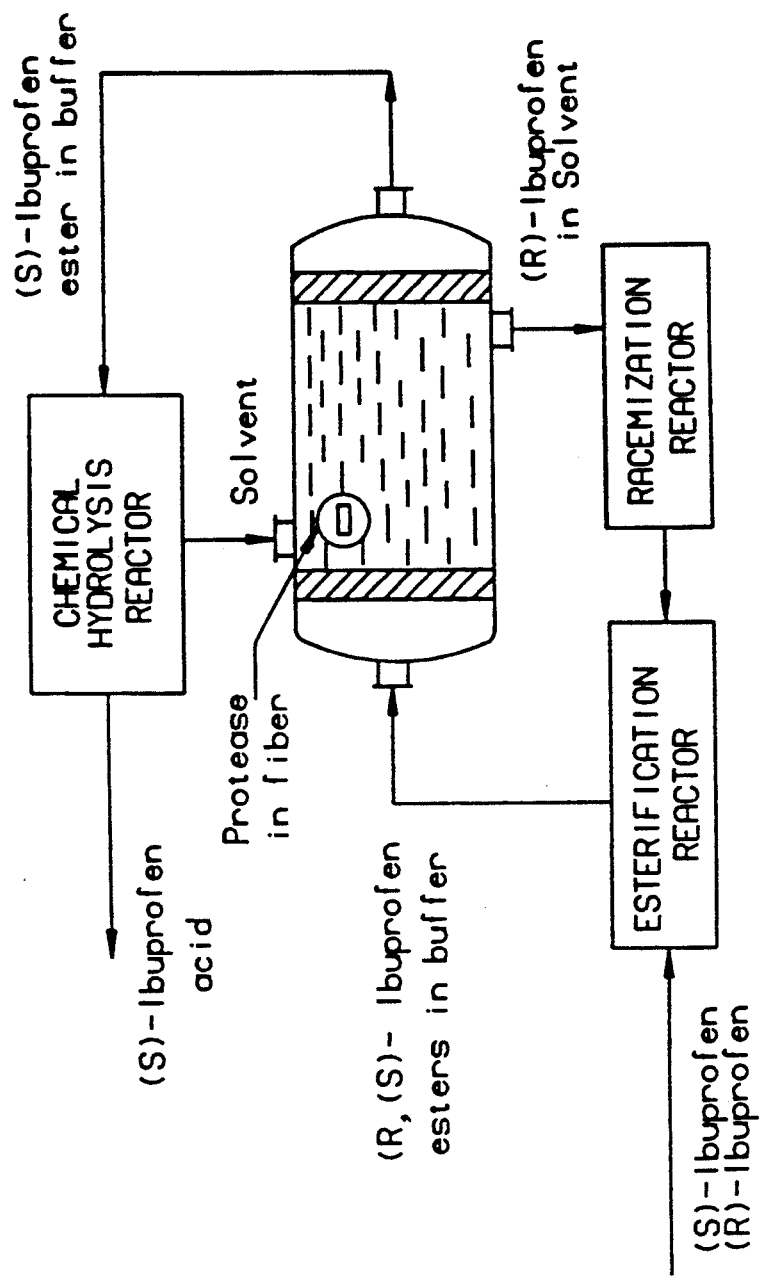

FIG. 13 illustrates an extractive enzyme membrane reactor process for the production of optically purified ibuprofen utilizing an R-selective enzyme, wherein a racemic mixture of an aqueous soluble ester derivative of ibuprofen is fed to the reactor in an aqueous solution, with the resolved R-acid product being removed from the reactor via an organic stream, and the reactive R-acid product being racemized and sent to the esterification reactor, with subsequent recycle to the enzymatic reactor. The unreactive (S)-ester reactant is chemically hydrolyzed to the desired S-ibuprofen acid product.

5.0 DETAILED DESCRIPTION OF THE INVENTION

It is an object of the present invention to render an ester substantially more water-soluble for use as resolution substrates, preferably enzymatic, in a aqueous solution encompassed in 1) a homogeneous aqueous reaction system, 2) a multiphase dispersion extractive reaction, and 3) an extractive membrane reactor. More specifically, ibuprofen and naproxen are two chiral compounds, the enzymatic resolution of which would benefit substantially by the availability of more water-soluble ester derivatives towards which enzymes act with practical activity and stereoselectivity. Embodiments of this invention therefore pertain to compositions of matter which are more aqueous-miscible esters, including the esters of ibuprofen and naproxen, and their preparations. The aqueous-miscibility of the esters is facilitated by the derivatization of the ester moiety with an ionic specie (Table 1). Sulfonate, sulphate, phosphate and quaternary amine derivatives of the ester moiety are the preferred embodiment of the invention.

5.1 ESTERS FOR USE IN AQUEOUS ENZYME-MEDIATED STEREOCHEMICAL RESOLUTION SYSTEMS AND THEIR PREPARATIONS

Generally stated, the preferred embodiment of this invention comprises novel compositions of matter pertaining to a compound of the formula (I),

TABLE 1

SOLUBILITIES OF VARIOUS ESTERS OF IBUPROFEN, NAPROXEN & 2-CHLOROPROPANOIC ACID[1]

| Compound # | Solubility | Compound |
|---|---|---|
| Novel Esters Derivatized with Highly Ionic Groups | | |
| 10 | 2.18 M | Iodide salt of 2-(N,N,N-trimethlammoniumethyl ester of ibuprofen |
| 1 | 1.66 M | Sodium salt of sulfomethyl ester of ibuprofen |
| 4 | 1.13 M | Potassium salt of sulfobutyl ester of ibuprofen |
| 8 | 12.1 mM | Potassium salt of sulfoethyl ester of naproxen |
| 12 | 1.61 M | Methyl sulfate salt of 3-(N,N,N-trimethylammonium)propyl ester of naproxen |

TABLE 1-continued

SOLUBILITIES OF VARIOUS ESTERS OF IBUPROFEN, NAPROXEN & 2-CHLOROPROPANOIC ACID[1]

| Compound # | Solubility | Compound |
|---|---|---|
| Esters Derivatized without Highly Ionic Groups | | |
| | 10 mM | 2-(N,N-dimethylamino)ethyl ester of ibuprofen |
| | 0.18 mM | Methoxyethyl ester of ibuprofen |
| 18 | 0.1–0.2 mM | Methyl ester of naproxen |
| 19 | 0.4 mM | Trifluoroethyl ester of ibuprofen |
| 20 | 1.2 mM | Octyl ester of 2-chloropropanoic acid |

[1]-measured by absorbance of saturated solutions at 262 nm at pH 7 (50 mM phosphate buffer) and room temperature.

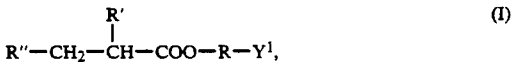

$$R''-CH_2-CH(R')-COO-R-Y^1, \quad (I)$$

wherein R' is selected from the group consisting of aryl, aryloxy, alkyl, hydroxyl, protected hydroxyl and halogen, R is selected from the group consisting of alkyl and aryl, R" is selected from the group consisting of hydrogen, benzyl, protected thiol and thiol, $Y^1$ is selected from the group consisting of a quaternary amine, inorganic acid, and salt thereof.

Alternative embodiments of the invention encompass the compound: 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

Additional embodied derivatives of the ester moiety of the compound in this invention include: 1) a quaternary amine of the formula $-N^+Z_3$, wherein Z is selected from the group of alkyl and aryl, and the counterion to the quaternary amine thereof is selected from the group consisting of halide, carboxylate, inorganic polyatomic ions, methyl sulfate, tosylate, mesylate and trifluoromethylsulfonate; 2) an inorganic acid selected from the group consisting of $-SO_3H$, $-OSO_3H$, and $-OPO_3H_2$, 3) a salt of the inorganic acid selected from the group of anionic species consisting of $-SO_3^-$, $-OSO_3^-$, $-OPO_3^-H$ and $-OPO_3^-$, and from the group of cationic species consisting of alkali metal, alkaline earth metal and ammonium, wherein the alkali metal is selected from the group consisting of sodium and potassium, the alkaline earth metal is selected from the group consisting of magnesium and calcium, and the ammonium specie has the formula $N^+Q_4$, wherein the Q is selected from the group of hydrogen, alkyl and aryl.

Further embodiments of this invention include a compound: 1) wherein R' is 4-isobutylphenyl, R" is hydrogen; and a) R is an alkyl containing up to four carbon atoms and $Y^1$ is the salt of an inorganic acid of the formula $-SO_3^-$; b) R is propyl and $Y^1$ is the salt of an inorganic acid of the formula $-OSO_3^-$; c) R is ethyl and $Y^1$ is the salt of an inorganic acid of the formula $-OPO_3^=$ or $-OPO_3^-H$; and d) R is ethyl, $Y^1$ is the salt of a quarternary amine of the formula $-N^+Z_3$ and Z is methyl; 2) wherein R' is 6-methoxy-2-naphthyl, R'' is hydrogen; and a) R is an alkyl containing up to three carbon atoms and $Y^1$ is the salt of an inorganic acid of the formula $-SO_3^-$; and b) R is an alkyl containing from two to three carbon atoms, $Y^1$ is the salt of a quarternary amine of the formula $-N^+Z_3$ and Z is methyl; 3) wherein R' is a halogen selected from the group consisting of chlorine and bromine, R' is hydrogen; R is propyl and $Y^1$ is the salt of an inorganic acid of the formula $-SO_3^-$; 4) wherein R' is methyl, R'' is a protected thiol protected with a protecting group selected from the group consisting of acetyl and benzoyl; R is methyl and $Y^1$ is the salt of an inorganic acid of the formula $-SO_3^-$; 5) wherein R'' is benzyl, R' is selected from the group consisting of hydroxyl, protected hydroxyl and halogen, wherein the halogen is selected from the group consisting of chlorine and bromine; and 6) wherein R'' is hydrogen, R' is 4-chlorophenoxy; R is methyl and $Y^1$ is the salt of an inorganic acid of the formula $-SO_3^-$.

To prepare the novel compositions of matter an assortment of methods were employed.

Another preferred embodiment of this invention, comprises a method for preparing an ester compound of formula (II),

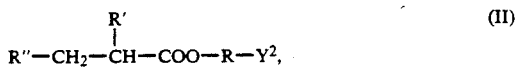
(II)

wherein R' is selected from the group consisting of aryl, aryloxy, alkyl, hydroxyl, protected hydroxyl and halogen, R'' is selected from the group consisting of hydrogen, benzyl, protected thiol and thiol, R is alkyl, $Y^2$ is $-SO_3H$ and salt thereof, comprising:
a) reacting a compound of formula (III),

(III)

wherein R' is selected from the group consisting of aryl, aryloxy, alkyl, hydroxyl, protected hydroxyl and halogen and R'' is selected from the group consisting of hydrogen, benzyl, protected thiol and thiol, with a base to form the carboxylate ion of a compound of formula III,
b) reacting said carboxylate ion of the compound of formula III formed in step a) with hydroxyalkyl sulfonic acid sultone, and
c) isolating the compound of formula II formed in step b), whereby the sulfoalkyl esters of the compound of formula II are prepared.

Alternative embodiments of the method of the invention encompass the compound: 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

Additional embodiments of this method include the base of step a) selected from the group consisting of an inorganic and organic base, wherein the inorganic base is selected from the group consisting of alkali and alkaline earth hydroxides and carbonates.

The method also embodies the reaction carried out in an organic phase, wherein the organic phase is selected from the group consisting of methanol, methylisobutylketone, 2-propanol and mixtures thereof.

The method also embodies the isolation of step c) effected by filtration.

The method also embodies the preparation of a compound: 1) wherein R' is 4-isobutylphenyl, R'' is hydrogen; and a) the reaction proceeds for about 1 hour in methylisobutylketone utilizing the hydroxyalkyl sulfonic acid sultone, 1,3-propane sultone, or b) the reaction proceeds for about 2 hours carried out in boiling 2-propanol utilizing the hydroxyalkyl sulfonic acid sultone, 1,4-butane sultone; 2) R' is 6-methoxy-2-naphthyl, R'' is hydrogen; and the reaction proceeds for about fourteen hours in a solution comprising about 20% methanol and 80% methyl isobutyl ketone solution utilizing the hydroxyalkyl sulfonic acid sultone, 1,3-propane sultone; and 3) wherein R' is chlorine, R'' is hydrogen; and the reaction proceeds for about fourteen hours in methylisobutylketone utilizing the hydroxyalkyl sulfonic acid sultone, 1,3-propane sultone.

In another embodiment of this invention, a method is described for preparing an ester compound of formula (II),

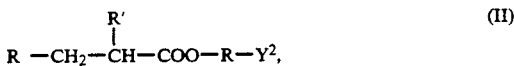
(II)

wherein R' is selected from the group consisting of aryl, aryloxy, alkyl, hydroxyl, protected hydroxyl and halogen, R'' is selected from the group consisting of hydrogen, benzyl, protected thiol and thiol, R is selected from the group consisting of aryl and alkyl, $Y^2$ is $-SO_3H$ and salt thereof, comprising:
a) mixing in trifluoroacetic acid the compound of formula (III),

(III)

wherein R' is selected from the group consisting of aryl, aryloxy, alkyl, hydroxyl, protected hydroxyl and halogen, and R'' is selected from the group consisting of hydrogen, benzyl, protected thiol and thiol, with a compound selected from the group consisting of hydroxyalkyl and hydroxyaryl sulfonic acid salt,
b) adding trifluoroacetic anhydride to said mixture in step a), and
c) isolating the compound of formula II formed in step b), thereby providing an alternative method for preparing esters of the compound of the formula II which are derivatized with sulfonate.

Alternative embodiments of the method of the invention encompass the compound: 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

The method also embodies the preparation of a compound: 1) wherein R' is 4-isobutylphenyl, R" is hydrogen and the hydroxyalkyl sulfonic acid salt of step a) is selected from the group consisting of sodium formaldehyde bisulfite and isethionic acid sodium salt; and 2) wherein R' is 6-methoxy-2-naphthyl, R" is hydrogen and the hydroxyalkyl sulfonic acid salt of step a) is sodium formaldehyde bisulfite.

The preferred embodiment of this invention comprises a method for preparing an ester compound of formula (II),

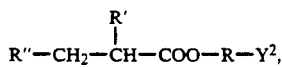
$$R''-CH_2-CH(R')-COO-R-Y^2, \quad (II)$$

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of aryl and alkyl, and $Y^2$ is $-SO_3H$ and salt thereof, comprising:

a) mixing the compound of formula (III),

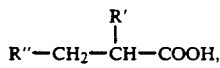
$$R''-CH_2-CH(R')-COOH, \quad (III)$$

wherein R' is selected from the group consisting of aryl, aryloxy, alkyl, hydroxyl, protected hydroxyl and halogen, and R" is selected from the group consisting of hydrogen, benzyl, protected thiol and thiol, with an inorganic acid chloride to form the acid chloride of the compound of formula III in solution, b) reacting said formed acid chloride of the compound of formula III of step a) with a compound selected from the group consisting of hydroxyalkyl and hydroxyaryl sulfonic acid salt, and c) isolating the compound of formula II formed in step b), therein providing a third method for preparing esters which are derivatized with sulfonate.

In this method the inorganic acid chloride of step a) is selected from the group consisting of thionyl chloride, phosphorus trichloride, and phosphorus pentachloride.

Alternative embodiments of the method of the invention encompass the compound: 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

The method also embodies the preparation of a compound: 1) wherein R' is 4-isobutylphenyl, R" is hydrogen and the hydroxyalkyl sulfonic acid salt of step b) is sodium formaldehyde bisulfite; 2) wherein R' is 6-methoxy-2-naphthyl, R" is hydrogen and the hydroxyalkyl sulfonic acid salt of step b) is selected from the group consisting of isethionic acid sodium salt and sodium formaldehyde bisulfite; 3) wherein R' is methyl, R" is a protected thiol protected with a protecting group selected from the group consisting of acetyl and benzoyl and the hydroxyalkyl sulfonic acid salt of step b) is sodium formaldehyde bisulfite; and 4) wherein R' is 4-chlorophenoxy, R" is hydrogen and the hydroxyalkyl sulfonic acid salt of step b) is sodium formaldehyde bisulfite.

An embodiment of this invention also pertains to a method for preparing an ester compound of formula (IV),

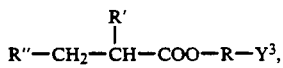
$$R''-CH_2-CH(R')-COO-R-Y^3, \quad (IV)$$

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, $Y^3$ is $-OSO_3H$ and salt thereof, comprising:

a) reacting a compound of formula (V),

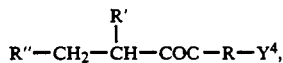
$$R''-CH_2-CH(R')-COC-R-Y^4, \quad (V)$$

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, and $Y^4$ is hydroxyl, in solution with a sulfonating agent, and b) isolating the compound of formula IV formed in step a), whereby esters derivatized with sulfate are obtained Alternative embodiments of the method of the invention encompass the compound 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

The method includes the use of a sulfonating agent of step a) selected from the group consisting of chlorosulfonic acid and $SO_3$.

The method also embodies the preparation of a compound: wherein R' is selected from the group consisting of 6-methoxy-2-naphthyl and 2-(4-isobutylphenyl), and R" is hydrogen. In such a method, R is propyl.

An additional embodiment of this invention, a method is disclosed for preparing an ester compound of formula (VI),

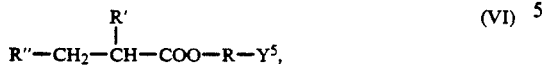

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, $Y^5$ is $-OPO_3H_2$ and salt thereof, comprising a) reacting the compound of formula (V),

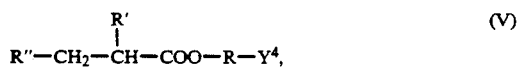

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, and $Y^4$ is hydroxyl, in solution with phosphorylating agent or derivative, and b) isolating the compound of formula VI formed in step a), whereby esters derivatized with phosphate are obtained.

Alternative embodiments of the method of the invention encompass the compound 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

The method also embodies the preparation of a compound: wherein R' is selected from the group consisting of 6-methoxy-2-naphthyl and 4-isobutylphenyl, and R" is H. In such a method, R is ethyl.

In yet another embodiment of this invention, a method is disclosed for preparing a ester compound of formula (VII),

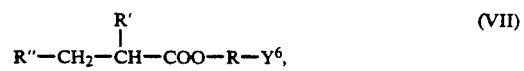

wherein R' is selected from the group consisting of aryl, aryloxy, alkyl, hydroxy, protected hydroxyl and halogen, R" is selected from the group consisting of hydrogen, benzyl, protected thiol and thiol, R is selected from the group consisting of alkyl and aryl, $Y^6$ is $-N^+Z_3$ and salt thereof, and Z is selected from the group consisting of aryl and alkyl, comprising:

a) reacting a compound of formula (III),

wherein R' is selected from the group consisting of aryl, aryloxy, alkyl, hydroxyl, protected hydroxyl and halogen, and R" is selected from the group consisting of hydrogen, benzyl, protected thiol and thiol, with the acid chloride of an inorganic acid to form the acid chloride of the compound of formula III, b) isolating said formed acid chloride of the compound of formula III of step a), c) mixing said acid chloride of step b) with an $Z_2$N-alkanol, to form an ester, d) isolating the formed ester of the compound of formula III of step c), e) reacting said ester of the compound of formula III of step d) with an alkylating agent, and f) isolating the compound of formula VII formed in step e), whereby esters derivatized with quaternary amine are obtained.

The method includes the use of an inorganic acid chloride of step a) selected from the group consisting of thionyl chloride, phosphorus trichloride, and phosphorus pentachloride and an alkylating agent is selected from the group consisting of an alkylhalide, dialkyl sulfate and sulphonic acid alkyl ester.

Alternative embodiments of the method of the invention encompass the compound: 1) wherein the protected hydroxyl is protected with a protecting group selected from the group consisting of alkyl, carbonate, alkyl carbonate, aryl carbonate, acyl, benzyl, mesyl, trityl and tosyl; 2) wherein the protected thiol is protected with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

The method also embodies the preparation of a r compound: 1) wherein R' is 4-isobutylphenyl, R" is hydrogen and the $Z_2$N-alkanol is 2-(N,N-dimethylamino)ethanol; and 2) wherein R' is 6-methoxy-2-naphthyl, R" is hydrogen and the $Z_2$N-alkanol is selected from the group consisting of 2-(N,N-dimethylamino)ethanol and 3-(N,N-dimethylamino)propanol.

5.2 ESTER RESOLUTION REACTIONS

5.2.1 Homogeneous Aqueous Reaction System

The utility of the compounds is demonstrated by their being useful in resolutions of a racemic carboxylic acid (e.g.., ibuprofen or naproxen) accomplished by efficiently contacting, in a homogeneous aqueous solution, a racemic mixture of the more water-soluble ester derivatives of the carboxylic acid with an enzyme that exhibits activity and stereoselectively in the hydrolysis of at least one of the ester stereoisomers.

This novel method for resolving a racemic mixture to produce a resolved preparation of a compound of formula (III),

wherein R' is selected from the group consisting of aryl, aryloxy, alkyl, hydroxyl, protected hydroxyl and halogen, and R" is selected from the group consisting of hydrogen, benzyl, protected thiol and thiol, comprises:
a. enzymatically resolving a racemic mixture of ester compounds of formula (I),

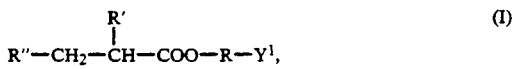

wherein R' is selected from the group consisting of aryl, aryloxy, alkyl, hydroxyl, protected hydroxyl and halogen, R is selected from the group consisting of alkyl and aryl, R" is selected from the group consisting of hydrogen, benzyl, protected thiol and thiol, and $Y^1$ is selected from the group consisting of a quaternary amine, inorganic acid, and salt thereof, by providing in a fluid a racemic mixture of a compound of formula I having at least a first and second stereoisomer, and an enzyme wherein said enzyme catalyzes the reaction of the first stereoisomer into a resolved preparation of a product of formula III having an altered chemical composition, and
b. isolating said resolved preparation of a product of formula III from said fluid.

5.2.2 Extractive Reaction Systems

Many enzyme catalysts suffer when the concentration of reaction products to which they are exposed becomes too high. On the one hand, certain reaction products can be toxic to the enzyme and bring about its reversible or irreversible inactivation or even denaturation. On the other hand, enzymes are often subject to product inhibition, wherein the presence of an appreciable concentration of reaction product(s) slows the rate of its catalyzed production. This feedback or kinetic inhibition is highly desirable in biological systems, since it provides a control mechanism that limits the quantity and concentration of an enzymatic reaction product; however, in industrial applications of enzymes, where large quantities of product at high concentration are desired, this phenomenon of feedback inhibition is a problem to be dealt with and minimized or avoided.

Extractive reaction schemes, (for instance, as presented in co-pending U.S. patent application Ser. No. 033,962 entitled, "Membrane Reactors for Extractive Reactions," and U.S. patent application Ser. Nos. 786,784 and 912,595, both entitled, "Method and Apparatus for Catalyst Containment in Multiphase Membrane Reactor Systems") wherein one attempts to remove an inhibitory product from the reaction zone as soon as it is formed, thereby minimizing its concentration in the vicinity of the enzyme catalyst, represent one strategy for dealing with the undesirable effects of inhibitory product concentrations. In principle, one can selectively remove an inhibitory product from the reaction zone either by extracting the product into a solvent immiscible with the reaction mixture, thereby separating product from catalyst, or by causing the product to permeate selectively across a semipermeable membrane. In the former case, in the specific instance wherein a water-soluble reactant and enzyme catalyst are dissolved in an aqueous reaction phase, it may be possible to disperse a water-immiscible organic solvent in the reaction vessel along with the aqueous reaction phase. If the water-immiscible solvent is chosen such that the product is partitioned into the organic solvent while the unconverted reactant is not, then selective product removal will be accomplished, and product inhibition of the enzyme will be reduced.

5.2.2.1. Multiphase Dispersion Extractive Reaction

Figure 7:
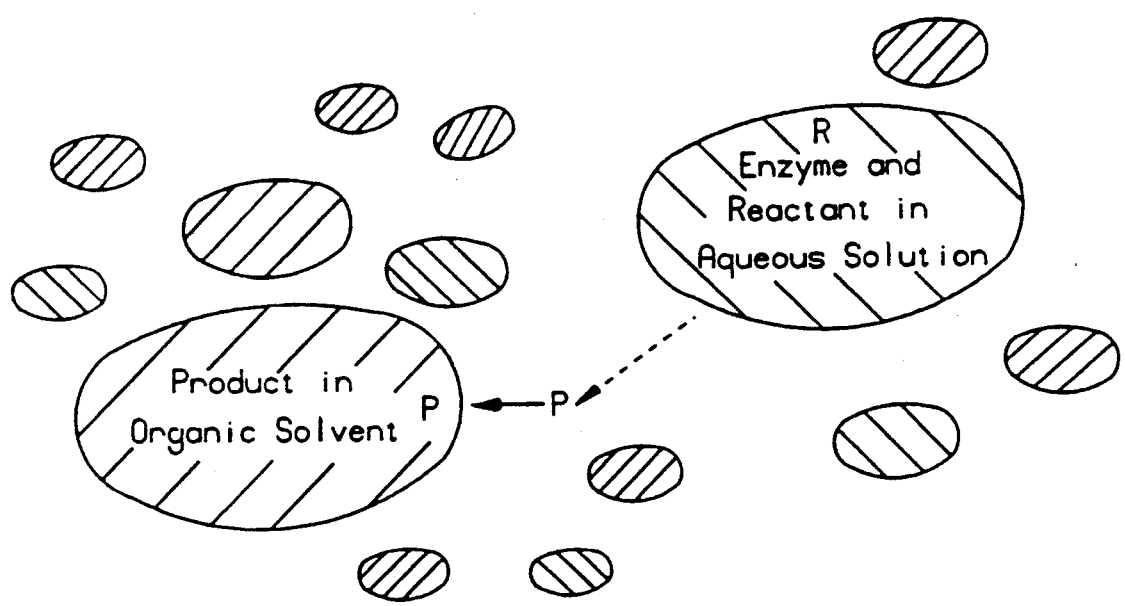
FIG. 7 shows the disposition of the two phases in the multiphase dispersion extractive reaction of this invention.

Additionally, the compounds are useful where the enzymatic reaction product (i.e., the ibuprofen acid) is inhibitory to the enzyme, in which case ibuprofen resolution is effected in a multiphase dispersion of aqueous reactant/enzyme solution with a water-immiscible organic extraction solvent for the inhibitory product. In this manner, the enzyme and racemic substrate (i.e., a racemic mixture of water-soluble ester derivatives of ibuprofen, etc. . . . ) are efficiently contacted with one another in the aqueous reaction phase, while at the same time inhibitory product is selectively removed into the extractant (FIG. 7). The net result is efficient production of one stereochemically enriched isomer of ibuprofen in the aqueous phase (i.e., the less reactive ester in the racemic feed mixture) and of the opposite stereoisomer in the organic extraction phase.

This novel method for resolving a racemic mixture to produce a resolved preparation of a compound of formula (III),

wherein R' is selected from the group consisting of aryl, aryloxy, alkyl, hydroxyl, protected hydroxyl and halogen, and R" is selected from the group consisting of hydrogen, benzyl, protected thiol and thiol, comprises:
a. enzymatically resolving a racemic mixture of ester compounds of formula (I),

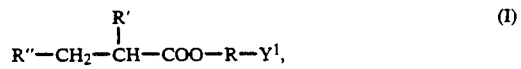

wherein R' is selected from the group consisting of aryl, aryloxy, alkyl, hydroxy, protected hydroxyl and halogen, R is selected from the group consisting of alkyl and aryl, R" is selected from the group consisting of hydrogen, benzyl, protected thiol and thiol, and $Y^1$ is selected from the group consisting of a quaternary amine, inorganic acid, and salt thereof, by providing in a first fluid a racemic mixture of a compound of formula I having at least a first and second stereoisomer, and an enzyme wherein said enzyme catalyzes the reaction of the first stereoisomer into a resolved preparation of a product of formula III having an altered chemical composition; and
b. providing concurrently a second fluid, substantially immiscible in said first fluid, and contacting said second fluid with said first fluid,
whereby said racemic mixture or said first fluid is resolved with said product of formula III of step a) principally diffusing into said second fluid so that said second fluid predominantly includes a resolved preparation of said product of formula III and said first fluid predominantly includes said second stereoisomer of formula I.

5.2.2.2. Extractive Membrane Reactors

In U.S. co-pending application Ser. No. 033,962 (i.e., the multiphase/extractive membrane reactor parent), methods and apparatus are disclosed for the resolution of racemic mixtures and for the enzymatic resolution of optically active organic acids, including ibuprofen and naproxen, and other chiral compounds including many pharmaceuticals, fragrance and flavoring agents, agricultural chemicals (e.g., pesticides and herbicides) and other chemical classes. Stereoselective reactions were described as carried out using enzyme-containing multiphase and extractive membrane bioreactors, multiphase solvent systems, and membrane reactor operating conditions such that the reaction is conducted in an efficient manner and the products are cleanly isolated from the reactants. Depending upon the chiral character of the racemic mixture, the product streams so obtained contain either optically pure compounds or materials substantially enriched in particular isomeric forms.

The membrane in the extractive membrane reactor process of this invention will typically consist of a porous and hydrophilic (i.e., water-wet) membrane, which may be suitably activated by incorporation of an appropriate enzyme within it or on one or more of its surfaces by various means. One surface of this membrane is placed in contact with a first process stream, the feed stream, which stream typically contains a water-soluble or water-miscible substrate for the enzyme. Typically, this aqueous feed stream will contain the reactant in the form of a water-soluble ester derivative of these reactants. In addition, the enzyme need not be in the membrane itself, as it can also be in the aqueous phase.

Concurrently, the second surface of the enzymatically active membrane is contacted with a water-immiscible organic solvent stream, which stream serves to remove inhibitory product from the reaction zone and proximity to the enzyme. When properly operated, the aqueous/organic phase boundary will reside at the surface of the water-wet enzyme-activated membrane that is in contact with the water-immiscible organic product stream, and a substantially aqueous environment will be provided for operation of the enzyme in the hydrophilic, water-wet membrane and/or in the aqueous feed stream mixture. Two inlet (i.e., feed) and two outlet (i.e., product) streams will thus be supplied to and removed from the membrane reactor module and the membrane reactor module will thus necessarily be configured with two inlet and two exit ports. One inlet/outlet pair of these ports will be devoted to the supply and withdrawal of the organic-phase process stream, while the other pair will be dedicated to supply and removal of the aqueous process stream.

With hydrophilic or water-wet membranes, this organic process stream is preferably placed under a small positive pressure relative to the aqueous process stream in contact with the opposite surface of the membrane. This resulting small organic-to-aqueous pressure difference across the membrane serves to prevent the ultrafiltrative flow of a portion of the aqueous process stream across the membrane. At the same time, by operating the process in this manner the organic phase will be prevented from intruding into the pores of the water-wet enzyme membrane by the capillary forces acting at the surface of the membrane in contact with it.

The extractive membrane reactor process of the copending application is useful in the resolution of racemic mixtures and the enzymatic synthesis of chiral products from achiral precursors. This embodiment of the process is particularly appropriate in situations where the enzymatic reaction is inhibited kinetically by modest concentrations of the product. In particular, the extractive membrane reactor addresses limitations of low conversion and catalyst productivity that are associated with bioconversions catalyzed by product-inhibited, feedback-controlled enzymes.

The enzyme-activated membrane of the extractive membrane reactor process will typically be hydrophilic and microporous, contacted on opposite sides with substantially immiscible aqueous and organic process streams. Thus, the enzyme-activated membrane in the extractive membrane reactor process serves both to provide high-surface-area contact between these immiscible process streams as well as to separate them.

In the case of the extractive membrane reactor process, stereoisomers in a racemic feed mixture presented to the enzyme-activated membrane will typically be preferentially water-soluble as opposed to organic-soluble. Accordingly, the feedstream supplied to the extractive membrane reactor process will be aqueous rather than organic. The chiral enzymatic reaction product formed in an extractive membrane reactor process will typically be substantially organic-soluble or even more organic soluble than water-soluble and, thus, it will partition for the most part into the organic process stream and be carried out of the reactor via that stream.

In operation of the extractive membrane reactor process, at least one preferentially water-soluble, organic-insoluble reactant (e.g., a stereoisomer in a racemic mixture) is supplied to the enzyme-activated membrane via an aqueous feed stream. This water-borne reactant subsequently diffuses into the hydrophilic, water-wet membrane, where it encounters an enzyme that stereoselectively catalyzes its conversion to a product, perhaps in conjunction with other coreactants. At least one of the reaction products so produced will exhibit significant solubility in the organic phase. Thus, this species will diffuse to the aqueous/organic interface that is located at the surface of the enzyme-activated membrane in contact with the organic phase, where it will preferentially partition into the water-immiscible organic process stream for subsequent removal from the reactor (FIG. 9).

By virtue of the selective removal of an organic-soluble and inhibitory reaction product into the organic process stream of the extractive membrane reactor process, the enzymatic reaction system is made more productive.

In this fashion, the extractive enzyme membrane reactor process can be employed to efficiently produce stereochemically purified or optically enriched products from racemic and optically inactive feed mixtures, even in situations where the product-inhibited nature of the reaction would preclude the efficient operation of prior-art enzymatic resolution technology.

In three novel methods using the compounds of this invention, a phase-separating membrane is employed in an extractive membrane reactor scheme wherein an inhibitory reaction product is removed from an aqueous reaction phase containing an enzyme and initially racemic mixture of water-soluble ester derivatives. The aqueous reaction phase containing the enzyme in these novel methods pertains to situations where the enzyme is 1) in the aqueous phase, 2) associated with the membrane, or 3) in the aqueous phase and associated with the membrane. Since certain products are known to be inhibitory towards certain enzymes capable of efficiently and stereospecifically catalyzing the hydrolysis of certain of its water-soluble ester derivatives, reaction efficiency can be dramatically improved by extractive reaction as mediated by appropriate membranes. Both hydrophilic and hydrophobic membranes—and passive (i.e., enzyme-excluding) and enzyme-activated membranes—can be used in this manner in the practice of these methods.

The first method pertains to a method for resolving a racemic mixture to produce a resolved preparation of a compound of formula (III), $$R''-CH_2-CH(R')-COOH, \quad (III)$$

wherein R' is selected from the group consisting of aryl, aryloxy, alkyl, hydroxyl and halogen, and R" is selected from the group consisting of hydrogen, benzyl and thiol, comprising:

a. enzymatically resolving a racemic mixture of ester compounds of formula (I), $$R''-CH_2-CH(R')-COO-R-Y^1, \quad (I)$$

wherein R' is selected from the group consisting of aryl, aryloxy, alkyl, hydroxyl and halogen, R is selected from the group consisting of alkyl and aryl, R" is selected from the group consisting of hydrogen, benzyl and thiol, and $Y^1$ is selected from the group consisting of a quaternary amine, inorganic acid, and salt thereof, by providing in a first fluid a racemic mixture of a compound of formula I having at least a first and second stereoisomer to one side of an enzyme activated membrane wherein said enzyme which activates said membrane catalyzes the reaction of the first stereoisomer into a resolved preparation of a product of formula III having an altered chemical composition; and b. providing concurrently a second fluid, substantially immiscible in said first fluid, to the opposite side of said enzyme activated membrane, whereby said racemic mixture of said first fluid is resolved with said product of formula III of step a) principally diffusing into said second fluid from said enzyme activated membrane so that said second fluid predominantly includes a resolved preparation of said product of formula III and said first fluid predominantly includes said second stereoisomer of formula I.

In the second method concerning the use of a membrane, the method pertains to a method for resolving a racemic mixture to produce a resolved preparation of a compound of formula (III), $$R''-CH_2-CH(R')-COOH, \quad (III)$$

wherein R' is selected from the group consisting of aryl, aryloxy, alkyl, hydroxyl and halogen, and R" is selected from the group consisting of hydrogen, benzyl and thiol, comprising:

a. enzymatically resolving a racemic mixture of ester compounds of formula (I), $$R''-CH_2-CH(R')-COO-R-Y^1, \quad (I)$$

wherein R' is selected from the group consisting of aryl, aryloxy, alkyl, hydroxyl and halogen, R is selected from the group consisting of alkyl and aryl, R" is selected from the group consisting of hydrogen, benzyl and thiol, and $Y^1$ is selected from the group consisting of a quaternary amine, inorganic acid, and salt thereof, by providing in a first fluid a racemic mixture of a compound of formula I having at least a first and second stereoisomer, and an enzyme in said first fluid to one side of a membrane wherein said enzyme catalyzes the reaction of the first stereoisomer into a resolved preparation of a product of formula III having an altered chemical composition; and b. providing concurrently a second fluid, substantially immiscible in said first fluid, to the opposite side of said membrane, whereby said racemic mixture of said first fluid is resolved with said product of formula III of step a) principally diffusing into said second fluid from said membrane so that said second fluid predominantly includes a resolved preparation of said product of formula III and said first fluid predominantly includes said second stereoisomer of formula I.

The third method pertains to a method for resolving a racemic mixture to produce a resolved preparation of a compound of formula (III), $$R''-CH_2-CH(R')-COOH, \quad (III)$$

wherein R' is selected from the group consisting of aryl, aryloxy, alkyl, hydroxyl and halogen, and R" is selected from the group consisting of hydrogen, benzyl and thiol, comprising:

a. enzymatically resolving a racemic mixture of ester compounds of formula (I), $$R''-CH_2-CH(R')-COO-R-Y^1, \quad (I)$$

wherein R' is selected from the group consisting of aryl, aryloxy, alkyl, hydroxyl and halogen, R is selected from the group consisting of alkyl and aryl, R" is selected from the group consisting of hydrogen, benzyl and thiol, and $Y^1$ is selected from the group consisting of a quaternary amine, inorganic acid, and salt thereof, by providing in a first fluid a racemic mixture of a compound of formula I having at least a first and second stereoisomer, and an enzyme in said first fluid to one side of an enzyme activated membrane wherein both said enzyme in said first fluid and said enzyme which activates said membrane catalyze the reaction of the first stereoisomer into a resolved preparation of a product of formula III having an altered chemical composition; and b. providing concurrently a second fluid, substantially immiscible in said first fluid, to the opposite side of said enzyme activated membrane, whereby said racemic mixture of said first fluid is resolved with said product of formula III of step a) principally diffusing into said second fluid from said enzyme activated membrane so that said second fluid predominantly includes a resolved preparation of said product of formula III and said first fluid predominantly includes said second stereoisomer of formula I.

More specifically, this method concerns the use of the above process in extractive enzyme membrane reactors for the stereoselective synthesis or resolution of racemic mixtures of water soluble chiral organic esters, including such esters of ibuprofen and naproxen and other chiral compounds in which the membrane supports, entraps, or otherwise contains an enzyme capable of stereoselectively catalyzing a reaction to convert one isomer to a chemically distinct optically active compound. Enzymes are well suited to the role of stereoselective catalysis inasmuch as they contain asymmetric, catalytically active sites in which the molecule being synthesized or undergoing resolution may bind. Because these enzyme active sites are themselves asymmetric, they permit two enantiomers of a given racemic substrate to be acted upon differentially.

For example, many enzymes exist that effectively catalyze the hydrolysis or synthesis of ester and amide chemical functional groups. Many of these enzymes, but not all of them, belong to either one of two main classes of enzymes known as hydrolases or lyases, as defined in the Recommendations of the Commission on Biochemical Nomenclature, Elsevier, Amsterdam, The Nomenclature and Classification of Enzymes (1972) p.17–22. The term E.C. followed by a series of numbers as used herein, provides the identification of an enzyme pursuant to the Commission Recommendations.

Specific examples of such enzymes include, but are not limited to, serine, thiol and carboxy-acid proteases, neutral microbial metalloproteases, other microbial proteases and mammalian peptidases. Specific examples from another class of enzymes include, but are not limited to, fatty acid esterases (E.C. 3.1.1.1), aryl-ester hydrolases (E.C. 3.1.1.2), triacylglycerol acylhydrolases (E.C. 3.1.1.3), and other enzymes that are known to cleave ester and amide linkages.

For example, generally preferred proteases include, but are not limited to, the alkaline proteases from Aspergillus sp. and Bacillus sp.; preferred esterases include, but are not limited to, porcine liver esterase (E.C. 3.1.1.1); and preferred lipases include, but are not limited to, the lipase from *Candida cylindracea* (also known as *C. rugosa*) (E.C. 3.1.1.3). These are preferred because of their ready availability, high stereospecificity and broad substrate range.

Other proteases include, but are not limited to: serine proteases from animal sources, such as α-chymotrypsin (E.C. 3.4.21.1) and Trypsin (E.C. 3.4.21.4), both isolated from bovine and swine pancreas; serine proteases from plant sources; carboxy-acid proteases from animal sources, such as Pepsin (E.C. 3.4.23.1), Chymosin (E.C. 3.4.23.4), and Carboxypeptidase A (E.C. 3.4.17.1): serine proteases from microorganisms, generally referred to as subtilisins (E.C. 3.4.21.14) but isolated from a variety of microorganisms, including naturally occurring specie and genetically manipulated specie, of such microorganisms as *Bacillus subtilis, Bacillus amyloliquefaciens, Bacillus amylosaccharicus* and *Bacillus licheniformis*; serine proteases from Aspergillus sp., such as *Aspergillus oryzae* and *Aspergillus flavus*, which may be classified as subtilisins but may also be called Aspergillus alkaline proteases; microbial metallo-neutral proteases (E.C. 3.4.24.4) isolated from a variety of sources such as *Aspergillus oryzae*, Bacillus sp. and *Streptomyces griseus*; and other microbial proteases (E.C. 3.4.23.6) isolated from sources such as the genera Aspergillus, Bacillus, Mucor, Penicillium, Pseudomonas, Rhizopus, Serratia, Staphylococcus. Streptococcus, Streptomyces and Tritirachium. Proteases isolated from mammalian blood, pancreas, spleen, submaxillary glands and gastrointestinal mucosa may also be used.

Other lipases include, but are not limited to, those isolated from micro-organisms, such as *Pseudomonas aeruginosa, Pseudomonas flourecens, Rhizopus arrhizus, Rhizopus delemar, Rhizopus niveus, Rhizopus oryzae, Rhizopus japonicus, Chromobacterium viscosum, Geotrichium candidum, Aspergillus niger, Aspergillus solae, Aspergillus oryzae, Mucor miehei, Achromobacter lipolyticum,* Alcaligenes sp., Arthrobacter sp. and *Candida lipolytica*. Pancreatic lipases from various mammalian species and lipase derived from wheat germ may also be employed. Other esterases derived from mammalian sources include, but are not limited to, carboxyl esterase (E.C. 3.1.1.1., carboxypeptidase A (E.C. 3.4.17.1), acetyl cholinesterase (E.C. 3.1.1.7), pepsin (E.C. 3.4.23.1) and trypsin (E.C. 3.4.21.4). Other microbial sources include Bacillus thermoproteolyticus (for thermolysin), *Bacillus amyloliquefaciens* and *Streptomyces griseus* as well as papain (E.C. 3.4.22.2) derived from Papaya sp.

Depending upon the source, lipases and esterases have a working pH range from about 2 to about 10, with their optimum pH generally falling between 5.0 and 8.5. The temperature range for most enzymes takes place from about 15 to 70° C., with the enzymes usually performing most effectively in the range from about 20°–45° C.

In addition to isolated and purified enzymes, it should be noted that the processes of the present invention may also be carried out employing relatively impure and/or heterogeneous enzyme preparations, such as those derived from cell extracts, cell lysates, partially purified enzyme isolates and whole cells, albeit at some reduction in the enzymatic activity. Enzyme can also be immobilized on solid, non-membrane supports by conventional means; such as, covalent binding, adsorption, matrix entrapment, ion-exchange, or microencapsulation. Indeed, enzymes contained within whole cells, whether viable or not, may also be used in the practice of this invention, and accordingly it is intended that the term "enzyme" as used herein is meant to broadly include biocatalytic enzymes in all of these forms.

In particular, it is desired to prepare chiral compounds and precursors or derivatives thereof, by the process of the present invention, wherein the enzymatic resolution of a racemic mixture of chemically synthesized enantiomers is effected. These compounds include, but are not limited to, the following: naproxen or 2-(6-methoxy-2-naphthyl)propanoic acid; ibuprofen or 2-(4-isobutylphenyl)propanoic acid; ketoprofen or 2-(3-benzoylphenyl)propanoic acid; flurbiprofen or 2-(2-fluoro-4-biphenylyl)propanoic acid; 2-halopropanoic acids, such as 2-chloropropanoic acid and 2-bromopropanoic acid; 2-aryloxypropanoic acids, such as 2-(4-chlorophenoxy)propanoic acid, 2-(2-methyl-4-chlorophenoxy)propanoic acid, 2-(4-hydroxyphenoxy)propanoic acid; 2-methyl-3-thiolpropanoic acid and thiol-protected derivatives thereof, 2-hydroxy-4-phenylbutanoic acid and hydroxyl-protected derivatives thereof; 2-halo-4-phenylbutanoic acid, such as 2-bromo-4-phenylbutanoic acid; and esters thereof.

The chemical nature (e.q., identity of functional groups) of many particular reactants and products will be evident from the above partial lists of reaction categories, reactions and products. It will be appreciated from these lists that these reactions fall into the class of: water-soluble, substantially organic-insoluble reactants are converted to either water-soluble and/or organic-soluble product species. Such types of reactions are particularly suited for conduct in aqueous homogeneous, extractive dispersion and extractive membrane reactor processes, respectively. Multiphase dispersion and membrane-based extractive reaction processes will be particularly preferred when the product species is organic-soluble and inhibitory to the enzyme. As an example of the reactions, esters that are soluble in water may be hydrolyzed to acids in the noted processes, with said acids being either predominantly water-soluble or organic soluble depending on the pH of the aqueous phase, the nature of the organic solvent and the partitioning behavior of said acids. The corresponding alcoholic co-product will typically be preferentially soluble in the aqueous phase. In this case, the unreacted ester isomer is also retained in the aqueous phase, while an organic solvent can be employed to remove the acid deesterfication product in instances where that product is inhibitory to the enzyme.

In aqueous homogeneous, extractive dispersion, or extractive membrane processes, the stereoselective enzymatic reaction may be conducted using the racemic form of the desired chemical derivative as the reactant mixture. In particular, the enzymatic resolution of a racemic mixture of the esters can be effected by the stereoselective enzymatic hydrolysis of the racemic mixture of ester derivatives to the desired product. Specifically, ester derivatives utilized are selected to manipulate the water-solubility of the ester derivatives as well as to maximize the enzyme activity and the stereoselectivity towards the derivatives. Ester derivatives of acids such as ibuprofen and naproxen which are useful in the resolution processes include, but are not limited to, compounds represented by the formula (I) where the group of $Y^1$ can correspond to a $-SO_3^-$ (sulfonate), $-OSO_3^-$ (sulfate), $-OPO_3^=$ (phosphate), $-O-PO_3^-H$ (monohydrogen phosphate) or $-N^+Z_3$ (quaternary amine) wherein Z is methyl but is not limited to methyl, respectively.

Alternatively, the novel method encompasses the utilization of the compound: 1) wherein the hydroxyl group is derivatized with a protecting group selected from the group consisting of alkyl, carbonate, alkyl carbonate, aryl carbonate, acyl, benzyl, mesyl, trityl and tosyl; 2) wherein the thiol is derivatized with a protecting group selected from the group consisting of acetyl, benzoyl and thiocarbamoyl; 3) wherein the aryloxy group is selected from the group consisting of 4-hydroxyphenoxy, 4-chlorophenoxy and 2-methyl-4-chlorophenoxy; and 4) wherein the halogen is selected from the group consisting of chlorine and bromine.

Such esters derivatives of chiral acids may be resolved directly by feeding racemic mixtures thereof directly to the aqueous homogeneous, extractive dispersion or extractive membrane reactor processes.

In the aqueous homogeneous reaction process, which is one method for using the compounds, the racemic reactant mixture and enzyme will typically be charged in aqueous solution to a reactor vessel (e.g., a continuous stirred-tank reactor or packed bed reactor). The reactor will optionally be provided with means for pH control, agitation, and valving and piping for charging and discharging the vessel, in either a batch-wise, semi-continuous, or continuous manner. Once the enzymatic reaction has proceeded to the desired degree of completion, the desired isomeric products (i.e., the unconverted ester reactant and the acidic product of the hydrolysis reaction) may be separated from the enzyme and each other by conventional means.

The difference in solubilities of key reactants and products in the aqueous homogeneous, extractive dispersion, or membrane reactor schemes will be seen typically to result from the conversion of a relatively aqueous soluble and charged functional group [e.g., an ester (derivatized with a sulfonate, sulfate, phosphate or quaternary amine group)] to a more non-polar and/or less completely charged functional group (e.q., a weaker carboxylic acid) that is more readily extractable into organic solvents.

Typically, but not necessarily, the partition coefficients, i.e., the ratios of organic-phase to aqueous-phase species concentrations at phase equilibrium, or aqueous-to-organic phase concentration ratios, will exceed two for key reactants and products, and preferably the distribution ratios of the key components will exceed about 10 for optimum performance of extractive dispersion and extractive membrane reactor processes. For reactants that are the salts of strong acids, (e.g., the sulfonate, sulfate and phosphate ester derivatives), partition coefficients will be insensitive to pH and the organic-phase solubility of these compounds will be very low. However, the partition coefficients of carboxylic acid reaction products will be dependent on pH, at least for pH values near or above the $pK_a$ value of the acid. Under ideal circumstances, partition coefficient ratios can exceed 20 or more, leading to very efficient reactor operation and reactant/product stereoisomer separations, but such extreme solubility differences are not required in order to practice the invention.

Absolute solubilities of reactants and products in the aqueous and organic-based phases are important to the practice of the present invention, with both the extractive dispersion and extractive membrane reactor process embodiments, since reactants with enhanced aqueous solubilities are more susceptible to the aqueous mediated resolutions. The enhanced solubilities of reactants of the preferred embodiment of this invention are noted in Table 1.

Solvents that have been found useful for extraction of inhibitory reaction products include but are not limited to aliphatic and aromatic hydrocarbons such as hexane, cyclohexane, xylenes and toluene; chlorinated solvents such as methylene chloride and chloroform; water-immiscible alcohols including amyl alcohol, octanol and decanol; esters including amyl acetate and butyl acetate; ethers such as tert-butyl methyl ether; and ketones such as methyl isobutyl ketone. In choosing a solvent for use in the extractive dispersion or extractive membrane reactor processes, important considerations include its compatibility with the membrane material and enzyme, as well as its toxicity, viscosity, solubility and miscibility characteristics, a its ability to be readily separated from other reaction components.

In the novel multiphase-dispersion extractive reaction process method, the racemic reactant mixture and enzyme will again be charged in aqueous solution to a reactor vessel (e.g., a continuous stirred tank reactor, packed bed reactor, fluidized-bed reactor or other type of equipment used in contacting aqueous and organic phases in solvent extraction operations). In this method, an organic solvent will also be charged to the reaction vessel, and the aqueous and organic phases will be brought into high-surface-area contact by vigorous agitation and dispersion by mechanical agitation, with the organic solvent extracting inhibitory reaction product from the aqueous reaction phase. Following reaction, the aqueous and organic phases are separated from one another by conventional means, and the respective water- and organic-soluble stereoisomers can then be isolated from these two phases.

Enzyme-activated membranes suitable for the practice of the novel extractive membrane reactor process using the novel compounds will be chosen with several considerations in mind, namely, chemistry, morphology and mode of enzyme activation. With regard to the first of these, the membrane material must be such that it will not be deleteriously effected (e.g., swollen or chemically attacked) by any of the ingredients in the reaction system and, in particular, by organic reactants, products and/or solvents. Although membranes comprised of inorganic materials (e.g., ceramics) can be used in the practice of this invention, polymeric membranes represent a preferred embodiment. In particular, membranes fashioned from solvent-resistant polymers are well suited to the present process. Typical polymeric materials that can be fabricated into suitable membranes for the practice of this invention include but are not limited to regenerated cellulose, the esters of cellulose (and particularly preferred the partial acetate and nitrate esters), polyacrylonitrile and copolymers thereof (especially the hydrophilic ones including but not limited to copolymers incorporating acrylamide, acrylate, acrylate esters and/or methacrylate functionalities), polyurethane-containing copolymers, the polyarylsulfones and polyarylethersulfones (including polysulfone, polyethersulfone and blends thereof with such hydrophilic copolymers as polyethyleneoxide, polyhydroxyethers, polyethyleneglycol, polyvinylalcohol, polycaprolactone and polyepihalogenohydrins), polyvinylidene fluoride, polytetrafluoroethylene, polyvinylalcohol, aliphatic and aromatic polyamides, polyimides, polyetherimides, polyesters, polycarbonates, polyolefins such as polypropylene and polyvinylchloride, polybenzimidazole and polybenzimidazolone.

The enzyme component of the enzyme-activated membrane will typically function most effectively in an environment that is predominantly aqueous, and for this reason it is preferred that the membrane be water-wet or hydrophilic if enzymatic reaction is to occur within the membrane. Certain of the above membrane polymers are intrinsically hydrophilic (e.q., the cellulosics, many polyacrylonitrile copolymers and the polyamides). However, even those which are not intrinsically hydrophilic may be rendered suitable for the practice of applying this novel method by an appropriate chemical or physical surface treatment (e.g., by derivatization or attachment of hydrophilic functional groups or simply by contact with an appropriate surfactant), by coating the pore wall surfaces of hydrophobic polymers with hydrophilic materials, or simply by filling the pore volume of an asymmetric, microporous membrane with hydrophilic enzyme in the form of a high-water-content gel.

Membranes suitable for use as enzyme supports can exhibit one of several morphologies. In particular, they may be microporous membranes of the type generally employed in microfiltration processes, wherein the pore sizes will typically range from a few hundredths of micron to several microns, and pore void volumes range from a few percent to 90% and greater. Such microporous membranes may be isotropic (i.e., with no significant variation in pore size from one external surface to the other), or they may exhibit some degree of anisotropy. Ultrafiltration membranes are also useful in the practice of the method. They are typically highly asymmetric, and characterized by a very thin skin with effective pore sizes in the range of approximately from 1 to 20 nm residing atop a much thicker but more highly porous substrate region comprised of much larger pores. Additionally, gel-type dialysis membranes (e.g., regenerated cellulose membranes of the type used in hemodialysis) may also be employed, particularly where the enzyme is located at the surface of the membrane. Such membranes may be surface-activated either by covalent attachment of the enzyme to an exterior surface or by formation of a dynamic enzyme gel-polarized "secondary membrane" layer at one surface.

In addition, the membrane is largely microporous, characterized by a relatively thick, high-void-volume, finely porous spongy substrate region, but it possesses an ultrafiltration-type skin at one external surface. Such membrane morphologies offer high enzyme loadings and facilitate periodic enzyme replacement. The use of skinned microfiltration membranes with this morphology is described below in connection with modes of activation of membranes with enzymes.

Figure 8:
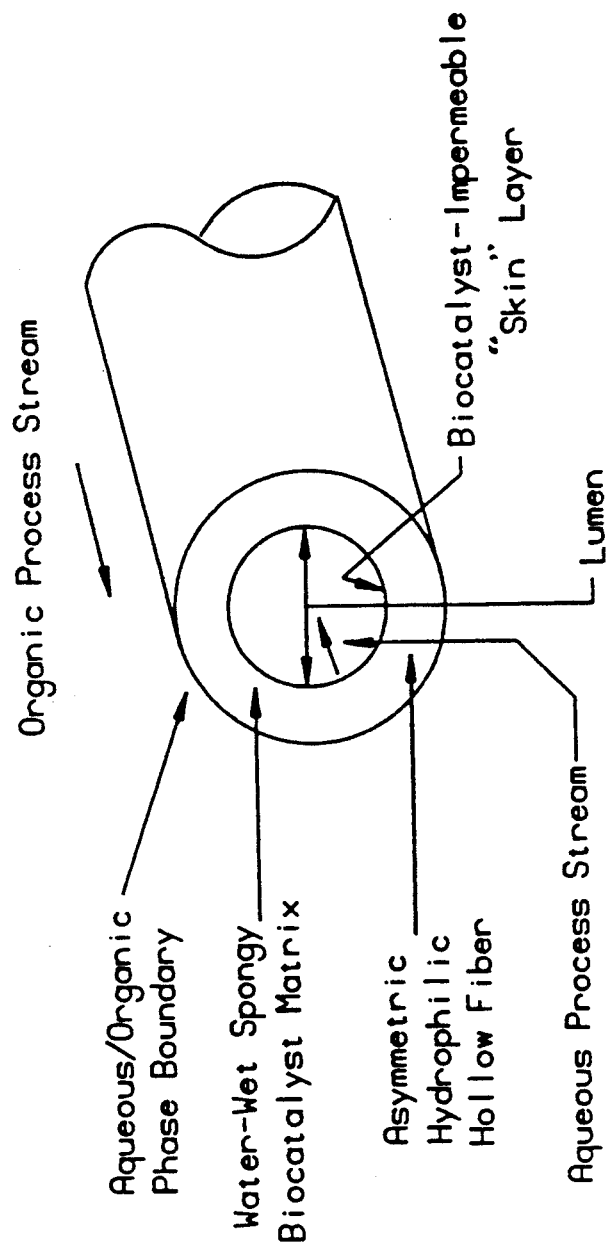
FIG. 8 is a schematic representation of a preferred embodiment of the invention wherein the enzyme is reversibly contained within an asymmetric, hydrophilic, and microporous hollow-fiber membrane.

The geometry of the membrane employed in the extractive membrane reactor embodiment of this novel method is a secondary consideration, and membranes in the forms of flat sheets, tubes preferably of large-diameter, and hollow fibers of various diameters are all useful (FIG. 8). Since it is essential that the membrane module have two inlet and two outlet ports, plate-and-frame or cassette-type housings are preferred for packaging flat-sheet membrane over spiral-wound cartridges, whereas tubular and hollow-fiber membranes are efficiently packaged in cylindrical multitube or multifiber membrane modules, the construction of which resembles that of a shell-and-tube exchanger. Membranes in the form of hollow-fiber modules permit large areas of membrane to be packaged tightly and economically.

By virtue of the containment, entrapment, or immobilization of enzyme within the membrane phase, any leakage of enzyme out of the membrane and into either the aqueous or organic process streams may be substantially prevented. Suitable means of enzyme incorporation include but are not limited to containment within the pore spaces of asymmetric (i.e., skinned), microporous membrane structures, adsorption on membrane pore wall surfaces, encapsulation or entrapment in polymeric gels within membrane pores, covalent coupling to membrane pore walls and crosslinking of enzyme, either within the pore spaces or adsorbed on membrane pore wall surfaces. In addition, the enzyme can be immobilized on a particulate, solid-phase support and that immobilized enzyme can be contacted with the aqueous fluid.

More particularly, a number of alternatives exist for the activation of membranes with enzymes. The most straightforward approach involves covalently linking the enzyme to the exterior or interior (i.e., pore wall) surfaces of membranes via any of a number of conventional enzyme immobilization chemistries developed for attaching biocatalysts to non-membrane supports. [See: Zaborsky, O.R., *Immobilized Enzymes*, CRC Press, Cleveland, Ohio (1973); Weetal, H. H., *Immobilized Enzymes. Antigens, Antibodies, and Peptides: Enzymology*, Vol. 1. Marcel Dekker, N.Y. (1975); Emery, A. et al., Biotechnol. Bioeng., 16:1359 (1974)]. Enzymes may also be crosslinked in porous membranes [Thomas, D. and S. R. Caplan, pp. 351–398 in *Membrane Separation*

Processes, P. Meares, ed., Elsevier, Amsterdam (1976)], entrapped in membrane gels [Blaedel, W. J. et al., Anal. Chem., 44:2030 (1972)], encapsulated, or adsorbed on or within membranes via ion-exchange or other specific or non-specific protein-surface interactions. It is also forseeable that in the practice of this method it will prove effective in some cases to combine the above techniques. For instance, enzyme may first be adsorbed on membrane exterior or pore wall surfaces, subsequently to be anchored more positively by crosslinking the adsorbed enzyme layer in place.

In addition, the enzyme will be reversibly contained in a skinned, microporous membrane as described in the co-pending U.S. patent application Ser. No. 912,595, filed Oct. 1, 1986, and which is incorporated herein by reference. Such a membrane structure, shown in FIG. 8, is capable of entrapping the enzyme between two boundaries that it cannot cross under normal membrane reactor operating conditions. These two barriers consist of (1) the "skin" or surface layer of the enzyme-activated membrane, which contains pores that are sufficiently small so as to prevent the transport and leakage of macromolecular enzyme from the porous interior of the membrane to the aqueous process stream in contact with it and (2) the aqueous/organic phase boundary at the opposite membrane surface which, by virtue of the insolubility of most enzymes in organic solvents, prevents the enzyme from partitioning into and thus escaping from the membrane via the organic process stream. Such a membrane may be activated with enzyme by ultrafiltering an aqueous solution of enzyme through it, with very high loadings of active enzyme incorporated into porous membranes in this manner. An additional benefit of this mode of enzyme activation is its reversibility. That is, deactivated enzyme may simply be removed from the membrane by a back-flushing operation, thus facilitating the periodic replenishment of the enzyme catalyst. In addition, the resolution method further comprises separating the enzyme from remaining stereoisomers in said first fluid by a method selected from the group of ultrafiltration, dialysis, diafiltration, precipitation and ion-exchange.

An alternative preferred approach to enzyme activation of membranes for use in the extractive membrane reactor processes relies on the formation of dynamic enzyme-gel-polarized membranes atop the surface of ultrafiltration or gel-type membranes of the type used, for example, in hemodialysis and hemofiltration. Dialysis/ultrafiltration membranes comprised of regenerated cellulose or hydrophilic polyacrylonitrile-based polymers and copolymers are particularly preferred. Although such membranes are finely porous and hence water-permeable, the effective surface pore size of membranes suitable for use here are too small to admit enzymes. However, it has been demonstrated [Kerkhof, P.I.A.M., et al., "Enzymatic Hydrolysis of Lipids in a Membrane Reactor," a poster presented at the International Membrane Technology Symposium, Lund, Sweden, May 28-30, 1985; Molinari, R. and E. Drioli, Proc. Nat. Congr. Ind. Chem. Div. Sci., Siena, June, 10-25 1985] that such membranes can be effectively coated with enzymes by the simple expedient of ultrafiltering an aqueous enzyme solution across the membrane, thus leaving a concentrated enzyme gel layer deposited on one surface of the membrane film or fiber. If the organic process stream is subsequently brought into contact with the surface of the membrane so activated, the enzyme gel layer will tend to remain in place at the membrane surface, inasmuch as the enzyme is not appreciably soluble in organic solvents. In a refinement of this technique, we have further stabilized the enzyme surface layer or "dynamically formed membrane" by chemically crosslinking the enzyme protein.

In addition, the novel method, as it pertains to extractive membrane reactors employs these membranes to mediate the enzymatic resolution outside of the membrane structure rather than having the enzyme associated with the membrane. Additionally, in yet another extractive membrane reactor, the enzyme can be in the aqueous phase which is associated and not associated with the membrane for the greatest extent of enzymatic resolution.

More particularly, in this last resolution method, wherein the resolution occurs within the aqueous phase associated and not associated with the membrane, one mode of operation is conducted by dissolving the enzyme into the aqueous phase (first fluid). The water-wet portion of the membrane is accessible to the enzyme solution in this embodiment. A microporous membrane with a finely spongy matrix or a high-molecular-weight-cutoff ultrafiltration membrane (i.e., with a cutoff higher than the enzyme molecular weight or size) will allow the enzyme to enter the membrane along with the aqueous fluid. Enzymatic reaction will occur in the aqueous first fluid that is circulating past the membrane surface (i.e., fluid not associated with the membrane) and in the aqueous solution present within the membrane interior (i.e., fluid associated with the membrane).

Where the aqueous first fluid contains the enzyme, and within which said enzyme catalyzes the reaction, the enzyme is excluded from entering the membrane by various modes of action. One mode of action is size exclusion. A tight, gel-type, dialysis membrane like regenerated cellulose will reject macromolecules such as proteins and enzymes. A low molecular weight cut-off, ultrafiltration membrane (i.e., with a cutoff lower than the enzyme molecular weight or size) will also exclude the enzyme from the interior of the membrane. Finally, another mode of action is solubility. A hydrophobic membrane will preferentially be wet by the organic phase. The enzyme is excluded from the membrane interior by virtue of the low solubility of enzymes in most water-immiscible, organic solvents. An organic-wet membrane must be operated in the opposite manner as water-wet, hydrophilic membranes, such that a small aqueous-to-organic pressure difference across the membrane is maintained at all times. This pressure differential serves to prevent ultrafiltrative flow of the organic phase through the membrane.

In these various process methods, once the enzymatic reaction has taken place, the aqueous stream (or first fluid in the case of the extractive reaction processes) contains the enzyme as well as the unreacted (second) stereoisomer. Typically, the processes of the novel method will include means for an enzyme/unconverted isomer separation. Enzyme removal from the isomer solution can be achieved by techniques known to those skilled in the art; such as, ultrafiltration, diafiltration, dialysis, precipitation or adsorption. The unconverted isomer can be separated from the enzyme by altering the isomer's water solubility by chemical or environmental techniques (e.g., adding salts, reducing the temperature or adjusting the pH). Chemical conversion of the enzyme-inactive isomer to produce the corresponding chiral acid can be effected by a non-enzymatic hydrolysis reaction which takes place at a temperature from about 20° to 80° C. and the pH ranges from about 10 to about 14. Once the separation is completed, the enzyme can be recycled to the reactor vessel and the isolated isomer can be further processed.

5.2.3 Reaction and Resolution Process Parameters

In operation of the extractive membrane reactor processes, two process solutions, one aqueous (or first fluid) and the other consisting of a water-immiscible organic liquid or solution (or second fluid), are brought into contact with a membrane which optionally may be enzyme activated. Usually it is preferred that the enzyme-activated membrane be hydrophilic and thus wet by the aqueous phase in contact with it, since enzymes are typically more effective in aqueous environments than they are in organic solvents. Where the membrane is, in fact, water-wet, the fluid streams on either side of the membrane are preferably maintained at slightly different pressures such that a small positive pressure difference exists across the membrane, with the organic phase held at the greater pressure (e.g., by means of a back-pressure regulator or some other pressure control device).

When operated in this manner, the aqueous/organic phase boundary will be located at the surface of the membrane in contact with the organic process stream, and this location will be a stable one. Ultrafiltration of aqueous solution across the membrane will be prevented by the opposing pressure difference (i.e., organic-to-aqueous), but the hydrophilicity of the membrane will ensure that the membrane is preferentially wet by the aqueous phase. The principal restriction on the magnitude of the organic-to-aqueous pressure difference (other than the requirement of mechanical membrane strength) is that it not exceed the intrusion pressure for penetration of membrane pores by the non-wetting organic phase, said intrusion pressure P being estimable from the Young-LaPlace equation as follows:

$$P = (2 \times \gamma / R_{pore}) \times \cosine \theta$$

where $\gamma$ is the interfacial tension between the organic and aqueous phase, $R_{pore}$ is the effective pore radius, and $\theta$ is the three-phase contact angle between the membrane material and the fluids in contact with it. Typically, membrane pore sizes will be chosen such that the intrusion pressure will be at least several psi, preferably at least 10 psi, in order to provide a comfortable operating pressure window and to ensure stable operation of the membrane in its role as a phase separator and the volumetric flowrates of the aqueous and organic fluids flowing past the membrane differ by a factor from about 2 to about 10.

The feed stream that carries the initial reactants into the extractive membrane reactor module and into contact with the optionally enzyme-activated membrane is aqueous or water-miscible. The flowrate of the feed stream is preferably adjusted so as to obtain the desired degree of enzymatic conversion of a key reactant (e.g., one of the stereoisomers in a racemic feed mixture). The flowrate of the organic stream on the opposite side of the membrane is preferably adjusted to permit one or more of the organic-soluble enzymatic reaction products to be withdrawn at an appropriate concentration.

In an extractive membrane reactor system where a key reactant is water-soluble and it is desirable to remove an inhibitory or unstable organic-soluble reaction product by extracting it into an organic solvent, it may be desirable to flow the organic process stream past the enzyme-activated membrane at a relatively high rate. Operation in this manner facilitates prompt and efficient removal of product from the enzymatic reaction zone, since high organic stream flowrates translate to low product concentrations. In this way, the yield and productivity of the enzymatic reaction are improved. Similar considerations apply to the multiphase dispersion extractive reactor method.

Figure 1:
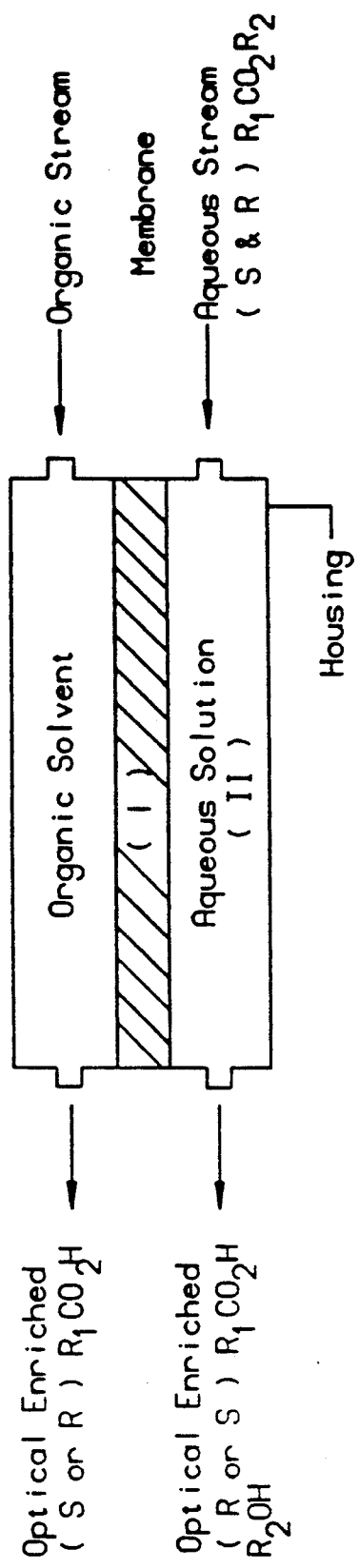
Figure 2:
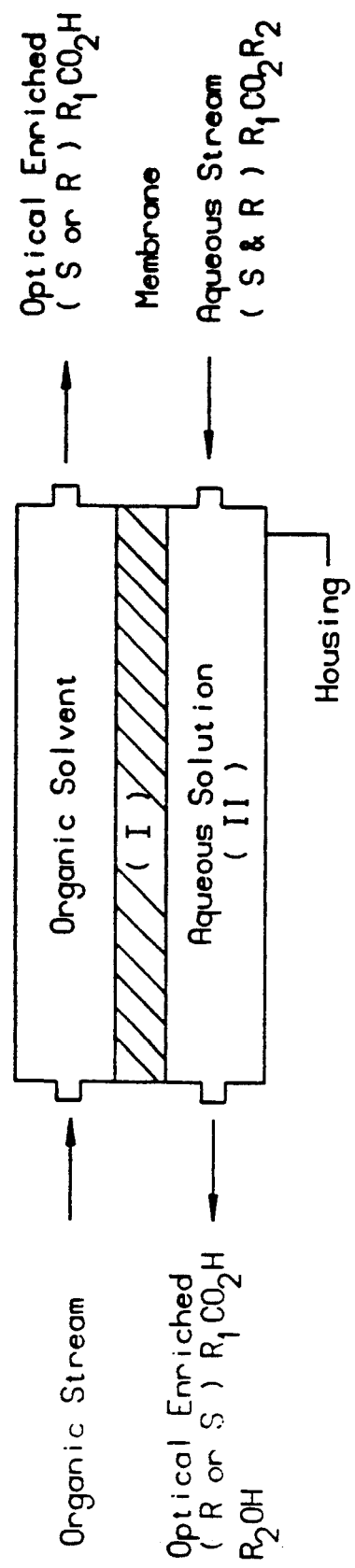

The relationship between the flowrates of the organic and aqueous process streams also exerts an important effect on the stereochemical purity of the products removed from the process. The flows of the aqueous and organic process streams may be either cocurrent (FIG. 1) or countercurrent (FIG. 2), and the extractive reactor process may be operated either batchwise (also, if desired, with recycle of one or both process streams), in a continuous mode, or in a semi-batch fashion. The details of the flow configuration can affect a number of secondary aspects of extractive reactor process performance including product purity, reactant conversion, phase separation and pH control. It is not desired to direct the flow of the organic or aqueous process streams through the enzyme-activated membrane; rather, the convective flow of these immiscible process streams is preferably directed past the external surfaces of the membrane. Reactants are made to enter and products to leave the enzyme-activated membrane by diffusive processes in response to their local concentration gradients and consistent with their aqueous/organic partitioning behavior.

The temperature of the reaction vessel (e.g., continuous stirred-tank reactor or membrane module) and of the aqueous and organic process streams fed to it will be maintained in a range optimal for enzyme activity and stability, as will be the solution pH. Where subsequent processing operations on one or both of the product streams exiting the membrane reactor dictate it (e.g., to effect the chemical reaction of the desirable isomer in a racemic mixture of stereoisomers to permit its recycle to the process or to chemically hydrolyze an enzyme-inactive ester to recover the corresponding chiral acid), the temperature, pH and other properties of the process stream may be adjusted outside of the range required for efficient enzyme operation. In this event, such streams may be returned to their original conditions of pH and temperature prior to being fed back into the membrane reactor itself.

Figure 3:
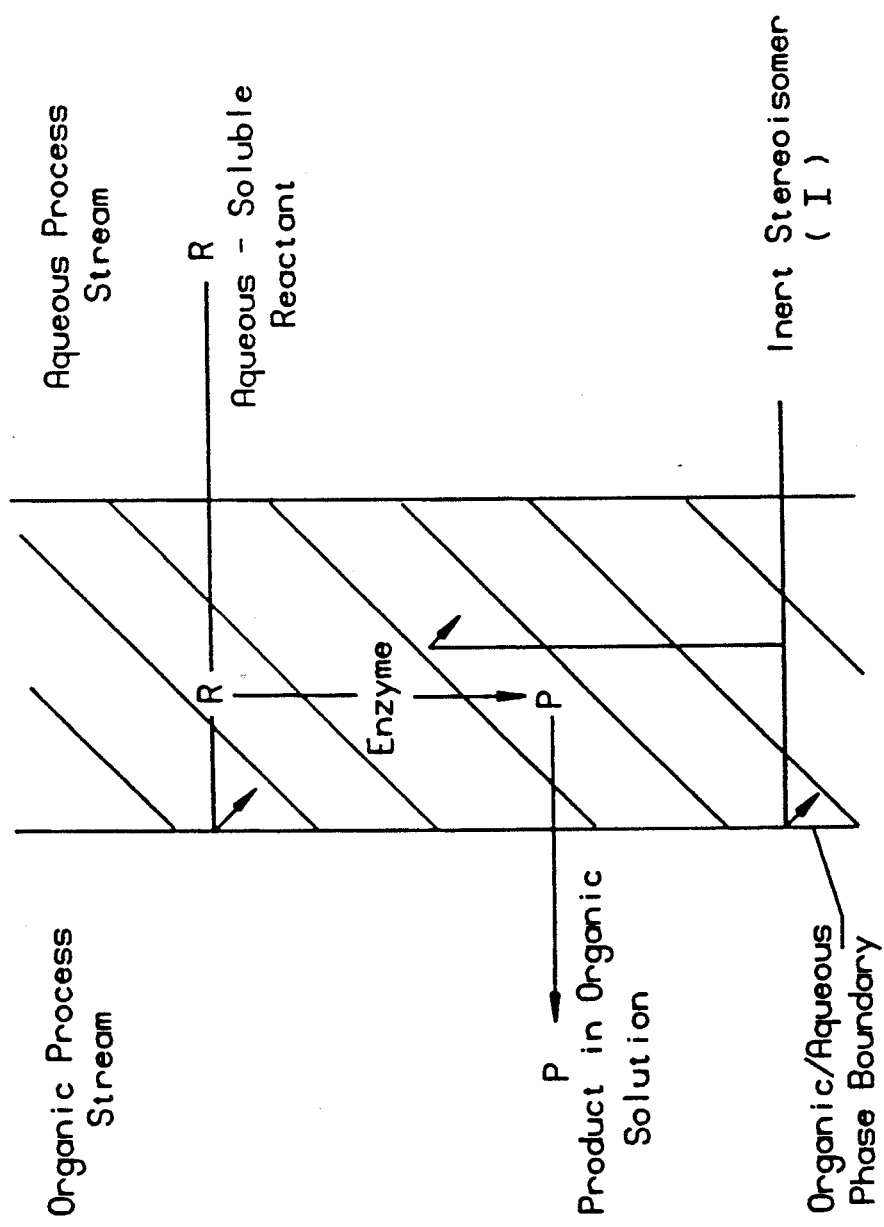
Figure 4:
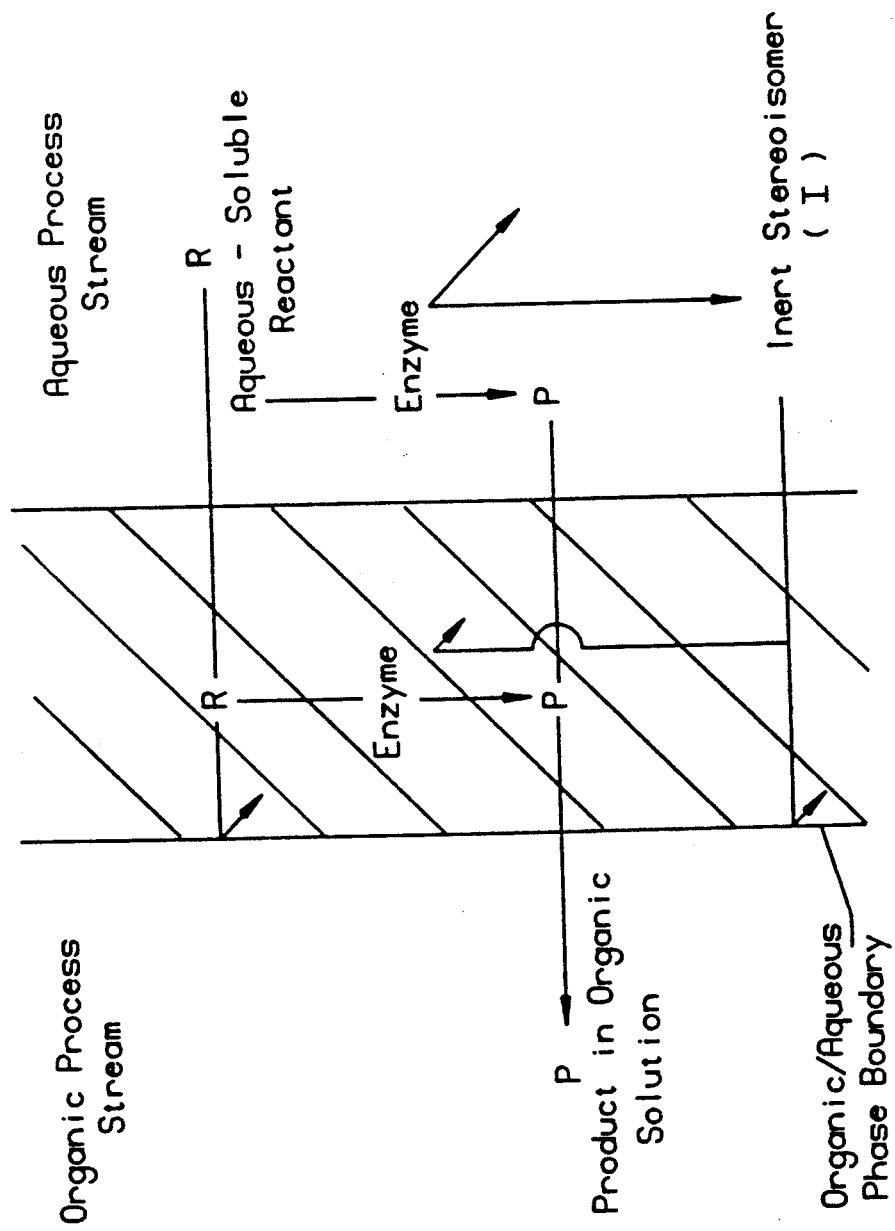
Figure 5:
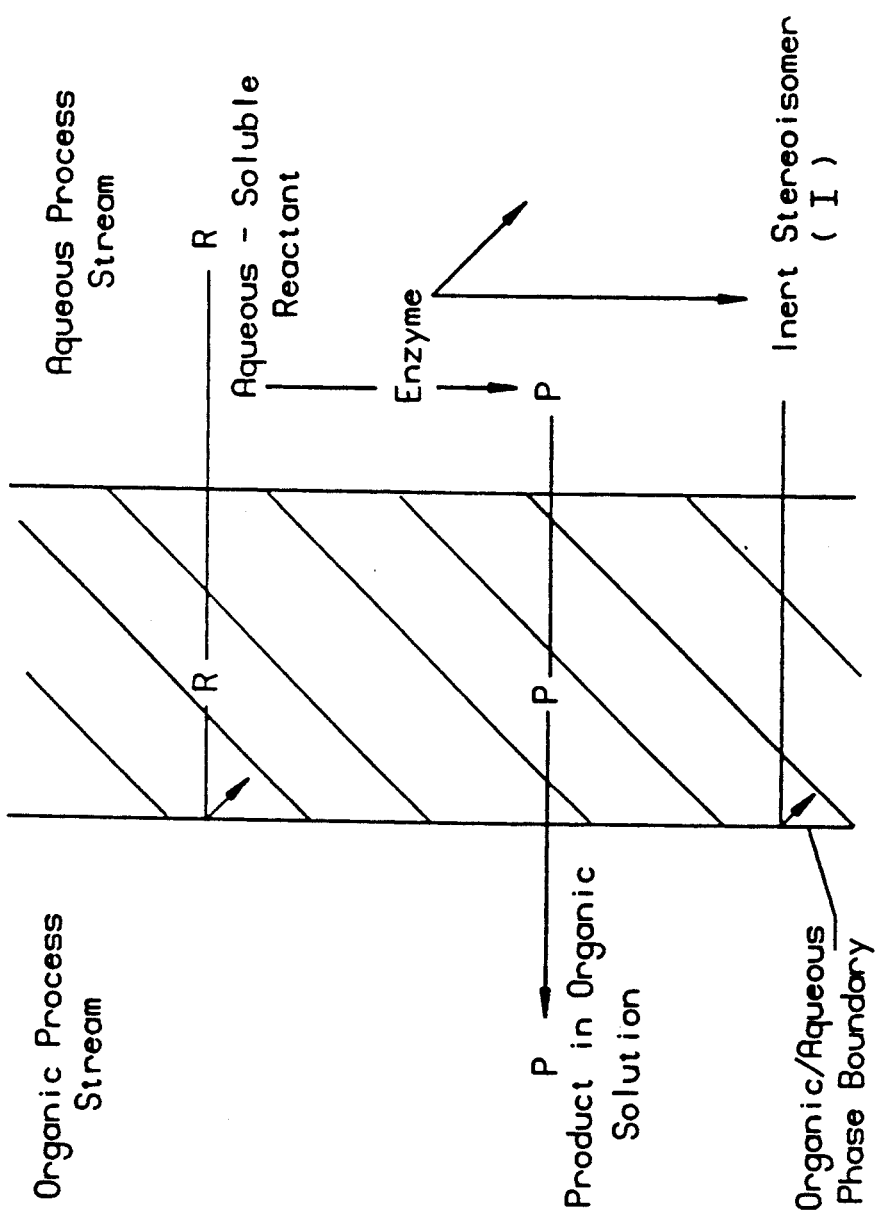
Figure 6:
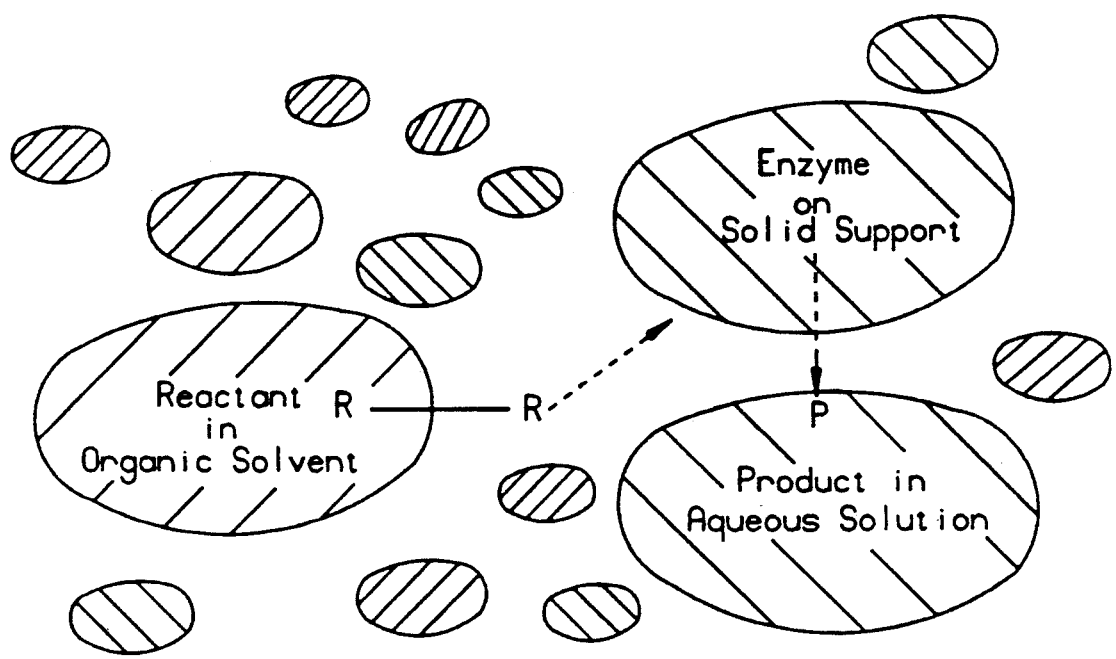
FIG. 6 shows the disposition of the three phases in the conventional, dispersed-phase multiphase bioreactor operation.
Figure 6:
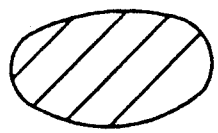
Figure 6:
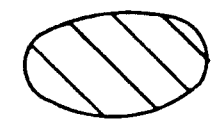

Additional processing steps (e.g., repeated application of the resolution process, recycling of the racemic mixture fluid (FIG. 10) and purification of unconverted reactants and/or products) may improve the efficiency of the resolution process, and the chemical and stereochemical purity of the chiral products produced therein. For instance, where the optically resolved product exits a multiphase dispersion or membrane extractive reactor in an organic solution (e.g., ibuprofen or naproxen), this organic process stream may be pumped to a holding tank and treated with a basic solution in order to remove the acid from the organic solution, and the organic solvent could be recycled (FIG. 12). Alternatively, the product may be separated from the organic fluid and purified by evaporation of the volatile organic solvent and attendant crystallization of the resolved acid product. In addition, the chiral product could be racemized, converted back to the chemical form of the starting racemic stereoisomer mixture, and reintroducing this formed racemic mixture back to the membrane. When an optically purified organic-soluble product exits an extractive reactor in the organic process stream in the form of a neat organic liquid or as a solution in a volatile organic solvent, the product may be further purified by distillation or by solvent evaporation. In the application of this invention to the resolution of racemic mixtures of water-soluble reactants as shown in FIGS. 3-5, the enzyme contained or otherwise immobilized upon or within the membrane and/or in the aqueous process stream is chosen to exhibit maximal stereoselectivity in the bioconversion of one or more but not all of the particular optical isomers present in the feed mixture. The reaction of substantially more water-soluble isomers to at least one substantially more organic-soluble reaction product is catalyzed by the enzyme, and this water-insoluble product is subsequently withdrawn in the organic process stream in a state of relatively high optical purity. At the same time, the mixture of feed isomers is depleted in that particular optical isomer which serves as the better substrate for the stereoselective enzyme, and in this manner the exiting aqueous-phase feed stream may simultaneously be optically purified and enriched in the non-reactive isomer with stereoconfiguration opposite from that of the organic-phase product species.

The net result is that an aqueous-phase mixture of R and S optical isomers is separated into two process streams, one of which (i.e., the organic-phase product stream) contains the converted lipophilic isomer product of the enzymatic reaction present in the organic feed stream, while the original aqueous stream contains the relatively water-soluble reactant possessing the opposite stereochemical configuration. In this manner, a feed stream containing a mixture of both R and S optical isomers is processed such that two "product" streams result, one of which is enriched in material with the R (or S) configuration while the other of which is enriched in material with the S (or R) configuration. Overall yields of the desired enantiomer of the product may be further enhanced by racemization of the material in one of the exiting streams, followed by its recycle to the inlet of the resolution process as shown in FIGS. 11 & 13.

In the practice of the extractive membrane reactor for stereochemical purification of a chiral ester, a protease enzyme would preferably be confined within a membrane and/or in the aqueous phase in contact with it, with the opposite faces of said membrane being contacted by streams of an aqueous solution (typically containing a low concentration of buffer) containing a racemic mixture of water-soluble stereoisomers of a reactant ester and an organic solvent as shown in FIGS. 1-5. Because the organic acid will exhibit some solubility in the organic solution at operating pH, and because the solubility characteristics of the water-soluble ester are precisely the opposite, optically purified product acid can be carried out of the extractive membrane reactor in the organic process stream, while the relatively non-reactive stereoisomer of the racemic ester feed mixture will preferentially remain in the aqueous stream. Product removal is facilitated by operating the reactor with organic solvents that provide optimal partitioning selectivity between reactants and products.

On the one hand, where it is the less enzymatically reactive ester that has the "correct" (i.e., biologically active) stereochemical configuration, it may be withdrawn from the process in the aqueous phase and isolated therefrom; and if it is the acid form of this isomer which is desired, the optically purified ester may be chemically hydrolyzed, without substantially altering the stereochemical purity, to yield the optically purified acid as the desired product. Alternatively, the aqueous phase containing the unreactive stereoisomer can be removed from the membrane, racemizing the stereoisomer, and reintroducing the racemized stereoisomer mixture in the aqueous to the membrane. Meanwhile, the carboxylic acid product in the organic phase, depleted in material with the desired stereochemical configuration and thereby enriched in the undesired material, may optionally be re-esterified before or after being subjected to racemizing conditions prior to recycle to the process. On the other hand, where it is the more enzymatically reactive ester that has the "correct" stereochemical configuration, the desired product will be found in the form of the optically purified acid.

Thus, the above-described extractive membrane reactor process separates an aqueous-phase mixture of R and S esters into two process streams, with the aqueous stream containing the unconverted stereoisomer of the hydrophilic ester present in the original feed stream, and the organic stream containing the relatively organic-soluble acid isomer possessing the opposite stereochemical configuration. In this manner, a feed stream containing a mixture of both R and S esters is processed such that two "product" streams result, one of which is enriched in material with the R configuration while the other of which is enriched in material with the S configuration. If the enzyme is active towards the R form of the ester as shown in FIG. 13, and if the S-isomer is the desired product, then it will be recovered from the exiting aqueous process stream in the form of the S-ester; the S-acid can be recovered after chemical hydrolysis. If it is the R-isomer which is required, then material with this stereochemical configuration may be isolated from the organic process stream.

FIGS. 3-5 illustrate a particular extractive enzyme membrane reactor process for the resolution of racemic esters and acids wherein the chiral center resides on the acid moiety. The above description of the operation of these enzyme membrane reactors and description of the examples which follow, are meant only to suggest the breadth of potential applications of the compounds of this invention in the production of stereochemically pure compounds, and they are by no means limiting as to the scope of the invention or the modes of operation intended for these multiphase and extractive membrane reactor processes.

6.0 EXAMPLES

Examples of the practice of the invention and elements thereof are as follows. As used herein the letter "u" alone or as a prefix is intended to mean "micro."

The term alkyl used herein comprises both straight and branched alkyl moieties.

6.1 SYNTHESIS OF WATER-SOLUBLE AND WATER INSOLUBLE ESTERS

The results of the following syntheses are summarized in Table 2 for example 6.1.1–6.1.21.

EXAMPLE 6.1.1: Method A1 Preparation of the Sodium Salt of 4-Sulfomethyl Ester of 2-(4-Isobutylphenyl)propanoic Acid (Compound 1)

To a beaker containing 125 ml of trifluoroacetic acid were added 2-(4-isobutylphenyl)propanoic acid (103 gm, 0.5 mol) and sodium formaldehyde bisulfite (67 gm. 0.5 mol). This mixture was stirred as trifluoroacetic anhydride (105 gm, 0.5 mol) was added in one portion. The mixture warmed up as the reactants quickly dissolved. After 30 minutes, the hazy solution was filtered through a glass frit, and the filtrates were evaporated under vacuum. The residue was dissolved in water, and a small amount of unreacted 2-(4-isobutylphenyl)-propanoic acid which precipitated was removed by extraction with hexane. The aqueous filtrates were then saturated with sodium chloride causing the desired product to separate as a white solid. This material was isolated by filtration and dried to produce 130 gm of Compound 1 in 81% yield.

TABLE 2

SUMMARY OF COMPOUNDS AND METHODS OF PREPARATION

| | Compound | Method of Preparation | Yield |
|---|---|---|---|
| 1 | Sodium Salt of 4-Sulfomethyl Ester of 2-(4-Isobutylphenyl)propanoic Acid | A1 | 81% |
| | | B1 | 68% |
| 2 | Sodium Salt of 2-Sulfoethyl Ester of 2-(4-Isobutylphenyl)propanoic Acid | A2 | 76% |
| 3 | Potassium Salt of 3-Sulfopropyl Ester of 2-(4-Isobutylphenyl)propanoic Acid | C1 | 82% |
| 4 | Potassium Salt of 4-Sulfobutyl Ester of 2-(4-Isobutylphenyl)propanoic Acid | C2 | 74% |
| 5 | Disodium Salt of the Phosphoric Acid Ester of the 2-Hydroxyethyl Ester of 2-(4-Isobutylphenyl)propanoic Acid | D | 12% |
| 6 | Potassium Salt of the Sulfuric Acid Ester of 3-Hydroxypropyl Ester of 2-(4-Isobutylphenyl)propanoic Acid | E | 42% |
| 7 | Potassium Salt of the 3-Sulfopropyl Ester of 2-(6-Methoxy-2-naphthyl)propanoic Acid | C3 | 25% |
| 8 | Potassium Salt of 2-Sulfoethyl Ester of 2-(6-Methoxy-2-naphthyl)propanoic Acid | B2 | 69% |
| 9 | Sodium Salt of Sulfomethyl Ester of 2-(6-Methoxy-2-naphthyl)propanoic Acid | A3 | 29% |
| 10 | Iodide Salt of 2-(N,N,N-Trimethylammonium)ethyl Ester of 2-(4-Isobutylphenyl)propanoic Acid | F1 | 23% |
| 11 | Methyl Sulfate Salt of 2-(N,N,N-Trimethylammonium)ethyl Ester of 2-(6-Methoxy-2-naphthyl)propanoic Acid | F2 | 66% |
| 12 | Methyl Sulfate Salt of 3-(N,N,N-Trimethylammonium) propyl Ester of 2-(6-Methoxy-2-naphthyl)propanoic Acid | F3 | 80.9% |
| 13 | Potassium Salt of 3-Sulfopropyl Ester of 2-Chloropropanoic Acid | C4 | 40% |
| 14 | Potassium Salt of the Sulfomethyl Ester of D-(−)-S-3-Acetylthio-2-methylpropanoic Acid | B3 | 43% |
| 15 | Potassium Salt of the Sulfomethyl Ester of L-(+)-S-3-Acetylthio-2-methylpropanoic Acid | B4 | 76% |
| 16 | Potassium Salt of the Sulfomethyl Ester of (±)-S-3-Benzoylthio-2-methylpropanoic Acid | B5 | 88% |

TABLE 2-continued

SUMMARY OF COMPOUNDS AND METHODS OF PREPARATION

| | Compound | Method of Preparation | Yield |
|---|---|---|---|
| 17 | Sodium Salt of the Sulfomethyl Ester of 2-(4-Chlorophenoxy) propanoic Acid | B6 | 20% |
| 18 | Methyl Ester of 2-(6-Methoxy-2-naphthyl)propanoic Acid. | B7 | — |
| 19 | 2,2,2-Trifluoroethyl Ester of 2-(4-Isobutylphenyl)propanoic Acid | B8 | 95% |
| 20 | Octyl Ester of 2-Chloropropanoic Acid | G | 95% |

EXAMPLE 6.1.2: Method B1 Preparation of the Sodium Salt of 4-Sulfomethyl Ester of 2-(4-Isobutylphenyl)propanoic Acid (Compound 1)

Ibuprofen (20.6 gm, 0.1 mol) and thionyl chloride (11.9 gm, 0.1 mol) were stirred together with 2 drops of dimethyl formamide. The mixture was warmed at 45° C. until evolution of hydrogen chloride and sulfur dioxide stopped, and then for 1 hour longer. The pale yellow liquid acyl chloride thus prepared was used in the next step without further purification.

Sodium formaldehyde bisulfite (13.4 gm, 0.1 mol) was stirred in 50 ml of pyridine at 0° C. as the acyl chloride was slowly dripped into the mixture. After addition was complete, the reaction mixture was stirred at room temperature for 1 hour. Excess pyridine was removed under vacuum, and the residue was then dissolved in water. After acidification to pH 2, any precipitated ibuprofen was removed by extraction with diethyl ether. The clear aqueous layer was diluted to 300 ml and the sulfomethyl ester was precipitated by addition of 75 gm of sodium chloride. The solid ester was isolated by filtration and dried to give 22 gm of ester (68% yield) as a pure white solid.

Before being subjected to enzymatic hydrolysis, this ester was further purified by dissolving it in water and reprecipitating it by the addition of sodium chloride. This additional purification by recrystallization was found to improve the ultimate enantiomeric excess of resolved ibuprofen made from this material.

EXAMPLE 6.1.3: Method A2 Preparation of the Sodium Salt of 2-Sulfoethyl Ester of 2-(4-Isobutylphenyl)propanoic Acid (Compound 2)

The procedure of Method A1 was followed with the following exceptions. An equivalent amount of the sodium salt of isethionic acid was used in place of sodium formaldehyde bisulfite. The aqueous filtrates were treated with a slight excess of barium chloride dissolved in water to precipitate the barium salt of the desired product. The barium salt was converted to the soluble sodium salt by warming in a solution containing 1 equivalent of sodium sulfate. The precipitate of barium sulfate was removed by centrifugation to provide a solution of the sodium salt of Compound 2 in 76% yield.

EXAMPLE 6.1.4: Method C1 Preparation of the Potassium Salt of 3-Sulfopropyl Ester of 2-(4-Isobutylphenyl)propanoic Acid (Compound 3)

To a solution of 2-(4-isobutylphenyl)propanoic acid (30.9 gm, 0.15 mol) in 300 ml of methylisobutylketone was added powdered potassium hydroxide (9.9 gm of 85% KOH, 0.15 mol). This mixture was stirred until all the potassium hydroxide was dissolved, after which, 1,3-propane sultone (18.3 gm, 0.15 mol) was added all at once. A slightly exothermic reaction began which was allowed to proceed without cooling. After one hour, the resulting solid mass was broken up and the solid isolated by filtration. This solid was dissolved in 300 ml of boiling methanol. The solution was filtered to remove a small amount of solid, and the filtrates were treated with warm 2-propanol to the cloud point. Upon cooling, compound 3 crystallized as white plates. The product was isolated by filtration, washed once with cold 50% methanol in 2-propanol, and dried. The yield of compound 3 was 45 gm or 82%.

EXAMPLE 6.1.5: Method C2 Preparation of the Potassium Salt of 4-Sulfobutyl Ester of 2-(4-Isobutylphenyl)propanoic Acid (Compound 4)

The procedure of Method C1 was followed, with the exception that the reaction was run in boiling 2-propanol for 2 hours and the 1,3-propane sultone was replaced with 1,4-butane sultone. The yield of Compound 4 was 74%.

EXAMPLE 6.1.6: Method D Preparation of the Disodium Salt of the Phosphoric Acid Ester of the 2-Hydroxyethyl Ester of 2-(4-Isobutylphenyl)propanoic Acid (Compound 5)

Polyphosphoric acid (80 gm, 1 equivalent) and 2-hydroxyethyl ester of 2-(4-isobutylphenyl)propionate (25 gm, 0.1 equivalent) were mixed together and stirred at 100° C. for ten minutes. After cooling, the mixture was dissolved in 1 l of water, and the pH was adjusted to 6 by addition of aqueous sodium hydroxide. Sodium chloride was added to precipitate the phosphate as a sticky solid. This material was isolated by centrifugation. A second dissolution/precipitation gave the 4.6 gm of the product as a white solid after trituration in acetone. The overall yield of Compound 5 was 12%.

EXAMPLE 6.1.7: Method E Preparation of the Potassium Salt of the Sulfuric Acid Ester of 3-Hydroxypropyl Ester of 2-(4-Isobutylphenyl)propanoic Acid (Compound 6)

The 3-hydroxypropyl ester of 2-(4-isobutylphenyl)-propanoic acid (13.3 gm, .05 mol) was dissolved in 100 ml of methylene chloride containing pyridine (7.9 gm, 0.1 mol). After cooling to 0° C., chlorosulfonic acid (5.83 gm, .05 mol) dissolved in 50 ml of methylene chloride was dripped in, with stirring. After 1 hour at 0° C., the methylene chloride was stripped under vacuum. The resulting oil was stirred in tetrahydrofuran to precipitate pyridine hydrochloride, which was removed by filtration The tetrahydrofuran was evaporated under vacuum and the residue was dissolved in methanol. The pH was adjusted to 7 by addition of potassium hydroxide dissolved in methanol. This solution was filtered free from a small amount of solid and was again evaporated under vacuum. The residue was dissolved in water and the product was salted out by the addition of sodium chloride. The solid was isolated by centrifugation. A second salting out from aqueous solution gave 8 gm of a waxy solid, corresponding to a yield of 42%.

EXAMPLE 6.1.8: Method C3 Preparation of the Potassium Salt of the 3-Sulfopropyl Ester of 2-(6-Methoxy-2-naphthyl)propanoic Acid (Compound 7)

The procedure of Method C1 was followed with the following exceptions. The solvent was changed to 20% methanol and 80% methylisobutylketone, and the reaction was allowed to proceed overnight. The product was isolated by dissolving the crude solid in water, extracting any unreacted naproxen from the mixture with ethylacetate, and then salting the product from solution by addition of sodium chloride. The yield of Compound 7 was 25%.

EXAMPLE 6.1.9: Method B2 Preparation of the Potassium Salt of 2-Sulfoethyl Ester of 2-(6-Methoxy-2-naphthyl) propanoic Acid (Compound 8)

A slurry of 2-(6-methoxy-2-naphthyl)propanoic acid (239 gm, 0.1 mol) in 250 ml of methylene chloride was treated with thionyl chloride (11.9 gm, 0.1 mol) and 100 ul of dimethyl formamide. This mixture was refluxed for 1 hour and then left at room temperature overnight to provide a pale yellow solution. The methylene chloride was evaporated under vacuum and the residual acid chloride was dissolved in 50 ml of tetrahydrofuran. The solution was dripped into a mixture of the sodium salt of isethionic acid in 300 ml of pyridine at 0° C., with stirring. After stirring at 0° C. for 1 hour, the pyridine was removed under vacuum and the residue was dissolved in 300 ml of water. The pH was adjusted to 1-2 using concentrated HCl, and unreacted 2-(6-methoxy-2-naphthyl)propanoic acid was removed by extraction with ethyl acetate. The aqueous extracts were treated with sodium chloride to precipitate the product. The 25 gm of product so recovered corresponds to a yield of 69%.

EXAMPLE 6.1.10: Method A3 Preparation of the Sodium Salt of Sulfomethyl Ester of 2-(6-Methoxy-2-naphthyl)propanoic Acid (Compound 9)

The procedure of Method A1 was followed, except that unreacted naproxen was removed by extraction with methylene chloride. The yield of Compound 9 was 29%.

EXAMPLE 6.1.11: Method F1 Preparation of the Iodide Salt of 2-(N,N,N-Trimethylammonium)ethyl Ester of 2-(4-Isobutylphenyl)propanoic Acid (Compound 10)

Ibuprofen acid (103 gm, 0.5 mol) was stirred in 40 ml of $SOCl_2$ (1.05 mol.) with slight warming. Upon dissolution of the solid material, the reaction mixture became clear, and gas was evolved. Warming was continued for 30 minutes, then the heat source was removed and the reaction mixture was allowed to stir for 16 hours at ambient temperature. Excess $SOCl_2$ was removed under reduced pressure to give a quantitative yield of the ibuprofen acyl chloride (124.5 g, 105 ml).

Next, the above acyl chloride (57.5 ml, 0.25 mol) was added slowly dropwise to a cooled, vigorously stirred solution of 2.0 equivalents (0.5 mol) of 2-(N,N-dimethylamino)ethanol in 200 ml of tetrahydrofuran. Addition was complete in approximately one hour, after which time the reaction was stirred an additional hour. The reaction mixture was poured into 500 ml water, and extracted 3 times with 250 ml diethyl ether. The combined organic layers were washed with 1 N NaOH, (3 times, 100 ml), water (300 ml), saturated NaCl solution (300 ml), and then dried over MgSO$_4$. Evaporation of the ether under reduced pressure left a nearly quantitative yield (70.0 gm) of a clear, slightly yellow oil.

Finally, iodomethane (12.5 ml, 0.2 mol), diluted with 20 ml tetrahydrofuran, was added slowly dropwise to a solution of the above ester of ibuprofen (56 gm, 0.2 mol) in 300 ml tetrahydrofuran. The addition was complete in 30 minutes, and the reaction was allowed to stir an under reduced pressure left a yellow gum (84 gm, approximately 100% yield). This was recrystallized from water at 4 ° C. to leave the desired ibuprofen ester (Compound 10) as a pale yellow, slightly hygroscopic powder. This product was collected by centrifugation, and dried under vacuum to produce 19.5 gm of product at an overall yield of 23% from the ibuprofen acid starting material.

EXAMPLE 6.1.12: Method F2 Preparation of the Methyl Sulfate Salt of 2-(N,N,N-Trimethylammonium)ethyl Ester of 2-(6-Methoxy-2-naphthyl)propanoic Acid (Compound 11)

23 gm (0.1 mol) of racemic naproxen was stirred in a solution of 200 ml dichloromethane, 7.3 ml (0.1 mol) thionyl chloride and 5 drops dimethylformamide. The mixture was brought to reflux for 1 hour, during which time the naproxen acid dissolved, and HCl and SO$_2$ were generated. The heat was then removed and the reaction mixture allowed to stir overnight at ambient temperature. The dichloromethane was removed on a Rotovap to leave a viscous yellow oil. This oil was dissolved in 50 ml of tetrahydrofuran, and added dropwise to a solution of 2-(N,N-dimethylamino)ethanol (2.0 equiv., 18.0 ml) in 100 ml tetrahydrofuran, the reaction flask being cooled in an ice bath. Addition was complete in 20 minutes, and the reaction was allowed to stir an additional hour at ambient temperature. The tetrahydrofuran was removed on the Rotovap, and the viscous residue poured into 1N NaOH and extracted with diethyl ether (3×200 ml). The combined organic layers were washed with water (2×300 ml), and dried of K$_2$CO$_3$. Evaporation left the N,N-dimethylethanolamine ester as a pale yellow oil (20.0 gm recovered, 66% yield).

All of the above ester was dissolved in 100 ml of 2-propanol to which were added 6.2 ml of dimethyl sulfate. The reaction mixture was brought to reflux for 15 minutes, cooled to ambient temperature, and the alcohol removed on the Rotovap to leave the quaternary ammonium salt as a viscous pale yellow oil, which could be chilled to a glass at −80° C.

EXAMPLE 6.1.13: Method F3 Preparation of the Methyl Sulfate Salt of 3-(N,N,N-Trimethylammonium)propyl Ester of 2-(6-Methoxy-2-naphthyl)propanoic Acid (Compound 12)

23 gm (0.1 mol) of racemic naproxen was stirred in 250 ml of methylene chloride and treated with 11.9 gm (7.3 ml, 0.1 mol) of thionyl chloride and a few drops of dimethylformamide. The mixture was brought to reflux for 2 hours to provide a pale yellow solution. This was cooled to room temperature overnight and stripped to give an oil which quickly solidified.

The acid chloride from above was dissolved in 50 ml of tetrahydrofuran and dripped into a solution of 3-(N,N-dimethylamino)propanol (20.6 gm, 0.2 mol) dissolved in 200 ml tetrahydrofuran at 0 ° C., with stirring. After the addition, the resulting slurry was stirred at room temperature for 1 hour and them stripped. The residue was shaken with 500 ml of saturated NaHCO$_3$ solution, and the oily precipitant taken into ethyl acetate was stripped to give 27 gm (85.6%) yield of the 3-(N,N-dimethylamino)propyl ester of naproxen as a pale yellow oil.

12.6 gm (0.04 mol) of crude ester from above was dissolved in 50 ml 2-propanol and treated with dimethyl sulfate (5.04 gm, 3.78 ml, 0.04 mol). This solution was brought to reflux and held there until an aliquot, when added to H$_2$O, gave a clear solution after approximately 15 minutes. While still hot, 50 ml ethyl acetate was added and this solution was cooled on ice causing the desired quaternary ammonium ester to crystallize as a white powder. This was isolated by filtration and was washed with ethyl acetate and then pentane to yield 16.7 gm (80.9%) of compound 12.

EXAMPLE 6.1.14: Method C4 Preparation of the Potassium Salt of 3-Sulfopropyl Ester of 2-Chloropropanoic Acid (Compound 13)

The procedure of C1 was followed with the following exception. To a solution of 2-chloropropanoic acid (10.8 gm, 0.10 mol) in 200 ml of methylisobutylketone and 50 ml methanol was added powdered potassium hydroxide (6.6 gm of 85% KOH, 0.10 mol). This mixture was stirred until all the potassium hydroxide was dissolved, after which, 1,3-propane sultone (12.2 gm, 0.10 mol) was added all at once. A slightly exothermic reaction began which was allowed to proceed without cooling. After allowing the reaction to proceed overnight, the resulting solid mass was broken up and the solid isolated by filtration. This solid was dissolved in 75 ml of boiling methanol. The solution was filtered to remove a small amount of solid, and the filtrates were treated with warm 2-propanol to the cloud point. Upon cooling, the sodium salt of the sulfopropyl ester of 2-chloropropanoic acid crystallized as a white powder. The product was isolated by filtration, washed once with cold 2-propanol, washed once again with diethyl ether, and then dried. The yield of product was 10.8 gm or 40%.

EXAMPLE 6.1.15: Method B3 Preparation of the Potassium Salt of the Sulfomethyl Ester of D-(-)-S-3-Acetylthio-2-methylpropanoic Acid (Compound 14)

The procedure of B1 was followed with the following exceptions. D-(−)-S--3-acetylthio-2-methylpropanoic acid (1.62 gm, 0.01 mol) and thionyl chloride (1.19 gm, 0.01 mol) were stirred together with 1 drop of dimethyl formamide. The mixture was maintained at room temperature until evolution of hydrogen chloride and sulfur dioxide stopped, and then for 1 hour longer. The pale yellow liquid acyl chloride thus prepared was used in the next step without further purification.

Sodium formaldehyde bisulfite (1.47 gm, 0.011 mol) was stirred in 5 ml of pyridine at 0° C. as the acyl chloride was slowly dripped into the mixture. After addition was complete, the reaction mixture was stirred at room temperature for 2 hours, during which time the mixture solidified. Diethyl ether was added to precipitate the product, which was collected by filtration and dried. The crude material was recrystallized from hot saturated KCl solution. The yield of product was 1.2 gm or 43%.

EXAMPLE 6.1.16: Method B4 Preparation of the Potassium Salt of the Sulfomethyl Ester of L-(+)-S-3-Acetylthio-2-methylpropanoic Acid (Compound 15)

The procedure of B3 was followed with the following exceptions. L-(+)-S-3-acetylthio-2-methylpropanoic acid was used. The yield of product was 2.1 gm or 76%.

EXAMPLE 6.1.17: Method B5 Preparation of the Potassium Salt of the Sulfomethyl Ester of (+)-S-3-Benzoylthio-2-methylpropanoic Acid (Compound 16)

The procedure of B1 was followed with the following exceptions. Racemic S-3-benzoylthio-2-methylpropanoic acid (11.2 gm, 0.05 mol) and thionyl chloride (5.95 gm, 0.05 mol) were stirred together with 1 drop of dimethylformamide. The mixture was maintained at room temperature until evolution of hydrogen chloride and sulfur dioxide stopped, and then heated to 50° C. for 15 minutes. The pale yellow liquid acyl chloride thus prepared was used in the next step without further purification.

Sodium formaldehyde bisulfite (7.4 gm, 0.055 mol) was stirred in 25 ml of pyridine at 0° C. as the acyl chloride was slowly dripped into the mixture. After addition was complete, the reaction mixture was stirred at room temperature for 1 hour. Excess pyridine was removed under vacuum, and the residue was then triturated with diethyl ether. The remaining solid was dissolved in 25 ml boiling water and treated with 50 ml of boiling saturated KCl solution. This mixture was cooled, causing the material to crystallize as a white solid. The product was isolated by filtration, washed two times with 1 volume of water and 2 volumes of saturated KCl solution, and then dried to yield 15 gm or 88% of product.

EXAMPLE 6.1.18: Method B6 Preparation of the Sodium Salt of the Sulfomethyl Ester of 2-(4-Chlorophenoxy)propanoic Acid (Compound 17)

The method of B1 was followed with the following modifications. 30.2 g (0.15 mol) of racemic 2-(4-chlorophenoxy)propanoic acid were dissolved in 50 ml of thionyl chloride and 0.5 ml of dimethyl formamide. The resultant mixture was refluxed for two hours, and the excess thionyl chloride removed on a Rotovap under reduced pressure to leave a pale yellow oil (approximately 36 g, containing some dimethyl formamide This product was added dropwise to a vigorously stirred solution of 40.2 g (0.3 mol, 2.0 equiv.) sodium formaldehyde bisulfite adduct in 75 ml of pyridine. During addition, the reaction mixture was cooled in an ice bath. After 20 minutes, addition was complete, and the ice bath was removed. The reaction mixture was stirred at room temperature for one hour, and the excess pyridine removed on a Rotovap under reduced pressure. The remaining residue was taken up in 300 ml of boiling MeOH, filtered, and allowed to crystallize. The solid crystalline material was collected by filtration, washed with diethyl ether to leave 9.2 g of an off-white crystalline material (20% yield).

EXAMPLE 6.1.19: Method B7 Preparation of Methyl Ester of 2-(6-Methoxy-2-naphthyl)propanoic Acid (Compound 18)

The procedure of Method B1 was followed with the following exceptions. Methanol was used in place of the sodium salt of isethionic acid. Following the reaction and removal of the pyridine the residue was dissolved in 300 ml of chloroform, which was washed with 100 ml of a saturated solution of NaHCO$_3$, and finally dried over MgSO$_4$. The organic phase was then evaporated.

EXAMPLE 6.1.20: Method B8 Preparation of 2,2,2-Trifluoroethyl Ester of 2-(4-Isobutylphenyl)propanoic Acid (Compound 19)

The general method B1 was followed, with the following modifications. 258 gm (1.25 mol) of racemic ibuprofen were stirred in 100 ml of thionyl chloride (1.1 equivalents) with slight warming. When the temperature of the mixture reached 45° C., the solid ibuprofen dissolved, gas evolution became obvious, and the heat source was removed. No dimethylformamide was used in this reaction. The reaction mixture was allowed to stir for 16 hours at ambient temperature, after which time 100 ml of benzene were added to the reaction mixture, and the benzene and excess thionyl chloride were removed under reduced pressure on a Rotovap. The resulting crude acid chloride of ibuprofen, a pale yellow liquid, was then added dropwise to a solution of 127 ml 2,2,2-trifluoroethanol (1.4 equivalents) in 160 ml pyridine, this solution being cooled in an ice bath. Addition of the crude acid chloride of ibuprofen was complete in two hours, after which time the ice bath was removed, and the reaction mixture stirred an additional hour. 1 l of 2N HCl was then added to the reaction mixture, and the resulting mixture extracted 4 times with 200 ml of chloroform. The combined organic layers were backwashed 3 times with water (200 ml), once with saturated NaCl solution solution (200 ml), and dried over MgSO$_4$. Evaporation of the chloroform under reduced pressure left 341 gm of the 2,2,2-trifluoroethyl ester of ibuprofen, Compound 19, as a pale yellow liquid, this being a 95% overall yield.

EXAMPLE 6.1.21: Method G Preparation of Octyl Ester of 2-Chloropropanoic Acid (Compound 20)

Racemic 2-chloropropionate octyl ester was prepared by reacting 130 gm (1.0 mol) of n-octanol with 127 gm (1.0 mol) of 2-chloropropionyl chloride in 240 ml of pyridine and 50 ml of tetrahydrofuran. The reaction was carried out for 24 hours after which the solution was washed with 100 ml of 1N HCl and 100 ml of distilled water. 500 ml of ether was added, then washed with 3×500 ml of saturated solution of NaHCO$_3$ and 500 ml of saturated solution of NaCl. The organic phase was finally dried over MgSO$_4$. The total weight of 2-chloropropionate octyl ester obtained was 248 gm.

6.2 SPECIFICITY AND ACTIVITY OF ENZYMATIC RESOLUTION REACTIONS OF RACEMIC MIXTURES OF WATER-SOLUBLE AND WATER-INSOLUBLE ESTERS

The enzymes used in Examples 6.2.1.1–6.2.1.17, 6.2.1.20–6.2.1.21, 6.2.1.23–6.2.1.28, 6.2.2.7, and 6.2.3.1–6.2.3.5 that follow were all proteases commercially available from Sigma Chemical Co., St. Louis, Mo. These proteases are listed in each example using the Sigma numbering system, which is summarized below:

Protease VIII: "Subtilopeptidase A", product P-5380 (also known as subtilisin Carlsberg)
Protease XIV: from *Streptomyces griseus*, product P-5147
Protease XVI: from *Bacillus subtilis*, product P-8775
Protease XXIII: from *Aspergillus oryzae*, product P-4032
Protease XXVII: "Nagarse", product P-4789
Protease XXIV: bacterial protease, product P-8038

An additional protease enzyme, which was designated Prozyme 6, was obtained from the Amano Enzyme Corporation and used in Examples 6.2.1.18–6.2.19, 6.2.1.22, 6.2.1.29–6.2.1.30 and 6.2.2.1–6.2.2.4 described below. A pig liver esterase was used in EXAMPLE 6.21.11; this enzyme, obtained from Sigma Chemical Company, was designated as their product E-3128. For examples 6.2.2.5–6.2.2.6, Candida lipase obtained from Genzyme Corporation was used. Finally, Candida lipase, product L-1754, obtained from Sigma Chemical Co. was used in example 6.2.2.7.

A summary of the several enzymes employed in resolving various water-soluble and water-insoluble esters is given in Table 3. For purposes of clarity, these enzymes have also been provided with letter designations A through J. The chemical formulas of the various substrates (Compounds 1 through 20) cited in the following examples are summarized in Table 2, along with their synthetic procedures (Methods A1 through G described above).

In addition, aspects of the operation of the extractive membrane reactor process of the present invention—wherein water-soluble ester derivatives of such chiral carboxylic acids as naproxen, ibuprofen and 2-chloropropanoic acid are supplied to the enzyme reactor as components in an aqueous feed stream—may be better understood with reference to certain alternative resolution schemes as described in co-pending application Ser. No. 033,962. In particular, Examples 6.2.2.5–6.2.2.7 which follow show how water-insoluble simple ester derivatives of naproxen, ibuprofen and 2-chloropropanoic acid can be resolved in multiphase enzyme membrane reactors. In contrast to the process of the present invention dealing with water-soluble esters fed to extractive reactors in aqueous feed solutions, the following three examples show, for purposes of comparison, how water-insoluble esters may be fed to multiphase reactor in organic feed solutions.

TABLE 3

SUMMARY OF RESOLUTION EXPERIMENTS

| Example No. | Compound or Substrate | Preparative Method | Enzyme |
|---|---|---|---|
| 6.2.1.1 | 1 | A1 | Sigma XXIII (A) |
| 6.2.1.2 | 2 | A2 | Sigma XXIII (A) |
| 6.2.1.3 | 3 | C1 | Sigma XXIII (A) |
| 6.2.1.4 | 4 | C2 | Sigma XXIII (A) |
| 6.2.1.5 | 1 | A1 | Sigma VIII (B) |
| 6.2.1.6 | 1 | A1 | Sigma XVI (C) |
| 6.2.1.7 | 1 | A1 | Sigma XXVII (D) |
| 6.2.1.8 | 3 | C1 | Sigma XXIII (A) |
| 6.2.1.9 | 3 | C1 | Sigma VIII (B) |
| 6.2.1.10 | 3 | C1 | Sigma XXVII (D) |
| 6.2.1.11 | 3 | C1 | Sigma PLE (E) |
| 6.2.1.12 | 2 | A2 | Sigma XXIII (A) |
| 6.2.1.13 | 2 | A2 | Sigma VIII (B) |
| 6.2.1.14 | 4 | C2 | Sigma VIII (B) |
| 6.2.1.15 | 4 | C2 | Sigma XVI (C) |
| 6.2.1.16 | 5 | D | Sigma XVI (C) |
| 6.2.1.17 | 10 | F1 | Sigma XXIII (A) |
| 6.2.1.18 | 11 | F2 | Amano Prozyme 6 (F) |
| 6.2.1.19 | 12 | F3 | Amano Prozyme 6 (F) |
| 6.2.1.20 | 7 | C3 | Sigma XXIII (A) |
| 6.2.1.21 | 3 | C1 | Sigma XXIII (A) |
| 6.2.1.22 | 1 | A1 | Amano Prozyme 6 (F) |
| 6.2.1.23 | 8 | B2 | Sigma XXIII (A) |
| 6.2.1.24 | 6 | E | Sigma XXIII (A) |
| 6.2.1.25 | 9 | A3 | Sigma XXIII (A) |
| 6.2.1.26 | 13 | C4 | Sigma VIII (B) |
| 6.2.1.27 | 16 | B5 | Sigma VIII (B) |
| 6.2.1.28 | 16 | B5 | Sigma XXIII (A) |
| 6.2.1.29 | 17 | B6 | Amano Prozyme 6 (F) |
| 6.2.1.30 | 1 | B1 | Amano Prozyme 6 (F) |
| 6.2.2.1 | 1 | B1 | Amano Prozyme 6 (F) |
| 6.2.2.2 | 1 | A1 | Amano Prozyme 6 (F) |
| 6.2.2.3 | 1 | B1 | Amano Prozyme 6 (F) |
| 6.2.2.4 | 1 | B1 | Amano Prozyme 6 (F) |
| 6.2.2.5 | 18 | B7 | Genzyme Lipase (G) |
| 6.2.2.6 | 19 | B8 | Genzyme Lipase (G) |
| 6.2.2.7 | 20 | G | Sigma Lipase (H) |
| 6.2.3.1 | 14, 15 | B3, B4 | Sigma VIII (B) |
| 6.2.3.2 | 14, 15 | B3, B4 | Sigma Protease XIV (I) |
| 6.2.3.3 | 14, 15 | B3, B4 | Sigma XXIII (A) |
| 6.2.3.4 | 14, 15 | B3, B4 | Sigma Protease XXIV (J) |
| 6.2.3.5 | 14, 15 | B3, B4 | Sigma XXVII (D) |

6.2.1 Enzymatic Resolutions by Homogeneous Aqueous Reactions

EXAMPLE 6.2.1.1: Homogeneous Aqueous Resolution of Sodium Salt of 4-Sulfomethyl Ester of 2-(4-Isobutylphenyl)propanoic Acid Using 100 mg of Enzyme A at pH 7.0

The following procedure was followed in Examples 6.2.1.1–6.2.1.7, which demonstrate resolution of water-soluble ibuprofen derivatives using the substrate/ester combinations shown in Table 4. This set of Examples demonstrates the utility of ibuprofen resolution using the homologous series of water-soluble sulfoalkyl (or #alkylsulfonate) esters—namely, the sulfomethyl (one carbon), sulfoethyl (two carbons), sulfopropyl (three carbon atoms), and sulfobutyl; (four carbon) ester derivatives of ibuprofen.

10.0 millimole (mmol) of ibuprofen substrate ester 1 (the methyl sulfonate derivative) was dissolved in 100 ml of 0.2 M phosphate buffer of the appropriate cation (sodium or potassium, to be the same as the substrate counterion) at pH 7.0. 100 mg of enzyme A, as the commercial preparation, was added directly to this solution, and the reaction mixture was capped and then shaken briefly until all the enzyme preparation had dispersed or dissolved. The reaction mixture was then allowed to stand at ambient temperature (20°–22° C.) for 20 hours. The reaction mixture was then diluted with 1 volume of water and 1 volume of saturated NaCl solution, acidified to a pH of 1–2 by the careful addition of concentrated HCl, and then immediately extracted twice with one volume of methyl-t-butyl ether or diethyl ether.

TABLE 4

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.1 | (A) | 1 | 780 | 37.9 | −57.3° | >99 | R |
| 6.2.1.1 | (A) | 2 | 460 | 22.3 | −53.2° | 93.3 | R |
| 6.2.1.3 | (A) | 3 | 1030 | 50.0 | −48.0° | 84.2 | R |
| 6.2.1.4 | (A) | 4 | 890 | 43.2 | −55.5° | 97.4 | R |
| 6.2.1.5 | (B) | 1 | 600 | 29.1 | −25.4° | 44.6 | R |
| 6.2.1.6 | (C) | 1 | 560 | 27.2 | −40.3 | 70.7 | R |
| 6.2.1.7 | (D) | 1 | 700 | 34.0 | −21.5° | 37.7 | R |

The combined organic layers were backwashed twice with one volume of water, once with one volume of saturated NaCl solution, and then dried over MgSO₄.

Evaporation of the ether under reduced pressure left the resolved ibuprofen acid product; no other purification was performed. The example of the result of resolving the racemic sulfoalkyl ibuprofen ester of 1 with protease enzyme A is summarized in Table 4. The optical rotation was measured in EtOH at a concentration c = 1.0 for the ibuprofen acid product.

EXAMPLE 6.2.1.2: Homogeneous Aqueous Resolution of Sodium Salt of 2-Sulfoethyl Ester of 2-(4-Isobutylphenyl)propanoic Acid Using 100 mg of Enzyme A at pH 7.0

10.0 millimole (mmol) of ibuprofen substrate ester 2 (the ethyl sulfonate derivative) was dissolved in 100 ml of 0.2 M phosphate buffer of the appropriate cation (sodium or potassium, to be the same as the substrate counterion) at pH 7.0. 100 mg of enzyme A, as the commercial preparation, was added directly to this solution, and the reaction mixture was capped and then shaken briefly until all the enzyme preparation had dispersed or dissolved. The reaction mixture was then allowed to stand at ambient temperature (20°-22 ° C.) for 20 hours. The reaction mixture was then diluted with 1 volume of water and 1 volume of saturated NaCl solution, acidified to a pH of 1-2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over MgSO₄.

Evaporation of the ether under reduced pressure left the resolved ibuprofen acid product; no other purification was performed. The example of the result of resolving the racemic sulfoalkyl ibuprofen ester of 2 with protease enzyme A is are summarized in Table 4. The optical rotation was measured in EtOH at a concentration c = 1.0 for the ibuprofen acid product.

EXAMPLE 6.2.1.3: Homogeneous Aqueous Resolution of Potassium Salt of 3-Sulfopropyl Ester of 2-(4-Isobutyphenyl)propanoic Acid Using 100 mg of Enzyme A at pH 7.0

10.0 millimole (mmol) of ibuprofen substrate ester 3 (the propyl sulfonate derivative) was dissolved in 100 ml of 0.2 M phosphate buffer of the appropriate cation (sodium or potassium, to be the same as the substrate counterion) at pH 7.0. 100 mg of enzyme A, as the commercial preparation, was added directly to this solution, and the reaction mixture was capped and then shaken briefly until all the enzyme preparation had dispersed or dissolved. The reaction mixture was then allowed to stand at ambient temperature (20°-22° C.) for 20 hours. The reaction mixture was then diluted with 1 volume of water and 1 volume of saturated NaCl solution, acidified to a pH of 1-2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over MgSO₄.

Evaporation of the ether under reduced pressure left the resolved ibuprofen acid product; no other purification was performed. The example of the result of resolving the racemic sulfoalkyl ibuprofen ester of 3 with protease enzyme A is summarized in Table 4. The optical rotation was measured in EtOH at a concentration c = 1.0 for the ibuprofen acid product.

EXAMPLE 6.2.1.4: Homogeneous Aqueous Resolution of Potassium Salt of 4-Sulfobutyl Ester of 2-(4-Isobutylphenyl)propanoic Acid Using 100 mg of Enzyme A at pH 7.0

10.0 millimole (mmol) of ibuprofen substrate ester 4 (the butyl sulfonate derivative) was dissolved in 100 ml of 0.2M phosphate buffer of the appropriate cation (sodium or potassium, to be the same as the substrate counterion) at pH 7.0. 100 mg of enzyme A, as the commercial preparation, was added directly to this solution, and the reaction mixture was capped and then shaken briefly until all the enzyme preparation had dispersed or dissolved. The reaction mixture was then allowed to stand at ambient temperature (20°-22° C.) for 20 hours. The reaction mixture was then diluted with 1 volume of water and 1 volume of saturated NaCl solution, acidified to a pH of 1-2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over MgSO₄.

Evaporation of the ether under reduced pressure left the resolved ibuprofen acid product; no other purification was performed. The example of the result of resolving the racemic sulfoalkyl ibuprofen ester of 4 with protease enzyme A is summarized in Table 4. The optical rotations was measured in EtOH at a concentration c = 1.0 for the ibuprofen acid product.

EXAMPLE 6.2.1.5: Homogeneous Aqueous Resolution of Sodium Salt of 4-Sulfomethyl Ester of 2-(4-Isobutylphenyl)propanoic Acid Using 100 mg of Enzyme B at pH 7.0

10.0 millimole (mmol) of ibuprofen substrate ester 1 was dissolved in 100 ml of 0.2M phosphate buffer of the appropriate cation (sodium or potassium, to be the same as the substrate counterion) at pH 7.0. 100 mg of enzyme B, as the commercial preparation, was added directly to this solution, and the reaction mixture was capped and then shaken briefly until all the enzyme preparation had dispersed or dissolved. The reaction mixture was then allowed to stand at ambient temperature (20°–22° C.) for 20 hours. The reaction mixture was then diluted with 1 volume of water and 1 volume of saturated NaCl solution, acidified to a pH of 1–2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over $MgSO_4$.

Evaporation of the ether under reduced pressure left the resolved ibuprofen acid product; no other purification was performed. The example of the result of resolving the racemic sulfoalkyl ibuprofen ester of 1 with protease enzyme B is summarized in Table 4. The optical rotation was measured in EtOH at a concentration $c = 1.0$ for the ibuprofen acid product.

EXAMPLE 6.2.1.6: Homogeneous Aqueous Resolution of Sodium Salt of 4-Sulfomethyl Ester of 2-(4-Isobutylphenyl)propanoic Acid Using 100 mg of Enzyme C at pH 7.0

10.0 millimole (mmol) of ibuprofen substrate ester 1 was dissolved in 100 ml of 0.2M phosphate buffer of the appropriate cation (sodium or potassium, to be the same as the substrate counterion) at pH 7.0. 100 mg of enzyme C, as the commercial preparation, was added directly to this solution, and the reaction mixture was capped and then shaken briefly until all the enzyme preparation had dispersed or dissolved. The reaction mixture was then allowed to stand at ambient temperature (20°–22° C.) for 20 hours. The reaction mixture was then diluted with 1 volume of water and 1 volume of saturated NaCl solution, acidified to a pH of 1–2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over $MgSO_4$.

Evaporation of the ether under reduced pressure left the resolved ibuprofen acid product; no other purification was performed. The example of the result of resolving racemic sulfoalkyl ibuprofen ester of 1 with the protease enzyme C is summarized in Table 4. The optical rotations was measured in EtOH at a concentration $c = 1.0$ for the ibuprofen acid product.

EXAMPLE 6.2.1.7: Homogeneous Aqueous Resolution of Sodium Salt of 4-Sulfomethyl Ester of 2-(4-Isobutylphenyl)propanoic Acid Using 100 mg of Enzyme D at pH 7.0

10.0 millimole (mmol) of ibuprofen substrate ester 1 was dissolved in 100 ml of 0.2M phosphate buffer of the appropriate cation (sodium or potassium, to be the same as the substrate counterion) at pH 7.0. 100 mg of enzyme D, as the commercial preparation, was added directly to this solution, and the reaction mixture was capped and then shaken briefly until all the enzyme preparation had dispersed or dissolved. The reaction mixture was then allowed to stand at ambient temperature (20°–22° C.) for 20 hours. The reaction mixture was then diluted with 1 volume of water and 1 volume of saturated NaCl solution, acidified to a pH of 1–2 by the careful addition of concentrated HCl, and then immediately extracted twice with one volume of methyl-t-butyl ether or diethyl ether. The combined organic layers were backwashed twice with one volume of water, once with one volume of saturated NaCl solution, and then dried over $MgSO_4$.

Evaporation of the ether under reduced pressure left the resolved ibuprofen acid product; no other purification was performed. The example of the result of resolving the racemic sulfoalkyl ibuprofen ester of 1 with protease enzyme D is summarized in Table 4. The optical rotation was measured in EtOH at a concentration $c = 1.0$ for the ibuprofen acid product.

EXAMPLE 6.2.1.8: Homogeneous Aqueous Resolution of Potassium Salt of 3-Sulfopropyl Ester of 2-(4-Isobutyphenyl)propanoic Acid Using 150 mg of Enzyme A at pH 7.8

In this Example, 0.010 mol of ibuprofen ester 3 (the propyl sulfonate derivative) was dissolved in 100 ml 0.2M sodium phosphate buffer at pH 7.8, and 150 mg of the commercial enzyme A preparation was added. The reaction was then handled as described for Examples 6.2.1.1–6.2.1.7. The result is summarized in Table 5.

EXAMPLE 6.2.1.9: Homogeneous Aqueous Resolution of Potassium Salt of 3-Sulfopropyl Ester of 2-(4-Isobutyphenyl)propanoic Acid Using 150 mg of Enzyme B at pH 7.8

In this Example, 0.010 mol of ibuprofen ester 3 (the propyl sulfonate derivative) was dissolved in 100 ml 0.2M sodium phosphate buffer at pH 7.8, and 150 mg of the commercial enzyme B preparation was added. The reaction was then handled as described for Examples 6.2.1.1–6.2.1.7. The result is summarized in Table 5.

TABLE 5

| EXAMPLE # | ENZYME # | SUBSTRATE # | Mgs ACID PRODUCED | % CONVERSION | $[\alpha]_D$ EtOH $C = 1$ | % e.e. | ABSOLUTE CONFIGURATION |
|---|---|---|---|---|---|---|---|
| 6.2.1.8 | (A) | 3 | 970 | 47.1 | −55.7° | 97.7 | R |
| 6.2.1.9 | (B) | 3 | 750 | 36.4 | −56.2° | 98.6 | R |
| 6.2.1.10 | (D) | 3 | 660 | 32.0 | −51.9° | 91.0 | R |

EXAMPLE 6.2.1.10: Homogeneous Aqueous Resolution of Potassium Salt of 3-Sulfopropyl Ester of 2-(4-Isobutyphenyl)propanoic Acid Using 150 mg of Enzyme D at pH 7.8

In this Example, 0.010 mol of ibuprofen ester 3 (the propyl sulfonate derivative) was dissolved in 100 ml 0.2M sodium phosphate buffer at pH 7.8, and 150 mg of the commercial enzyme D preparation was added. The reaction was then handled as described for Examples 6.2.1.1–6.2.1.7. The result is summarized in Table 5.

EXAMPLE 6.2.1.11: Homogeneous Aqueous Resolution of Potassium Salt of 3-Sulfopropyl Ester of 2-(4-Isobutyphenyl)propanoic Acid Using 30 mg of Enzyme E at pH 7.0

In this Example, 0.010 mol of ibuprofen ester 3 (the propyl sulfonate ester) was dissolved in 100 ml 0.2M sodium phosphate buffer at pH 7.8, and 30 mg of Pig Liver Esterase (E) (from Sigma, product #E-3128) was added as the commercially supplied liquid preparation ples 6.2.1.1–6.2.1.7. The result of the resolution conducted is summarized in Table 8.

TABLE 7

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.12 | (A) | 2 | 780 | 38 | −57.3° | >99 | R |
| 6.2.1.13 | (B) | 2 | 500 | 24 | −51.4° | 90.0 | R |

TABLE 8

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.14 | (B) | 4 | 410 | 20.0 | −52.5° | 92.1 | R |
| 6.2.1.15 | (C) | 4 | 450 | 22.0 | −35.2° | 61.7 | R |

The reaction was then handled as described for Examples 6.2.1.1–6.2.1.7. The results are summarized in Table 6.

EXAMPLE 6.2.1.12: Homogeneous Aqueous Resolution of Sodium Salt of 2-Sulfoethyl Ester of 2-(4-Isobutylphenyl)propanoic Acid Using 150 mg of Enzyme A at pH 7.0

In this Example, 0.010 mol of ibuprofen ester 2 (the ethyl sulfonate ester in the form of its potassium salt) were dissolved in 125 ml of 0.2M sodium phosphate buffer at pH 7.0, and 150 mg of enzyme A was added to the reaction mixture as the commercially supplied preparation. The reaction was allowed to proceed for 18 hours, and the EXAMPLE 6.2.1.15: Homogeneous Aqueous Resolution of Potassium Salt of 4-Sulfobutyl Ester of 2-(4-Isobutylphenyl)propanoic Acid Using 100 mg of Enzyme C at pH 7.0

In this Example, 0.010 mol of ibuprofen ester 4 (the sulfobutyl ester) was dissolved in 100 ml of 0.2 M sodium phosphate buffer at pH 7.0. 100 mg of enzyme C, as the commercially supplied preparation, was then added and the reaction handled as described in Examples 6.2.1.1–6.2.1.7. The result of the resolution conducted is summarized in Table 8.

EXAMPLE 6.2.1.16: Homogeneous Aqueous Resolution of Disodium Salt of the Phosphoric Acid

TABLE 6

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.11 | (E) | 3 | 250 | 12.1 | −50.2° | 88.0 | R |

EXAMPLE 6.2.1.13: Homogeneous Aqueous Resolution of Sodium Salt of 2-Sulfoethyl Ester of 2-(4-Isobutylphenyl)propanoic Acid Using 150 mg of Enzyme B at pH 7.0

In this Example, 0.010 mol of ibuprofen ester 2 (the ethyl sulfonate ester in the form of its potassium salt) were dissolved in 125 ml of 0.2M sodium phosphate buffer at pH 7.0, and 150 mg of enzyme B was added to the reaction mixture as the commercially supplied preparation. The reaction was allowed to proceed for 18 hours, and the resulting product mixture was then worked-up as described above for Examples 6.2.1.1–6.2.1.7. The Example of the result of ibuprofen resolution is summarized in Table 7.

EXAMPLE 6.2.1.14: Homogeneous Aqueous Resolution of Potassium Salt of 4-Sulfobutyl Ester of 2-(4-Isobutylphenyl)propanoic Acid Using 100 mg of Enzyme B at pH 7.0

In this Example, 0.010 mol of ibuprofen ester 4 (the sulfobutyl ester) was dissolved in 100 ml of 0.2M sodium phosphate buffer at pH 7.0. 100 mg of enzyme B, as the commercially supplied preparation, was then added and the reaction handled as described in Exam- Ester of the 2-Hydroxyethyl Ester of 2-(4-Isobutylphenyl)propanoic Acid Using 100 mg of Enzyme C at pH 7.0

Here, 0.010 mol of ibuprofen ester 5 (the disodium salt of ethyl phosphate ester) were dissolved in 100 ml 0.2M sodium phosphate buffer at pH 7.0. Next, 100 mg of enzyme C, as the commercially supplied preparation, was added and the reaction handled as described in Examples 6.2.1.1–6.2.1.7. The result of the ibuprofen resolution is summarized in Table 9.

EXAMPLE 6.2.1.17: Homogeneous Aqueous Resolution of Iodide Salt of 2-(N,N,N-Trimethylammonium)ethyl Ester of 2-(4-Isobutylphenyl)propanoic Acid Using 100 mg of Enzyme A at pH 7.0

0.010 mol of the iodide salt of trimethylammonium-methyl ester of ibuprofen (Compound 10) was dissolved in 100 ml of 0.2M sodium phosphate buffer

TABLE 9

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.16 | (C) | 5 | 110 | 5.3 | −43.1° | 75.6 | R |

The result of the ibuprofen resolution is summarized in Table 10.

EXAMPLE 6.2.1.18: Homogeneous Aqueous Resolution of Methyl Sulfate Salt of 2-(N,N,N-Trimethylammonium)ethyl Ester of 2-(6-Methoxy-2-naphthyl)propanoic Acid Using 100 mg of Enzyme F at pH 7.0

10 mmol each of the ethyl trimethyammoniumalkyl ester of naproxen (11) were dissolved in 100 ml of 0.2M $Na_3PO_4$ buffer at pH 7.0, and 100 mg of protease (Prozyme 6) (F) added. The enzymatic reaction mixtures were capped and briefly shaken until all the substrate had dissolved, and the enzyme had completely dissolved or dispersed. The reactions were then incubated at 25° C. for 18 hours. The reaction mixtures were acidified to a pH of 1 to 2 by the careful addition of concentrated HCl, diluted with 2 volumes of water, and extracted with ether (2×200 ml). The combined organic layers were backwashed with water, (2×300 ml), once with saturated NaCl, and dried over $MgSO_4$. Evaporation of the ether left a white solid. The result is summarized below in Table 11. Rotations were measured at c=1 in $CHCl_3$.

EXAMPLE 6.2.1.20: Homogeneous Aqueous Resolution of Potassium Salt of the 3-Sulfopropyl Ester of 2-(6-Methoxy-2-naphthyl)propanoic Acid Using 150 m of Enzyme A at pH 7.8

This Example demonstrates resolution of naproxen esters analogous to those of ibuprofen as described above. While not as water-soluble as their ibuprofen counterparts, the alkyl sulfonate esters of naproxen still have considerable utility as substrates in enzymatic resolution. Specifically, 0.010 mol of the sulfopropyl ester of naproxen (Compound 7) is dispersed in 125 ml of 0.2M sodium phosphate buffer at pH 7.8. 150 mg of Protease XXIII (A), as the commercially available preparation, was added to the reaction mixture, the reaction vessel was capped, and the entire heterogeneous reaction mixture was shaken in a wrist-action shaker for 18 hours. The reaction was then diluted with water until all solid material had dissolved, and the mixture was then acidified to a pH of 1–2 by the careful addition of concentrated HCl. This mixture was then extracted twice with 200 ml of diethyl ether. The com-

TABLE 10

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.17 | (A) | 10 | 620 | 30.1 | −60.0 | >99 | R |

TABLE 11

| EXAMPLE # | ENZYME # | SUBSTRATE # | Mgs ACID PRODUCED | % CONVERSION | $[\alpha]_D$ $CHCl_3$ C = 1 | % e.e. | ABSOLUTE CONFIGURATION |
|---|---|---|---|---|---|---|---|
| 6.2.1.18 | F | 11 | 250 | 24.3 | −0.228° | 34.0 | R |
| 6.2.1.19 | F | 12 | 350 | 34.0 | −0.145° | 21.6 | R |

EXAMPLE 6.2.1.19: Homogeneous Aqueous Resolution of Methyl Sulfate Salt of 2-(N,N,N-Trimethylammonium)propyl Ester of 2-(6-Methoxy-2-naphthyl)propanoic Acid Using 100 mg of Enzyme F at pH 7.0

10 mmol each of the propyl trimethyammoniumalkyl ester of naproxen (12) were dissolved in 100 ml of 0.2M $NaPO_4$ buffer at pH 7.0, and 100 mg of protease (Prozyme 6) (F) added. The enzymatic reaction mixtures were capped and briefly shaken until all the substrate had dissolved, and the enzyme had completely dissolved or dispersed. The reactions were then incubated at 25° C. for 18 hours. The reaction mixtures were acidified to a pH of 1 to 2 by the careful addition of concentrated HCl, diluted with 2 volumes of water, and extracted with ether (2×200 ml). The combined organic layers were backwashed with water, (2×300 ml), once with saturated NaCl, and dried over $MgSO_4$. Evaporation of the ether left a white solid. The result is summarized below in Table 11. Rotations were measured at c=1 in $CHCl_3$.

bined organic layers were backwashed twice with one volume of water, once with one volume of saturated NaCl, and the organic phase was then dried over $MgSO_4$. Evaporation of the ether under reduced pressure left the resolved naproxen acid. No further purification was performed. The optical rotation of the product was measured in $CHCl_3$ at a concentration c=1.0. The result of the naproxen resolution employing this particular substrate/enzyme combination is summarized in Table 12.

EXAMPLE 6.2.1.21: Homogeneous Aqueous Resolution of Potassium Salt of 3-Sulfopropyl Ester of 2-(4-Isobutyphenyl)propanoic Acid Using 1000 mg of Enzyme A at pH 7.0

A concentrated solution, about 1M, of the sulfopropyl ester of ibuprofen (2-(4-isobutylphenyl)propanoic acid) (Compound 3) was prepared by adding 14.64 gm of the potassium salt of the ester into

TABLE 12

| EXAMPLE # | ENZYME # | SUBSTRATE # | Mgs ACID PRODUCED | % CONVERSION | $[\alpha]_D$ $CHCl_3$ C = 1 | % e.e. | ABSOLUTE CONFIGURATION |
|---|---|---|---|---|---|---|---|
| 6.2.1.20 | (A) | 7 | 220 | 10.7 | −51.9° | 78.0 | R |

Evaporation of the ether left a white solid. The result is summarized below in Table 11. Rotations were measured at c=1 in $CHCl_3$.

The reaction was started by addition of 1.00 gm of protease (A) from the fungus *Aspergillus oryzae* (from Sigma Chemical Company, Protease Type XXIII, 3.7 units per mg solid). The mixture was stirred with a magnetic stir bar and the pH was controlled at 7.0 using 4.221M sodium hydroxide.

After 23.9 hours at room temperature, 2.74 ml of sodium hydroxide were added, indicating a 29% conversion of the racemic ester to acid. The mixture was acidified to pH 1.5–2 with concentrated HCl and extracted with two 100 ml volumes of hexane. The hexane was dried with MgSO$_4$ and evaporated to dryness, yielding about 1.9 gm of solid. The optical rotation of this material was measured on a polarimeter yielding a value for $[\alpha]_D$ of $-55.5°$ (at c=1.02 in ethanol).

EXAMPLE 6.2.1.22: Homogeneous Aqueous Resolution of Sodium Salt of 4-Sulfomethyl Ester of 2-(4-Isobutylphenyl)propanoic Acid Using 100 mg of Enzyme F at pH 7.0

A solution of the sulfomethyl ester of ibuprofen (1 Compound) was prepared by adding 3.22 gm of the sodium salt of the ester (93% chemical purity) to 100 ml of 0.2M sodium phosphate buffer (pH 7.0). The reaction was started by adding 100 mg of the protease (F) from the fungus *Aspergillus oryzae* (from Amano Enzyme Corporation, Prozyme 6, 60,000 units per mg of solid).

After 20 hours at room temperature, the solution was acidified to pH 2 and extracted with 3 volumes of diethyl ether. The aqueous phase was saved for subsequent workup. The ether phase was washed with two volumes of After 20 hours at room temperature, the solution was acidified to pH 2 and extracted with 3 volumes of diethyl ether. The aqueous phase was saved for subsequent workup. The ether phase was washed with two volumes of distilled water and then one volume of saturated sodium chloride, and then it was dried over MgSO$_4$ and subsequently evaporated to dryness. The resolved ibuprofen product recovered was 930 mg of white powder, indicating 45% conversion of racemic ester to acid. The optical rotation was $-0.580°$ (measured at c=1 in ethanol), indicating the R isomer of ibuprofen.

The aqueous phase from the above extraction was raised to pH 12 for 30 minutes to hydrolyze the remaining, unconverted ester. The pH was dropped to 2, and the above procedure to recover ibuprofen acid was repeated. 900 mg of white powder were isolated, indicating a 43% conversion. The optical rotation was +0.566° (measured at c=1 in ethanol), indicating the S isomer of ibuprofen.

EXAMPLE 6.2.1.23: Homogeneous Aqueous Resolution of Potassium Salt of 2-Sulfoethyl Ester of 2-(6-Methoxy-2-naphthyl) propanoic Acid Using 150 mg of Enzyme A at pH 7.8

0.010 mol of naproxen ester 8 (the potassium salt of the ethyl sulfonate ester) was dispersed in 125 ml of 0.2M sodium phosphate buffer at pH 7.8. 150 mg of enzyme A, as the commercially available preparation, were added, and the reaction handled as described in Example 6.2.1.1. The result of enzymatic naproxen resolution is summarized in Table 13.

EXAMPLE 6.2.1.24: Homogeneous Aqueous Resolution of Potassium Salt of the Sulfuric Acid Ester of the 3-Hydroxylpropyl Ester of 2-(4-Isobutylphenyl)propanoic Acid Using 100 mg of Enzyme A at pH 7.0

0.010 mol of ibuprofen ester 6 (the compound) were dissolved in 100 ml of 0.2M sodium phosphate buffer at pH 7.0. 100 mg of enzyme A was added as the commercially available preparation, and the reaction handled as described above in Examples 6.2.1.1–6.2.1.7. The results of resolution is summarized in Table 14.

EXAMPLE 6.2.1.25: Homogeneous Aqueous Resolution of Sodium Salt of Sulfomethyl Ester of 2-(6-Methoxy-2-naphthyl)propanoic Acid Using 100 mg of Enzyme A at pH 7.5

2.0 gm (0.0058 mole) of naproxen ester 9 (the sulfomethyl compound) was dissolved in 400 ml of 50 mM sodium phosphate buffer at pH 7.5. To the reaction were added 100 mg of Protease XXIII (A) as the commercially available preparation. After the enzyme had dissolved, the reaction mixture was incubated at 25 degrees for 16 hours. The reaction mixture was then acidified to pH 1–2 by the careful dropwise addition of concentrated HCl, and then it was extracted with ether (3×150 ml). The aqueous layer was retained. The combined organic layers were backwashed with water (2×100 ml), and these aqueous washings were added to the previously retained aqueous layer of the reaction. The ether layer was then washed once with 100 ml of brine, and dried over MgSO$_4$.

Evaporation of the ether left 240 mg of optically enriched naproxen acid, indicating that the enzymatic hydrolysis of Compound 9 had proceeded to 18% conversion.

TABLE 14

| EXAMPLE # | ENZYME # | SUBSTRATE # | Mgs ACID PRODUCED | % CONVERSION | $[\alpha]_D$ EtOH C = 1 | % e.e. | ABSOLUTE CONFIGURATION |
|---|---|---|---|---|---|---|---|
| 6.2.1.24 | (A) | 6 | 500 | 24.3 | −0.550 | 96.5 | R |

This product had a rotation of −0.410 degrees at c=1 in CHCl$_3$, indicating that the R isomer of naproxen was present in 61.2% enantiomeric excess.

The combined aqueous layers from this work-up were made basic to pH 12, as carefully measured on a pH meter. The aqueous solution was stirred at this pH and at ambient temperature for 30 minutes. The aqueous solution was then acidified by the careful addition of concentrated HCl, to lower the pH to a value of 2. This solution was then extracted with ether (3×150 ml). The combined organic layers were backwashed first with water (2×100 ml), and the with 100 ml of brine, and the ether phase was subsequently dried over MgSO$_4$. Evaporation of the ether left 490 mg of a white powder. At c=1 in CHCl$_3$, this product had a rotation of +0.305 degrees, indicating the S isomer of Naproxen present in 45.5% enantiomeric excess.

TABLE 13

| EXAMPLE # | ENZYME # | SUBSTRATE # | Mgs ACID PRODUCED | % CONVERSION | $[\alpha]_D$ CHCl$_3$ C = 1 | % e.e. | ABSOLUTE CONFIGURATION |
|---|---|---|---|---|---|---|---|
| 6.2.1.23 | (A) | 8 | 70 | 3.0 | −0.387 | 59.0 | R |

EXAMPLE 6.2.1.26: Homogeneous Aqueous Resolution of Potassium Salt of 3-Sulfopropyl Ester of 2-Chloropropanoic Acid Using 20 mg of Enzyme B at pH 7.0

A solution of the sulfopropyl ester of 2-chloropropanoic acid (13) was prepared by adding 8.05 gm of the potassium salt of the ester to 300 ml of 0.1M potassium phosphate buffer (pH 7.0). The reaction was started by adding 20 mg of the subtilisin protease (B) (from Sigma Chemical Company, Protease VIII).

The reaction was stopped after 25% conversion as measured by titrimetry. The solution was acidified to pH 1.5 with concentrated sulfuric acid and extracted with 3 volumes of t-butyl methyl ether. The ether was washed with 4 volumes of saturated sodium chloride, dried over MgSO$_4$, and then the solvent was removed in a rotary evaporator. 1.07 gm of yellow liquid was isolated and tested for acid purity by titration, yielding a chemical purity of 88.9%. The optical rotation of the liquid was +0.022° (c=1, chloroform), indicating the R isomer of chloropropanoic acid. Thin layer chromatography of the acid showed similar properties to a racemic chloropropanoic acid standard.

EXAMPLE 6.2.1.27: Homogeneous Aqueous Resolution of Potassium Salt of the Sulfomethyl Ester of (+)-S-3-Benzoylthio-2-methylpropanoic Acid Using 100 mg of Enzyme B at pH 7.0

10.0 mmol of ester 16 was dissolved in 100 ml 0.2M Na$_3$PO$_4$ buffer at pH 7.0, and 100 mg of enzyme B, as the commercially available preparation, were added directly to the solution. The reaction mixture was capped, and shaken briefly until all the enzyme had dispersed and dissolved. The reaction mixture was then incubated at 25° C. for 18 hours. The reaction was then handled as described for Examples 6.2.1.1–6.2.1.7. The result is summarized in Table 15.

EXAMPLE 6.2.1.28: Homogeneous Aqueous Resolution of Potassium Salt of the Sulfomethyl Ester of (+)-S-3-Benzoylthio-2-methylpropanoic Acid Using 100 mg of Enzyme A at pH 7.0

10.0 mmol of ester 16 was dissolved in 100 ml 0.2M Na$_3$PO$_4$ buffer at pH 7.0, and 100 mg of enzyme A, as the commercially available preparation, were added directly to the solution. The reaction mixture was capped, and shaken briefly until all the enzyme had dispersed and dissolved.

The reaction flask was capped, and briefly shaken until all the enzyme had dissolved or dispersed. The enzymatic reaction mixture was then incubated at 30° C. for 1 hour, at which time it was acidified to a pH of 1 to 2 by the careful addition of concentrated HCl. The resulting mixture was diluted with one volume of water and was extracted with diethyl ether (2 times 200 ml). The ether layers were combined and backwashed with water (2 times 200 ml), saturated NaCl solution (200 ml), and then dried over MgSO$_4$. Evaporation of the ether under reduced pressure left 450 mg of an off-white solid, indicating the reaction had proceeded to 22.5% completion. This product had an optical rotation of −0.063° in EtOH at c=1.0.

EXAMPLE 6.2.1.30: Homogeneous Aqueous Resolution of Sodium Salt of 4-Sulfomethyl Ester of 2-(4-Isobutylphenyl)propanoic Acid Over Time Using 3 gm of Enzyme F at pH 7.0

In this control run, a 0.5M ester solution of (1) was prepared in 325 ml of 0.1M sodium phosphate buffer (pH 7.0). The reaction was started by adding 3 gm of the above enzyme (F). The pH was controlled at 7.0 with 8.22M sodium hydroxide. After 6.49 hours at 30° C., 6.63 ml of hydroxide were added, indicating 37.7% conversion. The reaction was allowed to continue overnight and, after 23.1 hours, a total of 7.2 ml of sodium hydroxide were added, indicating 40.9% conversion. This result of conversion as a function of time is summarized in Table 16.

6.2.2 Enzymatic Resolutions in Extractive Dispersion or Membrane Reactors

Example 6.2.2.1: Resolution of Sodium Salt of 4-Sulfomethyl Ester of 2-(4-Isobutylphenyl)propanoic Acid via Asymmetric Hydrolysis in an Extractive Dispersion Reactor A solution of the sulfomethyl ester of ibuprofen was prepared by adding 3.38 gm of the sodium salt of the ester (93% chemical purity) to 100 ml of 0.2M sodium phosphate buffer (pH 7.0) and 100 ml of hexane. In this Example, the hexane was dispersed in the reaction vessel to extract the inhibitory ibuprofen acid as it is formed. The reaction was started by adding 100 mg of the protease from the fungus *Aspergillus oryzae* (from Amano Enzyme Corporation, Prozyme 6, 60,000 units per mg of solid).

TABLE 15

| EXAMPLE # | ENZYME # | SUBSTRATE # | % CONVERSION | $[\alpha]_D$ EtOH C = 1 | % e.e. | ABSOLUTE CONFIGURATION |
|---|---|---|---|---|---|---|
| 6.2.1.27 | B | 16 | 26 | +0.046° | 10 | S |
| 6.2.1.28 | A | 16 | 53 | +0.012° | 3 | S |

The reaction mixture was then incubated at 25° C. for 18 hours. The reaction was then handled as described for Examples 6.2.1.1–6.2.1.7. The result is summarized in Table 15.

EXAMPLE 6.2.1.29: Homogeneous Aqueous Resolution of Sodium Salt of the Sulfomethyl Ester of 2-(4-Chlorophenoxy)propanoic Acid Using 35 mg of Enzyme F at pH 7.0

10 mmol of the sulfomethyl ester of 2-(4-chlorophenoxy)propanoic acid (17) (3.19 gm) were dissolved in 100 ml of 0.2M sodium phosphate buffer at pH 7.0. 35 mg of protease Enzyme F, as the commercial preparation Prozyme 6, were added to the aqueous solution.

TABLE 16

| ASYMMETRIC RESOLUTION OVER TIME | |
|---|---|
| | Conversion in Homogeneous Aqueous |
| Time (hrs) | Reaction System |
| 6.75 | 37.7% |
| 23.1 | 40.9% |

After 3.5 hours at room temperature with vigorous stirring, the solution was acidified to pH 2 and extracted with 2 volumes of hexane. The aqueous phase was saved for subsequent workup. The hexane phase was dried over MgSO$_4$ and evaporated to dryness. The resolved ibuprofen product so recovered consisted of 490 mg of white powder, indicating 24% conversion. The optical rotation was $-0.568°$ (c=1.015 in ethanol), indicating the R isomer of ibuprofen.

The aqueous phase from the above extraction was raised to pH 12 for 15 hours to hydrolyze the remaining : unconverted ester. The pH was dropped to pH 2 and the above procedure to recover ibuprofen acid was repeated. 1.13 gm of white powder was isolated. The optical rotation as measured by polarimetry was +0.207° (c=1.036 in ethanol), indicating the S isomer of ibuprofen.

EXAMPLE 6.2.2.2: Resolution of Sodium Salt of 4-Sulfomethyl Ester of 2-(4-Isobutylphenyl)propanoic Acid via Asymmetric Hydrolysis Not Associated with the Membrane in an Extractive Membrane Reactor Ibuprofen resolution and recovery are first described here in general terms, followed by a more detailed description of the experimental conditions and results.

Enzymatic resolution was conducted in an extractive membrane reactor consisting of a 1.9 m$^2$ custom-made solvent-resistant membrane module fabricated with saponified cellulose ester dialysis fibers from Cordis-Dow. Hexane was recirculated through the lumen or bores of the fibers in the module. The aqueous solution in the shell contained the enzyme and ester. While the cellulose membrane is water-wet, the membrane rejects the macromolecular enzyme (molecular weight 18,000). Therefore, the enzyme resides solely in the aqueous ester solution. As the ibuprofen acid was formed, it was extracted into the hexane phase, thereby reducing the effect of product (ibuprofen acid) inhibition on the activity of the enzyme.

To recover the acid product of enzymatic hydrolysis, the acid-containing hexane phase was then stripped of the ibuprofen acid in another membrane extraction module, a 0.85 m$^2$ custom-made solvent-resistant membrane module fabricated with polyacrylonitrile hollow fibers of the type used in ultrafiltration. The aqueous phase used to extract the ibuprofen acid from hexane in this module contained 0.1M sodium carbonate buffer at pH 9.5. The pH was maintained at this value by the addition of 8.22M sodium hydroxide as required.

A specific experimental protocol and its results are summarized below. In this Example, the aqueous stream in the extractive membrane reactor module consisted of a solution of the sulfomethyl ester of ibuprofen (1), which solution was prepared by adding 32.51 gm of the sodium salt of the ester (at 75% chemical purity) to 1000 ml of 0.1M sodium phosphate buffer (pH 7.0). The reaction was started by adding 2 gm of the protease (F) from the fungus *Aspergillus oryzae* (from Amano Enzyme Corporation, Prozyme 6, 60,000 units per gm of solid). Reaction progress was followed by automatic titrimetry using a pH-stat.

After 6.3 hours at room temperature, 4.13 ml of 8.22M sodium hydroxide had been added to the aqueous phase, indicating 50% conversion of the racemic ester (Compound 1) to ibuprofen acid. The pH 9.5 solution was then acidified to pH 2 and extracted with 2 volumes of t-butyl methyl ether. The ether phase was first washed with two volumes of distilled water, then dried over MgSO$_4$ and subsequently evaporated to dryness. The resolved ibuprofen product was recovered as about 6 gm of a white powder.

The optical rotation of the recovered product was measured by polarimetry; the experimentally determined value for $[\alpha]_D$ was $-56.7°$ (measured at c=0.815 in ethanol), thereby indicating the R isomer of ibuprofen. The sample was also analyzed by chiral HPLC using a Bakerbond DNBPG (covalent) column (4.6×250 mm), with 96.9% hexane:3.0% 2-propanol:0.1% acetonitrile as the mobile phase at 2 ml/min after derivatization with naphthalene amine. The detector was a UV spectrophotometer set at 223 nm. The retention times for the S and R ibuprofen acids were 18.5 and 20.0 min, respectively. The optical purity or enantiomeric excess of this R ibuprofen sample as determined by this chiral HPLC procedure was 99.3% (i.e., enantiomeric excess of R ibuprofen).

The aqueous phase at pH 7.0 (as recovered from the extractive membrane reactor) was mixed with 280 gm of sodium chloride to salt out the remaining unconverted ester. The ester was filtered, washed with saturated sodium chloride, and air dried. 12.8 gm of ester were recovered in this manner. A portion of this ester was hydrolyzed by raising the pH to 12 for 30 minutes. The pH was then dropped to 2, and the above-described procedure for recovery of ibuprofen acid was repeated. 680 mg of white powder were isolated. The optical rotation (as measured by polarimetry) was $[\alpha]_D = +57.4°$ (c=1.29 in ethanol), indicating the S isomer of ibuprofen. Analysis of the resolved product by chiral HPLC gave 98.9% enantiomeric excess of S ibuprofen.

EXAMPLE 6.2.2.3: Resolution of Sodium Salt of 4-Sulfomethyl Ester of 2-(4-Isobutylphenyl)propanoic Acid via Asymmetric Hydrolysis Associated with the Membrane in an Extractive Membrane Reactor with an Enzyme Activated Membrane Enzymatic resolution was conducted in an Extractive membrane reactor consisting of a 1.0 m$^2$ hemofilter (ASAHI Medical Company, PAN-150) made with polyacrylonitrile, microporous, ultrafiltration-type hollow fibers. Enzyme was immobilized in the membrane pores. Cyclohexane (350 ml) was recirculated through the shell of the module. The aqueous solution in the lumen contained the ester. As the ibuprofen acid was formed, it was extracted into the cyclohexane phase. The acid enriched organic was then stripped in another module (0.85 m$^2$ custom made solvent resistant membrane module fabricated with polyacrylonitrile, ultrafiltration hollow fibers). The aqueous phase of this module contains 0.1M sodium carbonate buffer at pH 9.5. The pH is controlled at 9.5 with 8.22M sodium hydroxide.

In one particular case, the enzyme immobilization was conducted as follows. A solution of 3 gm of lipase from *Candida cylindracea* (from Meito Sangyo Company, Lipase OF, 360,000 units per gm of solid) was prepared in 500 ml of 0.1M sodium phosphate buffer (pH 7.0). This enzyme is inactive against Compound 1. The enzyme solution was ultrafiltered from the shell into the lumen. The enzyme was retained by the membrane's ultrafiltration skin on the lumen-side of the membrane. This enzyme was then activated by recirculating 500 ml of 2.5% glutaraldehyde solution in 0.1M sodium phosphate buffer (pH 7.0). In some cases, one half of the glutaraldehyde was bound to the free amino groups of the lipase and the other aldehyde was free for further coupling. After flushing the module free of glutaraldehyde, 350 ml of phosphate buffer solution containing 6 gm of protease (F) from the *Aspergillus oryzae* (from Amano Enzyme Corporation, Prozyme 6, 60,000 units per gm of solid) was prepared. This solution was recirculated from through the shell and into the lumen by ultrafiltration. Enzyme assays measured a 70% depletion, of protease activity from the reservoir after 18 hours, indicating binding of the protease to the activated lipase in the membrane. Water flushing removed residual protease solution from the membrane.

The aqueous stream in the extractive membrane reactor consisted of a solution of the sulfomethyl ester of ibuprofen (1), which was prepared by adding 32.3 gm of the sodium salt of the ester to 500 ml of 0.1M sodium phosphate buffer (pH 7.0). The recirculation of this solution through the lumen of the enzyme activated membrane module started the reaction. Reaction progress was followed by hydroxide consumption in the carbonate reservoir as the product acid is neutralized. After 17 hours at 20° C., 0.765 ml of 8.2M sodium hydroxide were added. The carbonate buffer was acidified at pH 2 and extracted with 2 volumes of hexanes. The hexane was dried with $MgSO_4$ and subsequently evaporated to dryness. The resolved ibuprofen product was recovered as 1.76 gm of a white powder. Optical purity was determined by polarimetry; the rotation measured was −0.227° (c=1.06, ethanol), thereby indicating the R isomer of ibuprofen. Residual racemic ibuprofen present in the starting ester reduced the optical purity of the enzymatic ibuprofen product.

EXAMPLE 6.2.2.4: Resolution of Sodium Salt of 4-Sulfomethyl Ester of 2-(4-Isobutylphenyl)propanoic Acid via Asymmetric Hydrolysis Associated and Not Associated with the Membrane in an Extractive Membrane Reactor First, the extractive membrane reactor run is described. The reactor module was prepared using a 0.85 $m^2$ custom-made solvent-resistant membrane module fabricated with polyacrylonitrile, skinned microporous or ultrafiltration-type hollow fiber membranes, an experimental fiber made by Sepracor, Inc. 250 ml of 80% cyclohexane:20% toluene mixture were recirculated through the shell of the module. The aqueous solution (0.1M sodium phosphate buffer) in the lumen contained the enzyme and ester. The ultrafiltration-type membrane used here does not reject the protease enzyme; therefore, the enzyme resides in the ester solution as well as in the pores of the membrane. As the ibuprofen acid was formed, it was extracted into the organic phase. The acid enriched organic phase was then stripped in another membrane extraction module (0.85 $m^2$ custom-made solvent-resistant membrane module fabricated with polyacrylonitrile ultrafiltration-type hollow fiber membranes). The aqueous phase of this module contained 0.1M sodium carbonate buffer at pH 9.5. The pH was controlled at 9.5 with 8.22 M sodium hydroxide.

In one particular case, a 0.5M solution of ester was prepared by adding 48.3 gm of the sodium salt of the sulfomethyl ester of ibuprofen (1) (93% chemical purity) into 300 ml of 0.1M sodium phosphate buffer (pH 7.0). The reaction was started by adding 3 gm of the protease (F) from the fungus *Aspergillus oryzae* (from Amano Enzyme Corporation, Prozyme 6, 60,000 units per gm of solid) to the ester solution. After 6.75 hours at 30° C., 8.20 ml of 8.22M sodium hydroxide were added indicating 48.3% conversion of the racemic ester to the acid, indicating substantially higher productivity than that obtained in the homogeneous aqueous reaction system of Example 6.2.1.30 (see Table 16).

EXAMPLE 6.2.2.5: Resolution of Methyl Ester of 2-(6-Methoxy-2-naphthyl)propanoic Acid via Asymmetric Hydrolysis in a Multiphasic Bioreactor A multiphase bioreactor was prepared using a 0.85 $m^2$ custom made solvent-resistant membrane module fabricated with polyacrylonitrile, ultrafiltration hollow fibers from ASAHI Medical Company PAN-200 hemofilter. The enzyme (Enzyme G), a lipase derived from *Candida cylindracea*, was purchased from Genzyme Corporation, with a specific activity of 10,500 units/mg (1 unit=1 umol of fatty acid liberated from olive oil per hour at 37° C. and pH 7.7). This enzyme as known to hydrolyze stereoselectively esters of naproxen (2-(6-methoxy-2-naphthyl)propanoic acid).

3.0 grams of the lipase were dissolved in 500 mls of distilled water; this solution was recirculated in an ultrafiltration mode from the shell into the lumen and back to the reservoir for 30 minutes. The ultrafiltrate was then collected until the reservoir was empty, and methyl isobutyl ketone (MIBK) was then pumped into the shell and recirculated at 400–450 ml/min with a 5–7 psig shell pressure to remove any remaining enzyme solution from the shell. A sample of the ultrafiltrate was assayed on triacetin, showing that less than 5% of the enzymatic activity remained, compared to the starting solution. Two hundred milliliters of potassium phosphate buffer (25 mM, pH 8.5) were recirculated through the shell at 350–400 ml/min.

The methyl ester of racemic naproxen (Compound 18) was synthesized by Method B7. It should be noted that the water solubility of this ester is roughly 0.1–0.2 mM while its solubility in MIBK is about 1.3M. 42 grams of the solid Naproxen ester were slowly added to the MIBK to achieve a final concentration of 0.75M with a total organic volume of roughly 225 ml. The pH was controlled at 8.50±0.01 with 0.25M NaOH using a Brinkman Dosimat 665 pH-stat.

The reaction was monitored by periodically withdrawing aqueous samples and determining the Naproxen concentration spectophotometrically ($\epsilon_{320}=1250M^{-1}$). The average rate for the first 45 minutes was 35 umol/hr. The hydrolytic rate for the next 36 hours was in the range of 9 to 14 umol/hr.

EXAMPLE 6.2.2.6: Resolution of 2,2,2-Trifluoroethyl Ester of 2-(4-Isobutylphenyl)propanoic Acid via Asymmetric Hydrolysis in a Multiphasic Bioreactor A reactor was prepared as described in Example 6.2.2.5 (naproxen) using essentially the same mode of loading the enzyme, 3.0 grams of Candida lipase (Enzyme G, from Genzyme Corporation) were ultrafiltered from the shell into the lumen. The enzyme was then washed with 2–3 l of distilled water and 1 l of potassium phosphate buffer (0.10 M, pH 7.7). The module was then drained.

The trifluoroethyl ester of racemic ibuprofen (2-(4-isobutylphenyl)propanoic acid) (Compound 19) was synthesized by Method B8. The water solubility of the ester is roughly 0.4 mM. Two hundred and sixty-five grams of the liquid ibuprofen ester were pumped into the shell of the reactor and recirculated at 400–450 ml/min with an outlet pressure of 5–8 psig. No organic solvent was required as the substrate is already a water-immiscible liquid. Phosphate buffer was immediately pumped into the lumen and recirculated at 400–450 ml/min. The aqueous volume was about 650 ml, and the pH was controlled at 7.7±0.01 with 1.0M NaOH.

The reaction was monitored by following acid production based on hydroxide titration data. The average hydrolytic rate for the first 60 minutes was 160 umol/min. The aqueous buffer was replaced after 76 minutes and acidified to pH 2.0 with concentrated HCl in the presence of about 200 ml of chloroform. The chloroform was washed with a saturated sodium chloride solution and dried with magnesium sulfate. The ibuprofen solution was evaporated to dryness, and 2.13 gms of crude ibuprofen were recovered. Over the next 76 hours, the average hydrolysis rate was 21 umol/min as measured by titrimetry. This corresponded to about 9.8% conversion to acid. The aqueous reservoir was changed six times over this period, yielding about 15 grams of ibuprofen. This material was recrystallized from hexane. The material has a melting point of 51°-53° C. (literature value for S-ibuprofen 50°-52° C. while racemic ibuprofen 75°-77° C.). The specific optical rotation of this material was $[\alpha]_D = +55.0°$ (c=1, ethanol).

EXAMPLE 6.2.2.7: Resolution of Octyl Ester of 2-Chloropropanoic Acid via Asymmetric Hydrolysis in a Multiphasic Bioreactor An enzyme solution was prepared by dissolving 30 grams of Candida lipase (Enzyme H, Mol. Wt. 100,000; Sigma Chemical Co. Cat #L 1754) in 0.75 ml of water and then filtering this solution to remove the insoluble material. The enzyme was loaded into a 0.85 m$^2$ custom-made solvent-resistant membrane module fabricated with anisotropic polyacrylonitrile (PAN) hollow fibers taken from a PAN-200 hemofilter (ASAHI Medical Co.). The morphology of this membrane is such that it can be described as an asymmetric hydrophilic inside-skinned hollow fiber characterized by 90% rejection of proteins with a molecular weight higher than 50,000. The enzyme solution was recirculated from the shell side to the lumen side and back to the solution reservoir in an ultra-filtration mode. Throughout the loading process the pressure difference between the shell and lumen compartments was kept to 8 psi by adjusting the ultrafiltration rate (generally between 200 to 20 ml/min). The procedure was completed in one hour.

After loading the enzyme to the reactor, recirculation of 210 gm. (0.96 mole) of racemic 2-chloropropionate octyl ester (Compound 20) on the shell side was started. The solubility of this ester in water is approximately 1.2 mM. The recirculation rate was 400 ml/min and the average pressure on the shell compartment was kept at 6.5 psi by adjusting a throttling valve at the shell side exit. On the lumen side 1 liter of 0.05M K was recirculated at a rate of 400 ml/min. The pH of the aqueous reservoir was kept at 7.0 by addition of 1M NaOH. The reactor was run continuously for 6.8 days.

The reaction progress and rate were monitored by following the caustic consumption. At the beginning of the experiment the rate of ester hydrolysis was 186 umoles/min and at the end it was 25 umoles/min. The experiment was terminated when 41% of the initial ester had been hydrolyzed. The optical rotation of the final ester mixture was $[\alpha]_D = -0.41°$ (c=50, CHCl$_3$). The initial ester substrate to the reactor had no optical rotation.

6.2.3 Determination of Enzyme Resolution Activity and Specificity

EXAMPLE 6.2.3.1: Determination of Activity and Specificity of Enzyme B with Respect to the Two Enantiomers of S-3-Acetylthio-2-methylpropanoic Acid Sulfomethyl Ester 15 ml of a solution containing one enantiomer of the ester at a concentration of 50 mM, and Na$_3$PO$_4$ buffer at 50 mM and pH 7.6 wa observed using pH stat device 0.1 ml of a 50 mg/ml solution of enzyme B, made up from the commercially available preparation in 50 mM Na$_3$PO$_4$ buffer at pH 7.6, were added. Rates of hydrolysis of both enantiomers of the ester compound were determined for the enzyme. The ratio of the rates of hydrolysis for the two enantiomers for the two enantiomers with respect to the enzyme indicate the stereospecificity of that enzyme's hydrolytic action on the racemic mixture of the ester. No evidence for the hydrolysis of the acetylthio ester portion of the substrate molecule was found. The result is summarized in Table 17.

EXAMPLE 6.2.3.2: Determination of Activity and Specificity of Enzyme I with Respect to the Two Enantiomers of S-3-Acetylthio-2-methylpropanoic Acid Sulfomethyl Ester 15 ml of a solution containing one enantiomer of the ester at a concentration of 50 mM, and Na$_3$PO$_4$ buffer at 50 mM and pH 7.6 was observed using a pH stat device. 0.1 ml of a 50 mg/ml solution of protease enzyme I, made up from the commercially available preparation in 50 mM Na$_3$PO$_4$ buffer at pH 7.6, were added. Rates of hydrolysis of both enantiomers of the ester compound were determined for the protease enzyme. The ratio of the rates of hydrolysis for the two enantiomers for the two enantiomers with respect to the enzyme indicate the stereospecificity of that enzyme's hydrolytic action on the racemic mixture of the ester. No evidence for the hydrolysis of the acetylthio ester portion of the substrate molecule was found. The results are summarized in Table 17.

EXAMPLE 6.2.3.3: Determination of Activity and Specificity of Enzyme A with Respect to the Two Enantiomers of S-3-Acetylthio-2-methylpropanoic Acid Sulfomethyl Ester 15 ml of a solution containing one enantiomer of the ester at a concentration of 50 mM, and Na$_3$PO$_4$ buffer at 50 mM and pH 7.6 was observed using a pH stat device. 0.1 ml of a 50 mg/ml solution of enzyme A, made up from

TABLE 17

| Example # | Enzyme | Rate (umols/hr/mg) | | Rate Ratio |
|---|---|---|---|---|
| | | L-isomer | D-isomer | L/D |
| 6.2.3.1 | (B) | 135 | 65 | 2.1 |
| 6.2.3.2 | (I) | 105 | 63 | 1.7 |
| 6.2.3.3 | (A) | 12 | 5.3 | 2.3 |
| 6.2.3.4 | (J) | 65 | 61 | 1.1 |
| 6.2.3.5 | (D) | 29 | 27 | 1.1 |

Rates of hydrolysis of both enantiomers of the ester compound were determined for the enzyme. The ratio of the rates of hydrolysis for the two enantiomers for the two enantiomers with respect to the enzyme indicate the stereospecificity of that enzyme's hydrolytic action on the racemic mixture of the ester. No evidence for the hydrolysis of the acetylthio ester portion of the substrate molecule was found. The results are summarized in Table 17.

EXAMPLE 6.2.3.4: Determination of Activity and Specificity of Enzyme J with Respect to the Two Enantiomers of S-3-Acetylthio-2-methylpropanoic Acid Sulfomethyl Ester 15 ml of a solution containing one enantiomer of the ester at a concentration of 50 mM, and Na$_3$PO$_4$ buffer at 50 mM and pH 7.6 was observed using a pH stat device. 0.1 ml of a 50 mg/ml solution of Enzyme J, made up from the commercially available preparation in 50 mM Na$_3$PO$_4$ buffer at pH 7.6, were added. Rates of hydrolysis of both enantiomers of the ester compound were determined for the enzyme. The ratio of the rates of hydrolysis for the two enantiomers for the two enantiomers with respect to the enzyme indicate the stereospecificity of that enzyme's hydrolytic action on the racemic mixture of the ester. No evidence for the hydrolysis of the acetylthio ester portion of the substrate molecule was found. The results are summarized in Table 17.

EXAMPLE 6.2.3.5: Determination of Activity and Specificity of Enzyme D with Respect to the Two Enantiomers of S-3-Acetylthio-2-methylpropanoic Acid Sulfomethyl Ester 15 ml of a solution containing one enantiomer of the ester at a concentration of 50 mM, and Na$_3$PO$_4$ buffer at 50 mM and pH 7.6 was observed using a pH stat device. 0.1 ml of a 50 mg/ml solution of enzyme D, made up from the commercially available preparation in 50 mM Na$_3$PO$_4$ buffer at pH 7.6, were added. Rates of hydrolysis of both enantiomers of the ester compound were determined for the enzyme. The ratio of the rates of hydrolysis for the two enantiomers for the two enantiomers with respect to the enzyme indicate the stereospecificity of that enzyme's hydrolytic action on the racemic mixture of the ester. No evidence for the hydrolysis of the thioacetyl ester portion of the substrate molecule was found. The results are summarized in Table 17.

The present invention is not intended to be limited in scope by the above experiments or by the reactants, solvents, solutions, membranes or catalysts used since each is intended merely as an illustration of the invention. In addition, any composition of matter or set utilized in the claimed method which is functionally equivalent to those set forth herein is intended to be within the scope of this invention. Indeed, various modifications of the invention, in addition to those shown and described herein, will become apparent to those skilled in the art from the foregoing description and accompanying specification. Such modifications are intended to fall within the scope of the appended claims.

We claim:

1. A method for preparing an ester compound of formula (II),

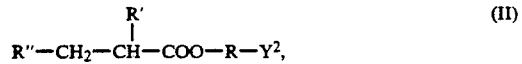

wherein R' is selected from the group consisting of aryl, aryloxy, alkyl, hydroxyl, protected hydroxyl and halogen, R" is selected from the group consisting of hydrogen, benzyl, protected thiol and thiol, R is alkyl, Y$^2$ is —SO$_3$H and salt thereof, comprising:

a) reacting a compound of formula (III),

wherein R' is selected from the group consisting of aryl, aryloxy, alkyl, hydroxyl, protected hydroxyl and halogen and R" is selected from the group consisting of hydrogen, benzyl, protected thiol and thiol, with a base to form the carboxylate ion of a compound of formula III, b) reacting said carboxylate ion of the compound of formula III formed in step a) with hydroxyalkyl sulfonic acid sultone, and c) isolating the compound of formula II formed in step b).

2. The method of claim 1, wherein the protected thiol is protected with a protecting group selected from the group consisting of acetyl, benzoyl and thiocarbamoyl.

3. The method of claim 1, wherein the aryloxy group is selected from the group consisting of 4-hydroxyphenoxy, 4-chlorophenoxy and 2-methyl-4-chlorophenoxy.

4. The method of claim 1, wherein R' is a halogen selected from the group consisting of chlorine and bromine.

5. The method of claim 1, wherein the protected hydroxyl is protected with a protecting group selected from the group consisting of alkyl, carbonate, alkyl carbonate, aryl carbonate, acyl, benzyl, mesyl, trityl and tosyl.

6. The method of claim 1, wherein the base is selected from the group consisting of an inorganic and organic base.

7. The method of claim 6, wherein the inorganic base is selected from the group consisting of alkali and alkaline earth hydroxides and carbonates.

8. The method of claim 1, wherein the reactions are carried out in an organic phase.

9. The method of claim 8, wherein the organic phase is selected from the group consisting of methanol, methylisobutylketone, and 2-propanol.

10. The method of claim 1, wherein isolation of step c) is effected by filtration.

11. The method of claim 1, wherein R' is 4-isobutylphenyl and R" is hydrogen.

12. The method of claim 11, wherein the hydroxyalkyl sulfonic acid sultone is 1 3-propane sultone.

13. The method of claim 12, wherein the reaction proceeds for about 1 hour.

14. The method of claim 12, wherein the reaction is carried out in methylisobutylketone.

15. The method of claim of 11, wherein the hydroxyalkyl sulfonic acid sultone is 1,4-butane sultone.

16. The method of claim 15, wherein the reaction proceeds for about 2 hours.

17. The method of claim 15, wherein the reaction is carried out in boiling 2-propanol.

18. The method of claim 1, wherein R' is 6-methoxy-2-naphthyl and R" is hydrogen.

19. The method of claim 18, wherein the hydroxyalkyl sulfonic acid sultone is 1,3-propane sultone.

20. The method of claim 19, wherein the reaction proceeds for about 14 hours.

21. The method of claim 19, wherein the reaction is carried out in a solution comprising about 20% methanol and 80% methyl isobutyl ketone solution.

22. The method of claim 1, wherein R' is chlorine and R" is hydrogen.

23. The method of claim 22, wherein the hydroxyalkyl sulfonic acid sultone is 1,3-propane sultone.

24. The method of claim 23, wherein the reaction proceeds for about 14 hours.

25. The method of claim 23, wherein the reaction is carried out in methylisobutylketone.

26. A method for preparing an ester compound of formula (II),

(II)

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of aryl and alkyl, Y² is —SO₃H and salt thereof, comprising:
a) mixing in trifluoroacetic acid the compound of formula (III),

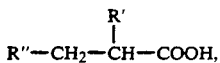
(III)

wherein R' is selected from the group consisting of aryl, aryloxy, alkyl, hydroxyl, protected hydroxyl and halogen, and R" is selected from the group consisting of hydrogen, benzyl, protected thiol and thiol, with a compound selected from the group consisting of hydroxyalkyl and hydroxyaryl sulfonic acid salt,
b) adding trifluoroacetic anhydride to said mixture in step a), and
c) isolating the compound of formula II formed in step b).

27. The method of claim 26, wherein the protected hydroxyl is protected with a protecting group selected from the group consisting of alkyl, carbonate, alkyl carbonate, aryl carbonate, acyl, benzyl, mesyl, trityl and tosyl.

28. The method of claim 26, wherein the protected thiol is protected with a protecting group selected from the group consisting of acetyl, benzoyl and thiocarbamoyl.

29. The method of claim 26, wherein the aryloxy group is selected from the group consisting of 4-hydroxyphenoxy, 4-chlorophenoxy and 2-methyl-4-chlorophenoxy.

30. The method of claim 26, wherein R' is a halogen selected from the group consisting of chlorine and bromine.

31. The method of claim 26, wherein R' is 4-isobutylphenyl and R" is hydrogen.

32. The method of claim 31, wherein the hydroxyalkyl sulfonic acid salt of step a) is selected from the group consisting of sodium formaldehyde bisulfite and isethionic acid sodium salt.

33. The method of claim 26, wherein R' is 6-methoxy-2-naphthyl and R" is hydrogen.

34. The method of claim 33, wherein the hydroxyalkyl sulfonic acid salt of step a) is sodium formaldehyde bisulfite.

35. A method for preparing an ester compound of formula (II),

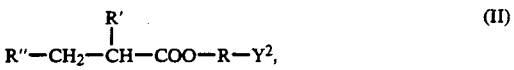
(II)

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of aryl and alkyl, and Y² is —SO₃H and salt thereof, comprising:
a) mixing the compound of formula (III),

(III)

wherein R' is selected from the group consisting of aryl, aryloxy, alkyl, hydroxyl, protected hydroxyl and halogen, and R" is selected from the group consisting of hydrogen, benzyl, protected thiol and thiol, with an inorganic acid chloride to form the acid chloride of the compound of formula III in solution,
b) reacting said formed acid chloride of the compound of formula III of step a) with a compound selected from the group consisting of hydroxyalkyl and hydroxyaryl sulfonic acid salt, and
c) isolating the compound of formula II formed in step b).

36. The method comprising of claim 35, wherein the inorganic acid chloride of step a) is selected from the group consisting of thionyl chloride, phosphorus trichloride, and phosphorus pentachloride.

37. The method of claim 35, wherein the protected hydroxyl is protected with a protecting group selected from the group consisting of alkyl, carbonate, alkyl carbonate, aryl carbonate, acyl, benzyl, mesyl, trityl and tosyl.

38. The method of claim 35, wherein the protected thiol is protected with a protecting group selected from the group consisting of acetyl, benzoyl and thiocarbamoyl.

39. The method of claim 35, wherein the aryloxy group is selected from the group consisting of 4-hydroxyphenoxy, 4-chlorophenoxy and 2-methyl-4-chlorophenoxy.

40. The method of claim 35, wherein R' is a halogen selected from the group consisting of chlorine and bromine.

41. The method of claim 35, wherein R' is 4-isobutylphenyl and R" is hydrogen.

42. The method comprising of claim 41, wherein the hydroxyalkyl sulfonic acid salt of step b) is sodium formaldehyde bisulfite.

43. The method of claim 35, wherein R' is 6-methoxy-2-naphthyl and R" is hydrogen.

44. The method of claim 43, wherein the hydroxyalkyl sulfonic acid salt of step b) is selected from the group consisting of isethionic acid sodium salt and sodium formaldehyde bisulfite.

45. The method of claim 35, wherein R' is methyl and R" is a protected thiol, protected with a protecting group selected from the group consisting of acetyl and benzoyl.

46. The method comprising of claim 45, wherein the hydroxalkyl sulfonic acid salt of step b) is sodium formaldehyde bisulfite.

47. The method of claim 65, wherein R' is 4-chlorophenoxy and R" is hydrogen.

48. The method comprising of claim 47, wherein the hydroxyalkyl sulfonic acid salt of step b) is sodium formaldehyde bisulfite.

49. A method for preparing an ester compound of formula (IV),

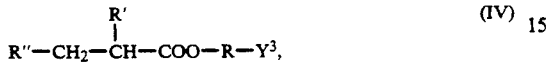

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, $Y^3$ is $-OSO_3H$ and salt thereof, comprising:

a) reacting a compound of formula (V),

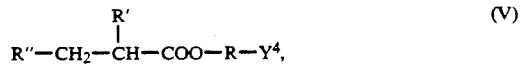

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, and $Y^4$ is hydroxyl, in solution with a sulfonating agent, and b) isolating the compound of formula IV formed in step a).

50. The method of claim 49, wherein the protected hydroxyl is protected with a protecting group selected from the group consisting of alkyl, carbonate, alkyl carbonate, aryl carbonate, acyl, benzyl, mesyl, trityl and tosyl.

51. The method of claim 49, wherein the protected thiol is protected with a protecting group selected from the group consisting of acetyl, benzoyl and thiocarbamoyl.

52. The method of claim 49, wherein the aryloxy group is selected from the group consisting of 4-hydroxyphenoxy, 4-chlorophenoxy and 2-methyl-4-chlorophenoxy.

53. The method of claim 49, wherein R' is a halogen selected from the group consisting of chlorine and bromine.

54. The method of claim 49, wherein the sulfonating agent of step a) is selected from the group consisting of chlorosulfonic acid and $SO_3$.

55. The method of claim 49, wherein R" is hydrogen and R' is selected from the group consisting of 2-(4-isobutylphenyl) and 6-methoxy-2-naphthyl.

56. The method of claim 55, wherein R is propyl.

57. A method for preparing an ester compound of formula (VI),

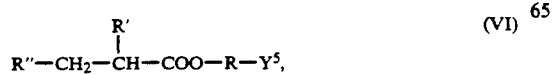

wherein R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, $Y^5$ is $-OPO_3H_2$ and salt thereof, comprising:

a) reacting the compound of formula (V),

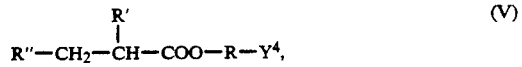

R' is selected from the group consisting of aryl, aryloxy, alkyl, hydroxyl, protected hydroxyl and halogen, R" is selected from the group consisting of hydrogen, benzyl, protected thiol and thiol, R is selected from the group consisting of alkyl and aryl, and $Y^4$ is hydroxyl, in solution with phosphorylating agent or derivative; and b) isolating the compound of formula VI formed in step a).

58. The method of claim 57, wherein the protected hydroxyl is protected with a protecting group selected from the group consisting of alkyl, carbonate, alkyl carbonate, aryl carbonate, acyl, benzyl, mesyl, trityl and tosyl.

59. The method of claim 57, wherein the protected thiol is protected with a protecting group selected from the group consisting of acetyl, benzoyl and thiocarbamoyl.

60. The method of claim 57, wherein the aryloxy group is selected from the group consisting of 4-hydroxyphenoxy, 4-chlorophenoxy and 2-methyl-4-chlorophenoxy.

61. The method of claim 57, wherein R' is a halogen selected from the group consisting of chlorine and bromine.

62. The method of claim 57, wherein R" is H and R' is selected from the group consisting of 6-methoxy-2-naphthyl and 4-isobutylphenyl.

63. The method of claim 62, wherein R is ethyl.

64. A method for preparing an ester compound of formula (VII),

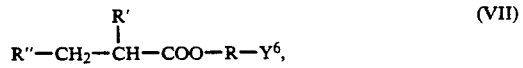

wherein R' is selected from the group consisting of aryl, aryloxy, alkyl, hydroxy, protected hydroxyl and halogen, R" is selected from the group consisting of hydrogen, benzyl, protected thiol and thiol, R is selected from the group consisting of alkyl and aryl, $Y^6$ is $-NZ_3$ and salt thereof, and Z is selected from the group consisting of aryl and alkyl, comprising:

a) reacting a compound of formula (III),

wherein R' is selected from the group consisting of aryl, aryloxy, alkyl, hydroxyl, protected hydroxyl and halogen, and R" is selected from the group consisting of hydrogen, benzyl, protected thiol and thiol, with the acid chloride of an inorganic acid to form the acid chloride of the compound of formula III, b) isolating said formed acid chloride of the compound of formula III of step a), c) mixing said acid chloride of step b) with a compound of formula, $Z_2N13$ R—OH, to form an ester, d) isolating the ester of the compound of formula III formed in step c), e) reacting said ester of the compound of formula III of step d) with an alkylating agent, and f) isolating the compound of formula VII formed in set e).

65. The method comprising of claim 64, wherein the inorganic acid chloride of step a) is selected from the group consisting of thionyl chloride, phosphorus trichloride, and phosphorus pentachloride.

66. The method of step e) of claim 64, wherein the alkylating agent is selected from the group consisting of an alkylhalide, dialkyl sulfate and sulphonic acid alkyl ester.

67. The method of claim 64, wherein the wherein the protected hydroxyl is protected with a protecting group selected from the group consisting of alkyl, carbonate, alkyl carbonate, aryl carbonate, acyl, benzyl, mesyl, trityl and tosyl.

68. The method of claim 64, wherein the protected thiol is protected with a protecting group selected from the group consisting of acetyl, benzoyl and thiocarbamoyl.

69. The method of claim 64, wherein the aryloxy group is selected from the group consisting of 4-hydroxyphenoxy, 4-chlorophenoxy and 2-methyl-4-chlorophenoxy.

70. The method of claim 64, wherein R' is a halogen selected from the group consisting of chlorine and bromine.

71. The method of claim 64, wherein R' is 4-isobutylphenyl and R" is hydrogen.

72. The method of step c) of claim 71, wherein the $Z_2N$—R—OH of step c) is 2-(N,N-dimethylamino)ethanol.

73. The method of claim 64, wherein R' is 6-methoxy-2-naphthyl and R" is hydrogen.

74. The method of step c) of claim 73, wherein the $Z_2N$—R—OH of step c) is selected from the group consisting of 2-(N,N-dimethylamino)ethanol and 3-(N,N-dimethylamino)propanol.

75. A compound of the formula (I),

wherein:

R is selected from the group consisting of alkyl and aryl;

R' is selected from the group consisting of aryl, aryloxy, alkyl, hydroxyl, protected hydroxyl and halogen;

R" is selected from the group consisting of hydrogen, benzyl, protected thiol and thiol; and $Y^1$—is an inorganic acid or salt thereof selected from the group consisting of —$SO_3^-$, —$OSO_3^-$, —$OPO_3^-$, —$SO_3H$, —$OSO_3H$ and —$OPO_3H_2$.

76. The compound of claim 75, wherein the protected thiol is protected with a protecting group selected from the group consisting of acetyl, benzoyl and thiocarbamoyl.

77. The compound of claim 75, wherein the protected hydroxyl is protected with a protecting group selected from the group consisting of alkyl, carbonate, alkyl carbonate, aryl carbonate, acyl, benzyl, mesyl, trityl and tosyl.

78. The compound of claim 75, wherein R' is a halogen selected from the group consisting of chlorine and bromine.

79. The compound of claim 75, wherein the aryloxy group is selected from the group consisting of 4-hydroxyphenoxy, 4-chlorophenoxy and 2-methyl-4-chlorophenoxy.

80. The compound of claim 75, wherein the inorganic acid is selected from the group consisting of —$SO_3H$, —$OSO_3H$ and —$OPO_3H_2$.

81. The compound of claim 75, wherein the salt of the inorganic acid is selected from the group of anionic species consisting of —$SO_3^-$, —$OSO_3^-$, —$OPO_3^-H$ and —$OPO_3^=$, and from the group of cationic species consisting of alkali metal, alkaline earth metal and ammonium.

82. The compound of claim 81, wherein the alkali metal is selected from the group consisting of sodium and potassium.

83. The compound of claim 81, wherein the alkaline earth metal is selected from the group consisting of magnesium and calcium.

84. The compound of claim 81, wherein the ammonium specie has the formula $NQ_4$ wherein Q is selected from the group consisting of hydrogen and hydrocarbon.

85. The compound of claim 84, wherein the hydrocarbon is selected from the group of alkyl and aryl.

86. The compound of claim 75, wherein R' is 4-isobutylphenyl and R" is hydrogen.

87. The compound of claim 86, wherein R is an alkyl containing up to four carbon atoms.

88. The compound of claim 87 wherein $Y^1$ is the salt of an inorganic acid of the formula —$SO_3^-$.

89. The compound of claim 86, wherein R is propyl and $Y^1$ is the salt of an inorganic acid of the formula —$OSO_3^-$.

90. The compound of claim 86, wherein R is ethyl and $Y^1$ is the salt of an inorganic acid of the formula selected from the group consisting of —$OPO_3^=$ and —$OPO_3^-H$.

91. The compound of claim 75, wherein R' is 6-methoxy-2-naphthyl and R" is hydrogen.

92. The compound of claim 91, wherein R is an alkyl containing up to three carbon atoms.

93. The compound of claim 92 wherein $Y^1$ is the salt of an inorganic acid of the formula —$SO_3^-$.

94. The compound of claim 75 wherein R' is an halogen selected from the group consisting of chlorine and bromine and R" is hydrogen.

95. The compound of claim 94 wherein R is propyl and $Y^1$ is the salt of an inorganic acid of the formula —$SO_3^-$.

96. The compound of claim 75, wherein R' is methyl and R" is thiol which is derivatized with a protecting group selected from the group consisting of acetyl and benzoyl.

97. The compound of claim 96, wherein R is methyl and $Y^1$ is the salt of an inorganic acid of the formula —$SO_3^-$.

98. The compound of claim 75 wherein R" is benzoyl and R' is selected from the group consisting of halogen and hydroxyl.

99. The compound of claim 98 wherein the halogen is selected from the group consisting of chlorine and bromine.

100. The compound of claim 75, wherein R" is hydrogen and R' is 4-chlorophenoxy.

101. The compound of claim 100 wherein R is methyl and $Y^1$ is the salt of an inorganic acid of the formula —$SO_3^-$.

* * * * *